US012630549B2

(12) United States Patent
Bell et al.

(10) Patent No.: US 12,630,549 B2
(45) Date of Patent: May 19, 2026

(54) PYRAZOLEAMIDE DERIVATIVES

(71) Applicant: Hoffmann-La Roche Inc., Little Falls, NJ (US)

(72) Inventors: Andrew Simon Bell, Dundee (GB); Jérémy Besnard, Oxford (GB); Anthony Richard Bradley, Dundee (GB); Luke Green, Basel (CH); Wolfgang Haap, Lörrach (DE); Buelent Kocer, Maulburg (DE); Andreas Kuglstatter, Lörrach (DE); Xavier Lucas, Basel (CH); Patrizio Mattei, Riehen (CH); Dmitry Mazunin, Grenzach-Wyhlen (DE); Claus Riemer, Freiburg (DE); Willem Paul Van Hoorn, Dundee (GB)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 396 days.

(21) Appl. No.: 18/361,526

(22) Filed: Jul. 28, 2023

(65) Prior Publication Data

US 2023/0382911 A1 Nov. 30, 2023

Related U.S. Application Data

(63) Continuation of application No. PCT/EP2022/051823, filed on Jan. 27, 2022.

(30) Foreign Application Priority Data

Jan. 29, 2021 (EP) .................................... 21154295

(51) Int. Cl.
*C07D 471/04* (2006.01)
*C07D 487/04* (2006.01)

(52) U.S. Cl.
CPC ......... *C07D 471/04* (2013.01); *C07D 487/04* (2013.01)

(58) Field of Classification Search
CPC ............................ C07D 471/04; C07D 487/04
See application file for complete search history.

(56) References Cited

FOREIGN PATENT DOCUMENTS

| | | | |
|---|---|---|---|
| CN | 106146493 | A1 | 11/2016 |
| JP | 2013-507425 | | 3/2013 |
| RU | 2019108280 | A | 9/2020 |
| WO | 2011/045344 | | 4/2011 |
| WO | 2014/207213 | A1 | 12/2014 |
| WO | 2016/161960 | A1 | 10/2016 |
| WO | 2018/039310 | A1 | 3/2018 |

OTHER PUBLICATIONS

Bastin, R., et al., "Salt Selection and Optimisation Procedures for Pharmaceutical New Chemical Entities" Org Proc Res Dev 2000 4(5):427-435 (Jul. 19, 2000).

Belikov et al. Pharmaceutical Chemistry (Textbook pages in Russian with English translation attached), Moscow:MEDpress-inform,:pp. 27-29 ( 2007).

Kummerer, K., "Pharmaceuticals in the Environment" Ann Rev Environ Res 35:57-75 (Nov. 1, 2010).

Andrist, A., et al., "Facile preparation of optically active c-2,t-3-dimethyl-r-1-methoxycyclopropane" Acs J Org Chem 43(17):3422-3423 (Aug. 1, 1978).

Ansel, H., et al. Pharmaceutical Dosage Forms and Drug Delivery Systems Balado, M. ed., 6th edition, Malvern, PA USA: Williams and Wilkins,:196-197 (Jan. 1, 1995).

Boyer, J. et al., "Difluoromethylbenzoxazole Pyrimidine Thioether Derivatives: A Novel Class of Potent Non-Nucleoside HIV-1 Reverse Transcriptase Inhibitors" ACS J Med Chem 54(23):7974-7985 (Oct. 21, 2011).

Clough, J. et al., "Radical cyclisations of propargyl bromoamides and propargyl bromoesters. New routes to tetramic acids, pyrrolinones, tetronic acids and butenolides" Tetrahedron 30(52):7469-7472 (Oct. 31, 1989).

"International Preliminary Report on Patentability—PCT/EP2022/051823" (Report Issuance Date: Jul. 31, 2023; Chapter I),:pp. 1-7 (Aug. 10, 2023).

"International Search Report—PCT/EP2022/051823" (w/Written Opinion),:pp. 1-78 (Apr. 21, 2022).

Kryukov, G., et al., "MTAP deletion confers enhanced dependency on the PRMT5 arginine methyltransferase in cancer cells" Science 351(6278):1214-1218 (Mar. 11, 2016).

Langhals, H., et al., "Wanderungstendenzen cyclischer, polycyclischer und methylverzweigter Alkylreste bei der Beckmann-Umlagerung (Migration Aptitudes of Cyclic, Polycyclic and Branched Alkyl Groups in the Beckmann Rearrangements)" Chem Berichte—Eur J Inorganic Chem (German w/Eng. Abstract), 114(12):3831-3854 (Dec. 1, 1981).

(Continued)

*Primary Examiner* — Jared Barsky

(74) *Attorney, Agent, or Firm* — Thomas | Horstemeyer, LLP

(57) ABSTRACT

The present invention provides compounds of formula I or II:

(I)

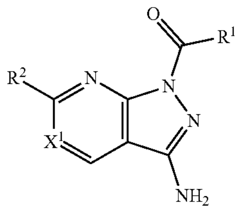

wherein $X^1$, $R^1$ and $R^2$ are as described herein, as well as pharmaceutically acceptable salts thereof. Further the present invention is concerned with the manufacture of the compounds of formula I, pharmaceutical compositions comprising them and their use as medicaments.

5 Claims, No Drawings

(56) References Cited

OTHER PUBLICATIONS

Lapa, G., et al., "Regioselective acylation of congeners of 3-amino-1H-pyrazolo[3,4-b]quinolines, their activity on bacterial serine/threonine protein kinases and in vitro antibacterial (including antimycobacterial) activity" J Enzyme Inhib Med Chem 28(5):1088-1093 (Sep. 7, 2013).
Lynch, B. et al., "Pyrazolo[3,4-b]pyridines: Syntheses, reactions, and nuclear magnetic resonance spectra" Canadian J Chem 66(3):420-428 (Mar. 1, 1988).
March, J. Advanced Organic Chemistry: Reactions, Mechanisms and Structure "Chapter 4: Stereochemistry" March, J., ed., Fourth edition, New York, NY USA: John Wiley & Sons, Inc.,:94-150 (Jan. 1, 1992).
Marjon, K, et al., "MTAP Deletions in Cancer Create Vulnerability to Targeting of the MAT2A/PRMT5/RIOK1 Axis" Cell Reps 15(3):574-587 (Apr. 19, 2016).
Mavrakis, K., et al., "Disordered methionine metabolism in MTAP/CDKN2A-deleted cancers leads to dependence on PRMT5" Science 351(6278):1208-1213 (Mar. 11, 2016).
Pubchem et al., CAS Registry Database, 38041-19-9, CID: 419223 (4-Aminotetrahydropyran; C5H11NO), pp. 1-2; Creation Date Mar. 26, 2005.
Pubchem et al., CAS Registry Database, 1135283-22-5, CID 40148051 (5-Chloro-6-cyclopropyl-1H-pyrazolo[3,4-b]pyridin-3-ylamine; C9H9CIH4), pp. 1-4; Creation Date May 30, 2009.
Pubchem et al., CAS Registry Database, 1211578-87-8, CID 54594002 (6-(Trifluoromethyl-1H-pyrazolo [3,4-b]pyridin-3-amine; C7H5F3N4), pp. 1-4; Creation Date Dec. 16, 2011.
Pubchem et al., CAS Registry Database, 13702-44-8, CID 12589276 2-Methoxycyclohexane-1-carboxylic acid; C8H1403), pp. 1-4; Creation Date Feb. 8, 2007.
Pubchem et al., CAS Registry Database, 617690-22-9, CID 58055085 ((2S,3R)-3-Methyloxolane-2-carboxylic acid; C6H1003), pp. 1-4; Creation Date Aug. 19, 2012.
Pubchem et al., CAS Registry Database, 930-56-3, (1-(2-Methylcyclopropyl)ethanone; C6H100), pp. 1-4; Creation Date Mar. 27, 2005.
Pubchem et al., CAS Registry Database, 951626-63-4, CID 17571618 (6-Tert-butyl-1H-pyrazolo[3,4-b]pyridin-3-amine; C10H14N4), pp. 1-4; Creation Date Nov. 13, 2007.
Remington, J. Remington: The Science and Practice of Pharmacy Gennaro A., ed., 20th edition, Baltimore, Md.—US: Lippincott Williams and Wikins,:ix-2077 (Jan. 1, 2000).
Rowe, R.C. et al. Handbook of Pharmaceutical Excipients Rowe, R.C., 5th edition, Grayslake, IL-USA: Pharmaceutical Press,:1-6 (Jan. 1, 2005).
Cantini et al., "Exploration of nitrogen heterocycle scaffolds for the development of potent human neutrophil elastase inhibitors" Bioorg. Med. Chem. 29:1-17 ( 2021).
Dyson, G. et al., "Chemistry of Synthetic Drugs (English translation)" (),:12-19 ( 1964).

PYRAZOLEAMIDE DERIVATIVES

CROSS-REFERENCE TO RELATED APPLICATIONS

This application is a Continuation Application of International Patent Application No. PCT/EP2022/051823, filed Jan. 27, 2022, which claims benefit of priority to European Patent Application No. 21154295.6, filed Jan. 29, 2021, each of which is incorporated herein by reference in its entirety.

The present invention provides compounds which are inhibitors of the Human methionine adenosyltransferase 2A (Mat2A), for use in the treatment, prevention and/or delay of progression of Cancer.

In particular, the present invention relates to compounds of formula I:

(I)

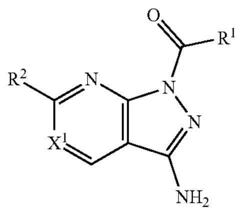

wherein $X^1$ is either N or $CR^3$;

$R^1$ is:

- $(C_3\text{-}C_8)$cycloalkyl optionally substituted with one or more, particularly one to three, more particularly one or two substituents $R^{1a}$,
- heteroaryl optionally substituted with one or more, particularly one to three, more particularly one or two substituents $R^{1b}$,
- heterocycloalkyl optionally substituted with one or more, particularly one to three, more particularly one or two substituents $R^{1c}$; or
- phenyl optionally substituted with one or more, particularly one to three, more particularly one or two substituents $R^{1d}$;

$R^{1a}$, $R^{1b}$, $R^{1c}$ and $R^{1d}$ are each independently selected from halogen, oxo, cyano, hydroxyl, $(C_1\text{-}C_6)$alkyl, $(C_1\text{-}C_6)$alkoxy, $(C_3\text{-}C_6)$cycloalkyl, $(C_3\text{-}C_6)$cycloalkyl-$(C_1\text{-}C_6)$alkyl, halo$(C_1\text{-}C_6)$alkyl, halo$(C_1\text{-}C_6)$alkoxy, hydroxy$(C_1\text{-}C_6)$alkyl, $(C_1\text{-}C_6)$alkoxy-$(C_1\text{-}C_6)$alkyl, heteroaryl, heterocycloalkyl and phenyl;

$R^2$ is $(C_1\text{-}C_6)$alkyl, $(C_1\text{-}C_6)$alkoxy, halo$(C_1\text{-}C_6)$alkyl, halo $(C_1\text{-}C_6)$alkoxy, $(C_3\text{-}C_6)$cycloalkyl optionally substituted with one or more, particularly one to three, more particularly one or two substituents $R^{2a}$, heterocycloalkyl optionally substituted with one or more, particularly one to three, more particularly one or two substituents $R^{2b}$ or phenyl optionally substituted with one or more, particularly one to three, more particularly one or two substituents $R^{2c}$;

$R^{2a}$, $R^{2b}$ and $R^{2c}$ are each independently selected from halogen, $(C_1\text{-}C_6)$alkyl, $(C_1\text{-}C_6)$alkoxy, halo$(C_1\text{-}C_6)$alkyl and halo$(C_1\text{-}C_6)$alkoxy;

$R^3$ is hydrogen, halogen or $(C_1\text{-}C_6)$alkyl;

or $R^2$ and $R^3$ together form $C_{2\text{-}7}$-alkylene optionally substituted with one or more, particularly one to three, more particularly one or two substituents $R^{3f}$ and $R^{3f}$ are each independently selected from halogen, $(C_1\text{-}C_6)$alkyl, and halo$(C_1\text{-}C_6)$alkyl;

and pharmaceutically acceptable salts thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

When indicating the number of substituents, the term "one or more" refers to the range from one substituent to the highest possible number of substitution, i.e. replacement of one hydrogen up to replacement of all hydrogens by substituents, in particular wherein "one or more" refers to one, two or three, most particularly "one or more" refers to one or two.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "amino" denotes a group of the formula —NR'R" wherein R' and R" are independently hydrogen, $(C_1\text{-}C_6)$alkyl, halo$(C_1\text{-}C_6)$alkyl, or $(C_3\text{-}C_6)$cycloalkyl as described herein. Alternatively, R' and R", together with the nitrogen to which they are attached, can form a heterocycloalkyl. The term "primary amino" denotes a group wherein both R' and R" are hydrogen. The term "secondary amino" denotes a group wherein R' is hydrogen and R" is a group other than hydrogen, particularly wherein R" is $(C_1\text{-}C_6)$alkyl. The term "tertiary amino" denotes a group wherein both R' and R" are other than hydrogen, particularly wherein R' and R" are both $(C_1\text{-}C_6)$alkyl. Particular secondary and tertiary amines are methylamine, ethylamine, propylamine, isopropylamine, phenylamine, benzylamine dimethylamine, diethylamine, dipropylamine and diisopropylamine, most particularly amino refers to ethylamine.

"halo" or "halogen" means fluoro, chloro, bromo or iodo, particularly chloro or fluoro.

"hydroxy" refers to a —OH group.

"$(C_1\text{-}C_6)$alkyl" refers to a branched or straight hydrocarbon chain of one to six carbon atoms, such as methyl, ethyl, n-propyl, isopropyl, n-butyl, isobutyl, sec-butyl, t-butyl, pentyl and hexyl.

The term "$(C_1\text{-}C_6)$alkylene" denotes a linear saturated divalent hydrocarbon group of 1 to 6 carbon atoms or a divalent branched saturated hydrocarbon group of 3 to 6 carbon atoms. Examples of alkylene groups include methylene, ethylene, propylene, 2-methylpropylene, butylene, 2-ethylbutylene, pentylene, hexylene. Particular examples for alkylene are ethylene, propylene, and butylene.

"($C_1$-$C_6$)alkoxy" means a moiety of the formula —$OR^a$, wherein $R^a$ is an ($C_1$-$C_6$)alkyl moiety as defined herein. Examples of ($C_1$-$C_6$)alkoxy moieties include, but are not limited to, methoxy, ethoxy, isopropoxy, and the like.

The term "($C_3$-$C_8$)cycloalkyl" denotes a saturated monovalent saturated monocyclic hydrocarbon group of 3 to 6 ring carbon atoms. Examples for monocyclic ($C_3$-$C_8$)cycloalkyl are cyclopropyl, cyclobutanyl, cyclopentyl, cyclopentenyl, cyclohexyl, cyclohexenyl or cycloheptyl. One particular example of ($C_3$-$C_6$)cycloalkyl is cyclopropyl.

"($C_3$-$C_6$)cycloalkyl-($C_1$-$C_6$)alkyl" refers to an ($C_1$-$C_6$) alkyl, as defined above, substituted with one or more ($C_3$-$C_6$)cycloalkyl group, particularly with one ($C_3$-$C_6$)cycloalkyl group. More particularly "($C_3$-$C_6$)cycloalkyl-($C_1$-$C_6$) alkyl refers to

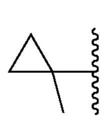

or

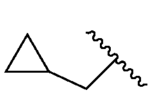

.

The term "perhalo($C_1$-$C_3$)alkyl" means an ($C_1$-$C_3$)alkyl group as defined above wherein all hydrogen atoms have been replaced with halogen atoms. More particularly "($C_1$-$C_3$)perhaloalkyl" is ($C_1$-$C_3$)perfluoroalkyl, most preferably trifluoromethyl.

"halo-($C_1$-$C_6$)alkyl" refers to an ($C_1$-$C_6$)alkyl, as defined above, substituted with one or more halogen atoms, particularly with one to three halogen atoms. More particularly halo-($C_1$-$C_6$)alkyl is the chloro- and fluoro-($C_1$-$C_6$)alkyl. In some particular embodiment halo-($C_1$-$C_6$)alkyl refers to perhalo($C_1$-$C_3$)alkyl as defined herein. Most particularly halo-($C_1$-$C_6$)alkyl is trifluoromethyl, difluoromethyl or fluoromethyl.

"halo-($C_1$-$C_6$)alkoxy" refers to an ($C_1$-$C_6$)alkoxy, as defined above, substituted with one or more halogen atoms, particularly with one to three halogen atoms. More particularly halo-($C_1$-$C_6$) alkoxy is the chloro- and fluoro-($C_1$-$C_6$) alkoxy. In some particular embodiment halo-($C_1$-$C_6$) alkoxy refers to perhalo($C_1$-$C_3$) alkoxy, such as trifluoromethoxy or difluoromethoxy.

"hydroxy-($C_1$-$C_6$)alkyl" refers to an ($C_1$-$C_6$)alkyl, as defined above, substituted with one or more hydroxy group, particularly with one hydroxy group. More particularly hydroxy-($C_1$-$C_6$)alkyl refers to methyl-hydroxide or ethyl-hydroxide.

"($C_1$-$C_6$)alkoxy-($C_1$-$C_6$)alkyl" refers to an ($C_1$-$C_6$)alkyl, as defined above, substituted with one or more ($C_1$-$C_6$) alkoxy group as defined herein, particularly with one ($C_1$-$C_6$)alkoxy group. More particularly ($C_1$-$C_6$)alkoxy-($C_1$-$C_6$) alkyl refers to —$CH_2$—O—$CH_3$ or —$CH_2CH_2$—O—$CH_3$.

"halo-($C_1$-$C_6$)alkoxy" refers to an alkoxy, as defined above, substituted with one or more halogen atoms, particularly with one to three halogen atoms. More particularly halo-($C_1$-$C_6$)alkoxy are the chloro- and fluoro-($C_1$-$C_6$) alkoxy.

"Heteroaryl" means a monovalent monocyclic or bicyclic moiety of 5 to 12 ring atoms having at least one aromatic ring containing one, two, or three ring heteroatoms selected each independently from N, O, or S (preferably N or O), the remaining ring atoms being C, with the understanding that the attachment point of the heteroaryl moiety will be on an aromatic ring. More specifically the term heteroaryl includes, but is not limited to, pyridinyl, furanyl, thienyl, thiazolyl, isothiazolyl, triazolyl, imidazolyl, isoxazolyl, oxazolyl, pyrrolyl, pyrazolyl, pyrimidinyl, pyrazinyl, pyridazinyl, benzofuranyl, tetrahydrobenzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl, imidazo[1,2-a]-pyridinyl, imidazo[2,1-b]thiazolyl, and the derivatives thereof. "N-heteroaryl" in particular refers to heteroaryl as previously defined containing at least one nitrogen atom. The point of attachment of the N-heteroaryl to the rest of the molecule can be through the nitrogen or a carbon ring atom. Example of N-heteroaryl are pyridinyl, pyrazinyl, pyridazinyl, pyrimidinyl.

The term "heterocycloalkyl" or "heterocyclic" denotes a monovalent saturated or partly unsaturated mono- or bicyclic ring system of 4 to 9 ring atoms, comprising 1, 2, or 3 ring heteroatoms selected independently from N, O and S, the remaining ring atoms being carbon. Examples for heterocycloalkyl are pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, dioxolane, 1,4-dioxepanyl, oxepanyl, 1,1-dioxo-thiomorpholin-4-yl, azepanyl, diazepanyl, homopiperazinyl, or oxazepanyl. More particularly heterocycloalkyl refers to dihydrofuryl, 1,3-dioxolyl, dihydropyrryl, dihydrothiophyl, dihydropyrazolyl, dihydroisoxazolyl, tetrahydropyridyl, tetrahydropyranyl, tetrahydrothiopyranyl, piperazinyl, 3,4-dihydro-2H-1,4-oxazinyl, 3,4-dihydro-2H-1,4-thiazyl, 1,2,3,4-tetrahydropyrazyl.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

The terms "individual" or "subject" refer to a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

The terms "compound(s) of this invention" and "compound(s) of the present invention" refer to compounds as disclosed herein and stereoisomers, tautomers, solvates, and salts (e.g., pharmaceutically acceptable salts) thereof.

When the compounds of the invention are solids, it is understood by those skilled in the art that these compounds, and their solvates and salts, may exist in different solid forms, particularly different crystal forms, all of which are intended to be within the scope of the present invention and specified formulae.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The term "active pharmaceutical ingredient" (or "API") denotes the compound or molecule in a pharmaceutical composition that has a particular biological activity.

The terms "pharmaceutical composition" and "pharmaceutical formulation" (or "formulation") are used interchangeably and denote a mixture or solution comprising a therapeutically effective amount of an active pharmaceutical ingredient together with pharmaceutically acceptable excipients to be administered to a mammal, e.g., a human in need thereof.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The terms "treating" or "treatment" of a disease state include inhibiting the disease state, i.e., arresting the development of the disease state or its clinical symptoms, or relieving the disease state, i.e., causing temporary or permanent regression of the disease state or its clinical symptoms.

Compounds that have the same molecular formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula I can possess one or more asymmetric centers or axes. Unless indicated otherwise, the description or naming of a particular compound in the specification and claims is intended to include both individual enantiomers, atropisomers and mixtures, racemic or otherwise, thereof, as well as individual epimers, atropisomers and mixtures thereof. The methods for the determination of stereochemistry and the separation of stereoisomers are well-known in the art (see discussion in Chapter 4 of "Advanced Organic Chemistry", 4th edition J. March, John Wiley and Sons, New York, 1992).

Certain compounds may exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(═O)—CH—↔—C(—OH)═CH—), amide/imidic acid (—C(═O)—NH—↔—C(—OH)═N—) and amidine (—C(═NR)—NH—↔—C(—NHR)═N—) tautomers. The latter two are particularly common in heteroaryl and heterocyclic rings and the present invention encompasses all tautomeric forms of the compounds.

Now it has been found that the present compounds of formula I are inhibitors of Mat2A and as such may be of therapeutic use for the treatment of Cancer disorders including Lung Aenocarcinoma, Melanoma, Pancreatic Adenocarcinoma, Head and Neck Squamous Cell Carcinoma, Lung Squamous Cell Carcinoma, Esophageal Carcinoma, Glioblastoma Multiforme, and Mesothelioma.

These compounds are potent inhibitors of the Human methionine adenosyltransferase II alpha (MAT2A). MAT2A and MAT1A (methionine adenosyltransferase I alpha) are two genes that encode for methionine adenosyltransferase activity thereby producing S-adenosylmethionine (SAM), the principal methyl donor in the cells. MAT1A is the liver specific SAM producing enzyme, whereas MAT2A is broadly expressed, except in the liver. MAT2A is found in complex with MAT2B (methionine adenosyltransferase II beta), the allosteric regulator of MAT2A, and MAT2B acts like a rheostat for MAT2A enzymatic activity. When MAT2B binds to MAT2A, MAT2A undergoes a conformational change that increases its affinity for methionine and SAM. The net effect is that MAT2A, when bound to MAT2B, is more active under low methionine concentrations, but is inhibited under high methionine concentrations.

Loss-of-function mutations in tumor suppressor genes are critical in the molecular pathogenesis of cancer, however successful targeting of tumor suppressors has been elusive mainly because the mutant proteins cannot be directly inhibited for therapeutic benefit, and restoration of mutant function (such as restoring function of mutant p53), has so far not been possible. The recent clinical success of inhibiting PARP in BRCA1/2 deficient patients has shown that targeting conditional synthetic lethalities (CSLs) that arise from loss-of-function mutations in tumor suppressors is a clinically valid approach for the treatment of cancers. The CSL relationship is not only valid for tumor suppressors but can be extended to genes that reside in the same genetic region of a tumor suppressor and are lost when that region is deleted. Methylthioadenosine phosphorylase (MTAP) is one such gene that is in close proximity to the tumor suppressor CDKN2A, and is deleted in ~15% of all cancers. MTAP is deleted in, but not limited to, ~53% of glioblastoma multiforme (GBM), ~25% of pancreatic adenocarcinoma (PDAC), ~25% of melanoma, ~23% lung squamous cell carcinoma, ~20% head and neck squamous cell carcinoma, and ~15% lung adenocarcinoma. Indeed, this deletion occurs across multiple indications, many of which are areas of high unmet medical need with limited efficacious therapies. In glioblastoma, were the median survival is 14 months, the approval of the most recent therapies has not increased the overall survival (OS) time significantly and the standard of care (SoC) remains the same for over a decade. The same is true for the majority of patients with PDAC where OS is less than 1 year. MTAP deletion is a truncal event that occurs early on in tumor development and would be carried through all evolutions of the tumor including metastasis. Therefore its loss represents an alteration that is not affected by tumor heterogeneity, genetic background, or resistance to any approved agents in the clinic. A CSL relationship identified for MTAP deficiency would represent a true Achilles' heel for multiple tumor indications.

MTAP is located in close proximity to the tumor suppressor CDKN2A on chromosome 9. When CDKN2A is deleted, MTAP is frequently co-deleted. Its loss is thought to be a bystander effect and phenotypically neutral. MTAP is the cornerstone of the adenine and methionine salvage pathways in cells. The methionine salvage pathway feeds into the SAM production pathway, and the levels of SAM are a key regulator of cancer cell growth that needs to be tightly regulated because large changes in SAM concentrations, either increases or decreases, lead to cell cycle arrest. The importance of SAM levels to cancerous growth lies in its central role for protein, DNA, and RNA methylation, acting as a checkpoint for the health of the cell, and can be read out as hypomethylation when SAM is reduced or hypermethylation when SAM is increased. Cells that lack MTAP accumulate methylthioadenosine (MTA) and decarboxylated SAM (dcSAM) without adversely affecting the levels of any salvage metabolites/products including SAM. This accumulation creates a novel stress on the cell where MTA acts as a competitive inhibitor of SAM dependent reactions due to their structural similarity. The loss of MTAP forces the cell to adapt to the new MTA/SAM paradigm without any loss in viability that a MTAP proficient cell would not have to contend with, and this adaptation creates a robust dependence on methionine adenosyltransferase II alpha2 (MAT2A), one of the enzymes that produces SAM, in MTAP deficient cells. This conditional synthetic lethal (CSL) relationship of MTAP loss and MAT2A dependence was identified in three large scale shRNA screens (Marjon Cell Reports 2016, Kryukov Science 2016, and Mavrakis Science 2016).

Targeting MAT2A with a small molecule inhibition would bring benefit to a genetically defined patient population representing many areas of high unmet medical need.

Objects of the present invention are compounds of formula I the use of such compounds for the preparation of medicaments for the treatment, prevention and/or delay of progression of Cancer, in particular Lung Aenocarcinoma, Melanoma, Pancreatic Adenocarcinoma, Head and Neck Squamous Cell Carcinoma, Lung Squamous Cell Carcinoma, Esophageal Carcinoma, Glioblastoma Multiforme, and Mesothelioma more particularly for the treatment of cancer including Lung Adenocarcinoma, Lung Squamous Carcinoma, Pancreatic Adenocarcinoma, Glioblastoma Multiforme, and Head and Neck Squamous Carcinoma, their manufacture and medicaments based on a compound of formula I in accordance with the invention.

Further objects of the present invention are all forms of optically pure enantiomers, racemates or diastereometric mixtures for compounds of formula I.

In particular, the present invention relates to compounds of formula I:

(I)

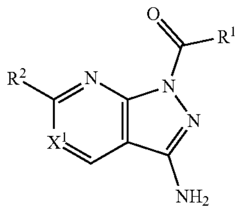

wherein $X^1$ is either N or $CR^3$;

$R^1$ is:

- $(C_3\text{-}C_8)$cycloalkyl optionally substituted with one or more, particularly one to three, more particularly one or two substituents $R^{1a}$,
- heteroaryl optionally substituted with one or more, particularly one to three, more particularly one or two substituents $R^{1b}$,
- heterocycloalkyl optionally substituted with one or more, particularly one to three, more particularly one or two substituents $R^{1c}$; or
- phenyl optionally substituted with one or more, particularly one to three, more particularly one or two substituents $R^{1d}$;

$R^{1a}$, $R^{1b}$, $R^{1c}$ and $R^{1d}$ are each independently selected from halogen, oxo, cyano, hydroxyl, $(C_1\text{-}C_6)$alkyl, $(C_1\text{-}C_6)$alkoxy, $(C_3\text{-}C_6)$cycloalkyl, $(C_3\text{-}C_6)$cycloalkyl-$(C_1\text{-}C_6)$alkyl, halo$(C_1\text{-}C_6)$alkyl, halo$(C_1\text{-}C_6)$alkoxy, hydroxy$(C_1\text{-}C_6)$alkyl, $(C_1\text{-}C_6)$alkoxy-$(C_1\text{-}C_6)$alkyl, heteroaryl, heterocycloalkyl and phenyl;

$R^2$ is $(C_1\text{-}C_6)$alkyl, halo$(C_1\text{-}C_6)$alkyl, $(C_3\text{-}C_6)$cycloalkyl optionally substituted with one or more, particularly one to three, more particularly one or two substituents $R^{2a}$, heterocycloalkyl optionally substituted with one or more, particularly one to three, more particularly one or two substituents $R^{2b}$ or phenyl optionally substituted with one or more, particularly one to three, more particularly one or two substituents $R^{2c}$;

$R^{2a}$, $R^{2b}$ and $R^{2c}$ are each independently selected from halogen, $(C_1-C_6)$alkyl, $(C_1-C_6)$alkoxy, halo$(C_1-C_6)$alkyl and halo$(C_1-C_6)$alkoxy;

$R^3$ is hydrogen, halogen or $(C_1-C_6)$alkyl;

or $R^2$ and $R^3$ together form $C_{2-7}$-alkylene optionally substituted with one or more, particularly one to three, more particularly one or two substituents $R^{3f}$ and $R^{3f}$ are each independently selected from halogen, $(C_1-C_6)$alkyl, and halo$(C_1-C_6)$alkyl;

and pharmaceutically acceptable salts thereof.

In particular embodiment, the present invention relates to compounds of formula I':

(I')

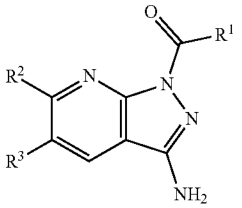

wherein $R^1$, $R^2$ and $R^3$ are as defined herein and pharmaceutically acceptable salts thereof.

Further, it is to be understood that every embodiment relating to a specific $X^1$, $R^1$, $R^{1a}$, $R^{1b}$, $R^{1c}$, $R^{1d}$, $R^2$, $R^{2a}$, $R^{2b}$, $R^{2c}$, $R^3$, $R^{3a}$, $R^{3b}$, $R^{3c}$, $R^{3d}$ and $R^{3e}$ as disclosed herein may be combined with any other embodiment relating to another $X^1$, $R^1$, $R^{1a}$, $R^{1b}$, $R^{1c}$, $R^{1d}$, $R^2$, $R^{2a}$, $R^{2b}$, $R^{2c}$, $R^3$, $R^{3a}$, $R^{3b}$, $R^{3c}$, $R^{3d}$ and $R^{3e}$ as disclosed herein.

A particular embodiment of the present invention relates to a compound of formula I, wherein $X^1$ is $CR^3$.

A particular embodiment of the present invention relates to a compound of formula I or I', wherein $R^1$ is $(C_3-C_8)$cycloalkyl optionally substituted with one substituents $R^{1a}$, heteroaryl optionally substituted with one $R^{1b}$, heterocycloalkyl optionally substituted with one or two $R^{1c}$ or phenyl optionally substituted with one or two $R^{1d}$; particularly $R^1$ is $(C_3-C_6)$cycloalkyl optionally substituted with one $R^{1a}$, pyridinyl optionally substituted with one $R^{1b}$, pyrazinyl optionally substituted with one $R^{1b}$, pyridizanyl optionally substituted with one $R^{1b}$, thiazolyl optionally substituted with one $R^{1b}$, 1,3-benzodioxolyl optionally substituted with one Rio, oxazolyl optionally substituted with one $R^{1c}$, piperidinyl optionally substituted with one Rio, tetrahydrofuranyl optionally substituted with one $R^{1c}$, tetrahydropyranyl optionally substituted with one $R^{1c}$ or phenyl optionally substituted with one or two $R^{1d}$, more particularly wherein $R^1$ is cyclohexyl optionally substituted with one $R^{1a}$, pyridinyl optionally substituted with one $R^{1b}$, pyrazinyl optionally substituted with one $R^{1b}$, pyridizanyl optionally substituted with one $R^{1b}$, thiazolyl optionally substituted with one $R^{1b}$, 1,3-benzodioxolyl, oxazolyl optionally substituted with one $R^{1c}$, piperidinyl optionally substituted with one $R^{1c}$, tetrahydrofuranyl optionally substituted with one $R^{1c}$, tetrahydropyranyl or phenyl optionally substituted with one or two $R^{1d}$, most particularly $R^1$ is pyridinyl optionally substituted with one $R^{1b}$ or phenyl optionally substituted with one or two $R^{1d}$.

More particular embodiment of the present invention relates to a compound of formula I or I', wherein $R^1$ is heteroaryl optionally substituted with one $R^{1b}$ or phenyl optionally substituted with one or two $R^{1d}$.

A particular embodiment of the present invention relates to a compound of formula I or I', wherein $R^{1a}$, $R^{1b}$, $R^{1c}$ and $R^{1d}$ are each independently selected from halogen, oxo, cyano, $(C_1-C_6)$alkyl, $(C_1-C_6)$alkoxy, halo$(C_1-C_6)$alkyl and halo$(C_1-C_6)$alkoxy, particularly wherein $R^{1a}$, $R^{1b}$, $R^{1c}$ and $R^{1d}$ are each independently selected from halogen, oxo, cyano, $(C_1-C_3)$alkyl, $(C_1-C_3)$alkoxy, halo$(C_1-C_3)$alkyl and halo$(C_1-C_3)$alkoxy, more particularly wherein $R^{1a}$, $R^{1b}$, $R^{1c}$ and $R^{1d}$ are each independently selected from halogen, oxo, cyano, $(C_1-C_3)$alkyl, $(C_1-C_3)$alkoxy and halo$(C_1-C_3)$alkyl, even more particularly wherein $R^{1a}$, $R^{1b}$, $R^{1c}$ and $R^{1d}$ are each independently selected from chloro, fluoro, oxo, cyano, methyl, ethyl, methoxy, trifluoromethyl and difluoromethyl, most particularly wherein $R^{1a}$, $R^{1b}$, $R^{1c}$ and $R^{1d}$ are each independently selected from chloro, fluoro, cyano, methyl and methoxy.

A particular embodiment of the present invention relates to a compound of formula I or I', wherein $R^{1b}$ and $R^{1d}$ are each independently selected from halogen, cyano, $(C_1-C_3)$alkyl, $(C_1-C_3)$alkoxy, halo$(C_1-C_3)$alkyl and halo$(C_1-C_3)$alkoxy, particularly wherein $R^{1b}$ are each independently selected from halogen, $(C_1-C_3)$alkyl, $(C_1-C_3)$alkoxy and halo$(C_1-C_3)$alkyl and wherein $R^{1d}$ are each independently selected from halogen, cyano, $(C_1-C_3)$alkyl, $(C_1-C_3)$alkoxy, halo$(C_1-C_3)$alkyl and halo$(C_1-C_3)$alkoxy, more particularly wherein $R^{1b}$ are each independently selected from chloro, methyl and methoxy and wherein $R^{1d}$ are each independently selected from fluoro, cyano, methyl and methoxy.

A particular embodiment of the present invention relates to a compound of formula I or I', wherein $R^1$ is 2-methoxyphenyl, 2-chlorophenyl, 2-methylphenyl, 1,3-benzodioxol-4-yl, 3-fluoro-2-methylphenyl, 2,3-dimethylphenyl, cyclohexyl, 2-methoxycyclohexyl, 3-fluoro-2-methoxyphenyl, 4-fluoro-2-methoxyphenyl, 3-methyl-2-oxopiperidin-4-yl, 2-ethylphenyl, 2-(difluoromethoxy)phenyl, 5-methyl-1,3-oxazol-4-yl, 4-methyl-1,3-thiazol-5-yl, 2-methyloxolan-3-yl, 3-methyl-tetrahydrofuran-2-yl, 3-cyano-2-methylphenyl, oxan-4-yl, 2-methylpyridin-3-yl, 2-oxopiperidin-4-yl, 2-methoxy-3-methylphenyl, 3-chloro-2-methoxyphenyl, 3-cyano-2-methoxyphenyl, oxan-3-yl, 3-methylpyrazin-2-yl, 2-methoxypyridin-3-yl, 2-chloropyridin-3-yl, 2-(trifluoromethyl)pyridin-3-yl, 3-methylpyridazin-4-yl, 3-methyl-1, 2-thiazol-4-yl or 3-methyltetrahydrofuran-2-yl, in particular wherein $R^1$ is 2-methoxyphenyl, 3-fluoro-2-methoxyphenyl, 2-methylpyridin-3-yl, 3-cyano-2-methoxyphenyl, 2-methoxypyridin-3-yl, 2-chloropyridin-3-yl or 2-methylphenyl.

Another embodiment of the present invention relates to a compound of formula I, I' or I", wherein $R^2$ is $(C_1-C_6)$alkyl, halo$(C_1-C_6)$alkyl, $(C_3-C_6)$cycloalkyl optionally substituted with one or two substituents $R^{2a}$, heterocycloalkyl optionally substituted with one or two substituents $R^{2b}$ or phenyl, particularly wherein $R^2$ is $(C_1-C_3)$alkyl, halo$(C_1-C_3)$alkyl, cyclopropyl optionally substituted with one or two substituents $R^{2a}$, cyclobutyl, cyclopentyl, cyclopentenyl, cylcohexenyl, azetidinyl optionally substituted with one or two substituents $R^{2b}$, dihydrofuranyl, dihydropyranyl, azabicyclo[2.2.1]heptanyl, -azabicyclo[2.2.1]heptanyl, pyrrolidinyl, azetidinyl optionally substituted with one or two substituents $R^{2b}$ or phenyl, more particularly wherein $R^2$ is i-butyl, t-butyl, trifluoromethyl, cyclopropyl optionally substituted with one or two substituents $R^{2a}$, cyclobutyl, cyclopentyl, cyclopentenyl, cylcohexenyl, azetidinyl optionally substituted with one or two substituents $R^{2b}$, 2,5-dihydrofuran-3-yl, 3,4-dihydro-pyran-6-yl, 2-azabicyclo[2.2.1]heptan-2-yl, 7-azabicyclo[2.2.1]heptan-7-yl, pyrrolidinyl, or phenyl, even more particularly wherein $R^2$ is i-butyl, t-butyl, trifluoromethyl, cyclopropyl optionally substituted with one or two substituents selected from fluoro, methyl or trifluoromethyl, cyclobutyl, cyclopentyl, cyclopenten-1-yl, cylcohexen-1-yl, azetidinyl optionally substituted with two fluoro, 2,5-dihydrofuran-3-yl, 3,4-dihydro-pyran-6-yl, 2-azabicyclo[2.2.1]heptan-2-yl, 7-azabicyclo[2.2.1]heptan-7-yl, pyrrolidinyl, or phenyl, most particularly wherein $R^2$ is trifluoromethyl, cylcopropyl, cyclobutyl, cyclopenten-1-yl, 2-fluorocyclopropyl, 2,2-difluorocyclopropyl, 2-(trifluoromethyl)cyclopropyl, 2,3-dimethylcyclopropyl, 1-methylcyclopropyl or 3,4-dihydro-pyran-6-yl.

More particular embodiment of the present invention relates to a compound of formula I or I', wherein $R^2$ is halo($C_1$-$C_6$)alkyl, ($C_3$-$C_6$)cycloalkyl optionally substituted with one or two substituents $R^{2a}$ or heterocycloalkyl optionally substituted with one or two substituents $R^{2b}$.

Another embodiment of the present invention relates to a compound of formula I, I' or I", wherein $R^{2a}$, $R^{2b}$ and $R^{2c}$ are each independently selected from halogen, ($C_1$-$C_3$)alkyl and halo($C_1$-$C_3$)alkyl, particularly $R^{2a}$, $R^{2b}$ and $R^{2c}$ are each independently selected from fluoro, methyl and trifluoromethyl, more particularly $R^{2a}$ are each independently selected from fluoro, methyl and trifluoromethyl, $R^{2b}$ are each fluoro.

A particular embodiment of the present invention relates to a compound of formula I or I', wherein $R^2$ is phenyl, 2-methylpropyl, pyrrolidin-1-yl, cyclopropyl, cyclohexen-1-yl, 3,4-dihydro-2-pyran-6-yl, cyclopenten-1-yl, azetidin-1-yl, trifluoromethyl, 3,3-difluoroazetidin-1-yl, cyclopentyl, cyclobutyl, 2-methylcyclopropyl, 2,5-dihydrofuran-3-yl, 2-fluorocyclopropyl, 2,2-difluorocyclopropyl, 2-(trifluoromethyl)cyclopropyl, 2,3-dimethylcyclopropyl, 1-methylcyclopropyl, 2-azabicyclo[2.2.1]heptan-2-yl, 7-azabicyclo [2.2.1]heptan-7-yl or t-butyl, in particular wherein $R^2$ is cyclopropyl, cyclopenten-1-yl, trifluoromethyl or cyclobutyl, 2,5-dihydrofuran-3-yl.

In yet another embodiment of the present invention relates to a compound of formula I or I', wherein $R^3$ is hydrogen or halogen, in particular wherein $R^3$ is hydrogen, chloro or fluoro, more particularly wherein $R^3$ is hydrogen.

Particular compounds of formula I of the present invention are those selected from the group consisting of.

(3-amino-6-phenyl-1H-pyrazolo[3,4-b]pyridin-1-yl)(2-methoxyphenyl)methanone
(3-amino-6-isobutyl-1H-pyrazolo[3,4-b]pyridin-1-yl)(2-methoxyphenyl)methanone
(3-amino-6-(pyrrolidin-1-yl)-1H-pyrazolo[3,4-b]pyridin-1-yl)(2-methoxyphenyl)methanone
(3-amino-6-(pyrrolidin-1-yl)-1H-pyrazolo[3,4-b]pyridin-1-yl)(2-chlorophenyl)methanone
(3-amino-6-(pyrrolidin-1-yl)-1H-pyrazolo[3,4-b]pyridin-1-yl)(o-tolyl)methanone
[3-amino-6-(cyclohexen-1-yl)pyrazolo[3,4-b]pyridin-1-yl]-(2-methoxyphenyl)methanone
(3-amino-6-cyclopropylpyrazolo[3,4-b]pyridin-1-yl)-(2-methoxyphenyl)methanone 2,2,2-trifluoroacetic acid
(3-amino-5-chloro-6-cyclopropyl-1H-pyrazolo[3,4-b]pyridin-1-yl)(2-methoxyphenyl)methanone
(3-amino-5-chloro-6-cyclopropyl-1H-pyrazolo[3,4-b]pyridin-1-yl)(o-tolyl)methanone
(3-amino-5-fluoro-6-phenyl-1H-pyrazolo[3,4-b]pyridin-1-yl)(2-methoxyphenyl)methanone
(3-amino-5-fluoro-6-(pyrrolidin-1-yl)-1H-pyrazolo[3,4-b]pyridin-1-yl)(2-methoxyphenyl)methanone
(3-amino-5-fluoro-6-(pyrrolidin-1-yl)-1H-pyrazolo[3,4-b]pyridin-1-yl)(2-chlorophenyl)methanone
(3-amino-5-fluoro-6-(pyrrolidin-1-yl)-1H-pyrazolo[3,4-b]pyridin-1-yl)(o-tolyl)methanone
(3-amino-6-(3,3-difluoroazetidin-1-yl)-5-fluoro-1H-pyrazolo[3,4-b]pyridin-1-yl)(2-methoxyphenyl)methanone
(3-amino-6-(tert-butyl)-1H-pyrazolo[3,4-b]pyridin-1-yl)(2-methoxyphenyl)methanone
(3-amino-6-(pyrrolidin-1-yl)-1H-pyrazolo[3,4-d]pyrimidin-1-yl)(2-methoxyphenyl)methanone
(3-amino-6-(pyrrolidin-1-yl)-1H-pyrazolo[3,4-d]pyrimidin-1-yl)(o-tolyl)methanone
(3-amino-6-(pyrrolidin-1-yl)-1H-pyrazolo[3,4-d]pyrimidin-1-yl)(2-chlorophenyl)methanone
(3-amino-6-cyclopropylpyrazolo[3,4-b]pyridin-1-yl)-(1,3-benzodioxol-4-yl)methanone
(3-amino-6-cyclopropylpyrazolo[3,4-b]pyridin-1-yl)-(2-methylphenyl)methanone
(3-amino-7,7-dimethyl-5,6,7,8-tetrahydro-1H-pyrazolo[3,4-b]quinolin-1-yl)(2-methoxyphenyl)methanone
[3-amino-6-(3,4-dihydro-2H-pyran-6-yl)pyrazolo[3,4-b]pyridin-1-yl]-(2-methoxyphenyl)methanone
[3-amino-6-(cyclopenten-1-yl)pyrazolo[3,4-b]pyridin-1-yl]-(2-methoxyphenyl)methanone
(3-amino-6-(azetidin-1-yl)-1H-pyrazolo[3,4-b]pyridin-1-yl)(2-methoxyphenyl)methanone
(3-amino-6-(trifluoromethyl)-1H-pyrazolo[3,4-b]pyridin-1-yl)(o-tolyl)methanone
(3-amino-6-(trifluoromethyl)-1H-pyrazolo[3,4-b]pyridin-1-yl)(2-methoxyphenyl)methanone
(3-amino-6-(3,3-difluoroazetidin-1-yl)-1H-pyrazolo[3,4-b]pyridin-1-yl)(2-methoxyphenyl)methanone
(3-amino-6-(3,3-difluoroazetidin-1-yl)-1H-pyrazolo[3,4-b]pyridin-1-yl)(o-tolyl)methanone
(3-amino-6-cyclopentylpyrazolo[3,4-b]pyridin-1-yl)-(2-methylphenyl)methanone
[3-amino-6-(cyclopenten-1-yl)pyrazolo[3,4-b]pyridin-1-yl]-(2-methylphenyl)methanone
(3-amino-6-cyclobutyl-1H-pyrazolo[3,4-b]pyridin-1-yl)(o-tolyl)methanone
(3-amino-6-cyclobutyl-1H-pyrazolo[3,4-b]pyridin-1-yl)(2-methoxyphenyl)methanone
(3-amino-6-cyclopropyl-1H-pyrazolo[3,4-b]pyridin-1-yl)(3-fluoro-2-methylphenyl)methanone
(3-amino-6-((1RS,2RS)-2-methylcyclopropyl)-1H-pyrazolo[3,4-b]pyridin-1-yl)(o-tolyl)methanone
(3-amino-6-((1RS,2RS)-2-methylcyclopropyl)-1H-pyrazolo[3,4-b]pyridin-1-yl)(2-methoxyphenyl)methanone
(3-amino-6-cyclopropyl-1H-pyrazolo[3,4-b]pyridin-1-yl)(2,3-dimethylphenyl)methanone
(3-amino-6-cyclopropyl-1H-pyrazolo[3,4-b]pyridin-1-yl)(cyclohexyl)methanone
[3-amino-6-(2,5-dihydrofuran-3-yl)pyrazolo[3,4-b]pyridin-1-yl]-(2-methoxyphenyl)methanone
[3-amino-6-(2,5-dihydrofuran-3-yl)pyrazolo[3,4-b]pyridin-1-yl]-(2-methoxyphenyl)methanone
(3-amino-6-cyclopropyl-1H-pyrazolo[3,4-b]pyridin-1-yl)(2-methoxycyclohexyl)methanone
(3-amino-7-methyl-5,6,7,8-tetrahydro-1H-pyrazolo[3,4-b]quinolin-1-yl)(2-methoxyphenyl)methanone
(3-amino-6-((trans)-2-fluorocyclopropyl)-1H-pyrazolo[3,4-b]pyridin-1-yl)(2-methoxyphenyl)methanone
(3-amino-6-cyclopropyl-1H-pyrazolo[3,4-b]pyridin-1-yl)(3-fluoro-2-methoxyphenyl)methanone
(3-amino-6-cyclopropyl-1H-pyrazolo[3,4-b]pyridin-1-yl)(4-fluoro-2-methoxyphenyl)methanone
(3-amino-6-(2,2-difluorocyclopropyl)-1H-pyrazolo[3,4-b]pyridin-1-yl)(2-methoxyphenyl)methanone
(3-amino-6-(2,2-difluorocyclopropyl)-1H-pyrazolo[3,4-b]pyridin-1-yl)(o-tolyl)methanone

[3-amino-6-[rac-(1R,2R)-2-(trifluoromethyl)cyclopropyl]pyrazolo[3,4-b]pyridin-1-yl]-(2-methoxyphenyl)methanone (3-amino-6-((1r,2R,3S)-2,3-dimethylcyclopropyl)-1H-pyrazolo[3,4-b]pyridin-1-yl)(o-tolyl)methanone (3-amino-6-((1r,2R,3S)-2,3-dimethylcyclopropyl)-1H-pyrazolo[3,4-b]pyridin-1-yl)(2-methoxyphenyl)methanone (3-amino-6-(2,2-difluorocyclopropyl)-1H-pyrazolo[3,4-b]pyridin-1-yl)(3-fluoro-2-methoxyphenyl)methanone (3-amino-5-fluoro-6-(pyrrolidin-1-yl)-1H-pyrazolo[3,4-b]pyridin-1-yl)(3-fluoro-2-methoxyphenyl)methanone

[3-amino-6-(2,5-dihydrofuran-3-yl)pyrazolo[3,4-b]pyridin-1-yl]-(3-fluoro-2-methoxyphenyl)methanone rac-(cis)-4-(3-amino-6-cyclopropylpyrazolo[3,4-b]pyridine-1-carbonyl)-3-methylpiperidin-2-one (3-amino-6-cyclopropyl-1H-pyrazolo[3,4-b]pyridin-1-yl)(2-ethylphenyl)methanone (3-amino-6-cyclopropyl-1H-pyrazolo[3,4-b]pyridin-1-yl)(2-(difluoromethoxy)phenyl)methanone (3-amino-6-cyclopropyl-1H-pyrazolo[3,4-b]pyridin-1-yl)(5-methyloxazol-4-yl)methanone (3-amino-6-cyclopropyl-1H-pyrazolo[3,4-b]pyridin-1-yl)(4-methylthiazol-5-yl)methanone (3-amino-6-cyclopropyl-1H-pyrazolo[3,4-b]pyridin-1-yl)(2-methyltetrahydrofuran-3-yl)methanone (3-amino-6-cyclopropyl-1H-pyrazolo[3,4-b]pyridin-1-yl)((2S,3R)-2-methyltetrahydrofuran-3-yl)methanone 3-(3-amino-6-cyclopropyl-1H-pyrazolo[3,4-b]pyridine-1-carbonyl)-2-methylbenzonitrile (3-amino-6-cyclopropyl-1H-pyrazolo[3,4-b]pyridin-1-yl)(tetrahydro-2H-pyran-4-yl)methanone (3-amino-6-cyclopropyl-1H-pyrazolo[3,4-b]pyridin-1-yl)(2-methylpyridin-3-yl)methanone 4-(3-amino-6-cyclopropyl-1H-pyrazolo[3,4-b]pyridine-1-carbonyl)piperidin-2-one (3-amino-6-cyclopropyl-1H-pyrazolo[3,4-b]pyridin-1-yl)(2-methoxy-3-methylphenyl)methanone (3-amino-6-(1-methylcyclopropyl)-1H-pyrazolo[3,4-b]pyridin-1-yl)(o-tolyl)methanone (3-amino-6-(2,2-difluorocyclopropyl)-1H-pyrazolo[3,4-b]pyridin-1-yl)(2-methylpyridin-3-yl)methanone (3-amino-6-(2,2-difluorocyclopropyl)-1H-pyrazolo[3,4-b]pyridin-1-yl)(2-methyltetrahydrofuran-3-yl)methanone (3-amino-6-cyclopropyl-1H-pyrazolo[3,4-b]pyridin-1-yl)(3-chloro-2-methoxyphenyl)methanone 3-(3-amino-6-cyclopropyl-1H-pyrazolo[3,4-b]pyridine-1-carbonyl)-2-methoxybenzonitrile (3-amino-6-cyclopropyl-1H-pyrazolo[3,4-b]pyridin-1-yl)(tetrahydro-2H-pyran-3-yl)methanone (3-amino-6-cyclopropyl-1H-pyrazolo[3,4-b]pyridin-1-yl)(3-methylpyrazin-2-yl)methanone (3-amino-6-cyclopropyl-1H-pyrazolo[3,4-b]pyridin-1-yl)(2-methoxypyridin-3-yl)methanone (3-amino-6-cyclopropyl-1H-pyrazolo[3,4-b]pyridin-1-yl)(2-chloropyridin-3-yl)methanone (3-amino-6-cyclopropyl-1H-pyrazolo[3,4-b]pyridin-1-yl)(2-(trifluoromethyl)pyridin-3-yl)methanone (3-amino-6-cyclopropyl-1H-pyrazolo[3,4-b]pyridin-1-yl)(3-methylpyridazin-4-yl)methanone (3-amino-6-cyclopropyl-1H-pyrazolo[3,4-b]pyridin-1-yl)(3-methylisothiazol-4-yl)methanone

[3-amino-6-[(1R,4S)-3-azabicyclo[2.2.1]heptan-3-yl]pyrazolo[3,4-b]pyridin-1-yl]-(2-methoxyphenyl)methanone (3-amino-6-cyclopropyl-1H-pyrazolo[3,4-b]pyridin-1-yl)((2R,3S)-3-methyltetrahydrofuran-2-yl)methanone

[3-amino-6-(7-azabicyclo[2.2.1]heptan-7-yl)pyrazolo[3,4-b]pyridin-1-yl]-(2-methoxyphenyl)methanone Particular compounds of formula I of the present invention are those selected from the group consisting of:

(3-amino-6-cyclopropylpyrazolo[3,4-b]pyridin-1-yl)-(2-methoxyphenyl)methanone 2,2,2-trifluoroacetic acid (3-amino-6-cyclopropylpyrazolo[3,4-b]pyridin-1-yl)-(2-methylphenyl)methanone

[3-amino-6-(cyclopenten-1-yl)pyrazolo[3,4-b]pyridin-1-yl]-(2-methoxyphenyl)methanone (3-amino-6-(trifluoromethyl)-1H-pyrazolo[3,4-b]pyridin-1-yl)(2-methoxyphenyl)methanone

[3-amino-6-(cyclopenten-1-yl)pyrazolo[3,4-b]pyridin-1-yl]-(2-methylphenyl)methanone (3-amino-6-cyclobutyl-1H-pyrazolo[3,4-b]pyridin-1-yl)(2-methoxyphenyl)methanone (3-amino-6-((1RS,2RS)-2-methylcyclopropyl)-1H-pyrazolo[3,4-b]pyridin-1-yl)(o-tolyl)methanone (3-amino-6-((1RS,2RS)-2-methylcyclopropyl)-1H-pyrazolo[3,4-b]pyridin-1-yl)(2-methoxyphenyl)methanone (3-amino-6-(2,2-difluorocyclopropyl)-1H-pyrazolo[3,4-b]pyridin-1-yl)(2-methoxyphenyl)methanone (3-amino-6-((1r,2R,3S)-2,3-dimethylcyclopropyl)-1H-pyrazolo[3,4-b]pyridin-1-yl)(2-methoxyphenyl)methanone

[3-amino-6-(2,5-dihydrofuran-3-yl)pyrazolo[3,4-b]pyridin-1-yl]-(3-fluoro-2-methoxyphenyl)methanone (3-amino-6-cyclopropyl-1H-pyrazolo[3,4-b]pyridin-1-yl)(2-methylpyridin-3-yl)methanone (3-amino-6-(2,2-difluorocyclopropyl)-1H-pyrazolo[3,4-b]pyridin-1-yl)(2-methylpyridin-3-yl)methanone 3-(3-amino-6-cyclopropyl-1H-pyrazolo[3,4-b]pyridine-1-carbonyl)-2-methoxybenzonitrile (3-amino-6-cyclopropyl-1H-pyrazolo[3,4-b]pyridin-1-yl)(2-methoxypyridin-3-yl)methanone (3-amino-6-cyclopropyl-1H-pyrazolo[3,4-b]pyridin-1-yl)(2-chloropyridin-3-yl)methanone In another embodiment, the present invention provides a compound according to formula I or I' as described herein for use as a therapeutically active substance.

In yet another embodiment, the present invention provides a compound according to formula I, I', I" or II as described herein for the treatment, prevention and/or delay of progression of, more particularly for the treatment of Cancer in particular Lung Aenocarcinoma, Melanoma, Pancreatic Adenocarcinoma, Head and Neck Squamous Cell Carcinoma, Lung Squamous Cell Carcinoma, Esophageal Carcinoma, Glioblastoma Multiforme, and Mesothelioma, more particularly Lung Adenocarcinoma, Lung Squamous Carcinoma, Pancreatic Adenocarcinoma, Glioblastoma Multiforme, and Head and Neck Squamous Carcinoma.

In another embodiment, the present invention provides the use of a compound according to formula I or I' as described herein for the preparation of a medicament for the treatment, prevention and/or delay of progression of, more particularly for the treatment of, Cancer in particular Lung Aenocarcinoma, Melanoma, Pancreatic Adenocarcinoma, Head and Neck Squamous Cell Carcinoma, Lung Squamous Cell Carcinoma, Esophageal Carcinoma, Glioblastoma Multiforme, and Mesothelioma, more particularly Lung Adenocarcinoma, Lung Squamous Carcinoma, Pancreatic Adenocarcinoma, Glioblastoma Multiforme, and Head and Neck Squamous Carcinoma.

In one aspect, the application provides a method of treating a Mat2A disorder in a subject having Mat2A related disorders, said method comprising administering to a subject in need thereof a therapeutically effective amount of any of the above compounds.

In another embodiment, the present invention provides a method of the treatment, prevention and/or delay of progression of, more particularly of the treatment of, Cancer in particular Lung Aenocarcinoma, Melanoma, Pancreatic Adenocarcinoma, Head and Neck Squamous Cell Carcinoma, Lung Squamous Cell Carcinoma, Esophageal Carcinoma, Glioblastoma Multiforme, and Mesothelioma, more particularly Lung Adenocarcinoma, Lung Squamous Carcinoma, Pancreatic Adenocarcinoma, Glioblastoma Multiforme, and Head and Neck Squamous Carcinoma which comprises administering an effective amount of a compound according to formula I or I' as described herein.

In particular embodiment, the present invention provides a method of treatment, prevention and/or delay of progression of, more particularly of the treatment of, Cancer in particular Lung Aenocarcinoma, Melanoma, Pancreatic Adenocarcinoma, Head and Neck Squamous Cell Carcinoma, Lung Squamous Cell Carcinoma, Esophageal Carcinoma, Glioblastoma Multiforme, and Mesothelioma, more particularly Lung Adenocarcinoma, Lung Squamous Carcinoma, Pancreatic Adenocarcinoma, Glioblastoma Multiforme, and Head and Neck Squamous Carcinoma which comprises administering an effective amount of a compound according to formula I or I' as described herein.

In particular, Mat2A disorders or Mat2A related diseases are Cancer in particular Lung Aenocarcinoma, Melanoma, Pancreatic Adenocarcinoma, Head and Neck Squamous Cell Carcinoma, Lung Squamous Cell Carcinoma, Esophageal Carcinoma, Glioblastoma Multiforme, and Mesothelioma, more particularly Lung Adenocarcinoma, Lung Squamous Carcinoma, Pancreatic Adenocarcinoma, Glioblastoma Multiforme, and Head and Neck Squamous Carcinoma.

In one aspect, the application provides a pharmaceutical composition comprising the compound of any one of the above embodiments, admixed with at least one pharmaceutically acceptable carrier, such as excipient or diluent.

In another embodiment, the present invention provides a use of a compound of formula I or I' in the preparation of a medicament for the treatment, prevention and/or delay of progression of, more particularly for the treatment of, diseases associated with Mat2A.

In yet another embodiment, the present invention provides a medicaments containing a compound of formula I or I' as defined herein or a pharmaceutically acceptable salt thereof and a therapeutically inert carrier are also an object of the present invention, as is a process for their production, which comprises bringing one or more compounds of formula I or I' and/or pharmaceutically acceptable acid addition salts and, if desired, one or more other therapeutically valuable substances into a galenical administration form together with one or more therapeutically inert carriers.

Another embodiment provides pharmaceutical compositions or medicaments comprising the compounds of the invention and a therapeutically inert carrier, diluent or pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. For example, such amount may be below the amount that is toxic to normal cells, or the mammal as a whole.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, coated tablets, dragées, powders, capsules (hard and soft gelatine capsules), solutions (i.e. injection solutions), dispersions, suspensions, syrups, sprays, suppositories, gels, emulsions, patches, eye drops, ear drops etc. Such compositions may contain components conventional in pharmaceutical preparations, e.g., diluents, carriers, pH modifiers, sweeteners, bulking agents, and further active agents.

A typical formulation is prepared by mixing a compound of the present invention and pharmaceutically acceptable carrier or excipient. Suitable pharmaceutically acceptable carriers and excipients are well known to those skilled in the art and are described in detail in, e.g., Ansel, Howard C., et al., *Ansel's Pharmaceutical Dosage Forms and Drug Delivery Systems*. Philadelphia: Lippincott, Williams & Wilkins, 2004; Gennaro, Alfonso R., et al. *Remington: The Science and Practice of Pharmacy*. Philadelphia: Lippincott, Williams & Wilkins, 2000; and Rowe, Raymond C. *Handbook of Pharmaceutical Excipients*. Chicago, Pharmaceutical Press, 2005. The pharmaceutically acceptable carriers may be either solid or liquid. Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatin, tragacanth, methylcellulose, sodium carboxy, methyl, cellulose, a low melting wax, cocoa butter, and the like.

The dosage at which compounds of the invention can be administered can vary within wide limits and will, of course, be fitted to the individual requirements in each particular case. In general, in the case of oral administration a daily dosage of about 0.01 to 1000 mg per person of a compound formula I or I' should be appropriate, although the above upper limit can also be exceeded when necessary.

An example of a suitable oral dosage form is a tablet comprising about 100 mg to 500 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution may be filtered, e.g., using a 0.2 μm filter, to remove impurities and contaminants.

An embodiment, therefore, includes a pharmaceutical composition comprising a compound according to the invention herein described, or a stereoisomer thereof. In a further embodiment includes a pharmaceutical composition comprising a compound according to the invention herein described, or a stereoisomer thereof, together with a pharmaceutically acceptable carrier or excipient.

The compounds of the present invention can be used, either alone or in combination with other drugs, for the treatment, prevention and/or delay of progression of Mat2A related diseases, in particular Cancer in particular Lung Aenocarcinoma, Melanoma, Pancreatic Adenocarcinoma, Head and Neck Squamous Cell Carcinoma, Lung Squamous Cell Carcinoma, Esophageal Carcinoma, Glioblastoma Multiforme, and Mesothelioma, more particularly Lung Adenocarcinoma, Lung Squamous Carcinoma, Pancreatic Adenocarcinoma, Glioblastoma Multiforme, and Head and Neck Squamous Carcinoma.

A particular embodiment of the present invention relates to pharmaceutical compositions comprising compounds of formula I or I' or their pharmaceutically acceptable salts as defined above and one or more pharmaceutically acceptable excipients for use in the treatment, prevention and/or delay of progression of cognitive impairments associated with Cancer in particular Lung Aenocarcinoma, Melanoma, Pancreatic Adenocarcinoma, Head and Neck Squamous Cell Carcinoma, Lung Squamous Cell Carcinoma, Esophageal Carcinoma, Glioblastoma Multiforme, and Mesothelioma, more particularly Lung Adenocarcinoma, Lung Squamous Carcinoma, Pancreatic Adenocarcinoma, Glioblastoma Multiforme, and Head and Neck Squamous Carcinoma.

Another embodiment includes a pharmaceutical composition comprising a compound according to the invention herein described for use in the treatment, prevention and/or delay of progression of, more particularly in the treatment of a Mat2A related diseases. Another embodiment includes a pharmaceutical composition comprising a compound according to the invention herein described for use in the treatment, prevention and/or delay of progression of, more particularly in the treatment of Mat2A related diseases.

In another embodiment the present invention provides the manufacture of compounds of formula I or I' as described herein.

The preparation of compounds of formula I or I' of the present invention may be carried out in sequential or convergent synthetic routes. Syntheses of the invention are shown in the following general scheme. The skills required for carrying out the reaction and purification of the resulting products are known to those persons skilled in the art. In case a mixture of enantiomers or diastereoisomers is produced during a reaction, these enantiomers or diastereoisomers can be separated by methods described herein or known to the man skilled in the art such as e.g. chiral chromatography or crystallization.

Furthermore the compounds of the present invention can be prepared from commercially available starting materials or by the use of general synthetic techniques and procedures that are known to those skilled in the art. Outlined below are reaction schemes suitable for the preparation of such compounds. The substituents and indices used in the following description of the processes have the significance given herein. Further exemplification can be found in the specific examples detailed below.

General Schemes

In more detail, compounds of formula I or I' and their intermediates may be prepared by schemes 1 to 2 and by the description of the specific examples.

A subgroup of compounds of formula I or I' wherein $X^1$ is $CR^3$, $R^4$ is H, and $R^1$, $R^2$ and $R^3$ are as defined previously, can be prepared as outlined in scheme 1 below.

Scheme 1

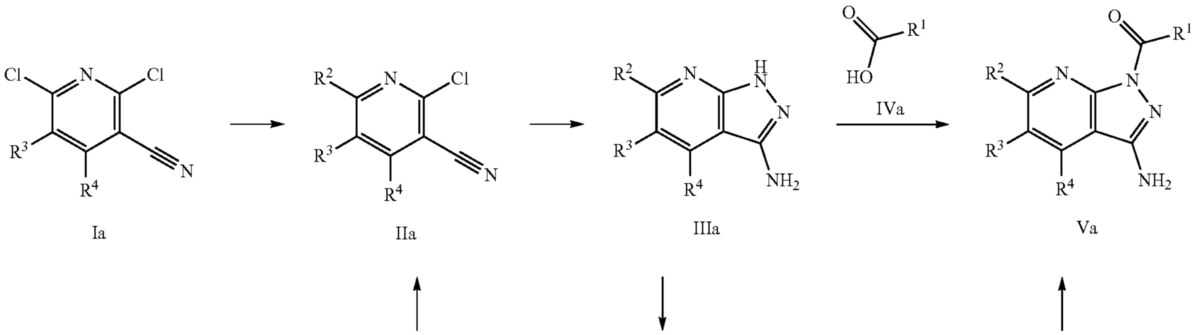

Ia IIa IIIa Va

-continued

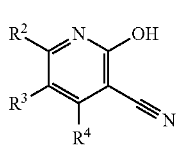

IXa

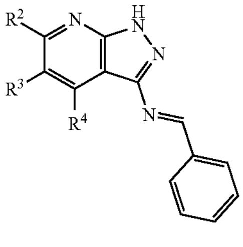

VIa

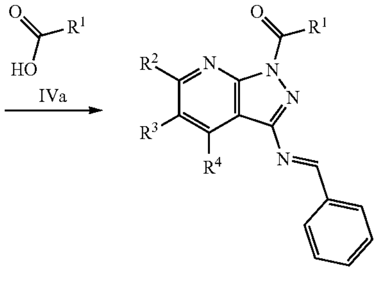

VIIa

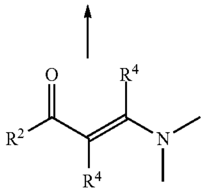

VIIIa

Chloropyridines IIa are reacted with excess hydrazine in polar solvents (e.g. Ethanol, ethylene glycol) (Canadian Journal of Chemistry, 1988, 420) to form aminopyrazoles IIIa. These are then selectively coupled with carboxylic acids IVa employing mild activating agents (e.g. 1,1'-carbonyldiimidazole) in polar solvents (e.g. DMF, DMA, NMP) at elevated temperatures (80-120° C.). Alternatively, pyrazole IIIa can be protected as the bezaldehyde-imine (VIa) by reaction with benzaldehyde in ethanol at elevated temperatures and subsequently reacted with carboxylic acid IVa, activated with more reactive coupling agents (e.g. HATU, TBTU) under basic conditions (e.g. $iPr_2NEt$, $Et_3N$) in polar solvents (e.g. DMF, DMA) at ambient temperature or gently warmed (50° C.) to afford protected products VIIa. The imine can be readily hydrolysed under mild acidic conditions (e.g. formic acid or 1N HCl) to afford final products IIIa.

Chloropyridine IIa can be synthesized from a 2,6-dihalo-3-nitrile pyridine VIIa by reacting in the 6-position with a boronic acid or boronic ester in a Suzuki-Miyaura type reaction using palladium catalyst such as $Pd(dppf)_2Cl_2$—$CH_2Cl_2$ or and an excess of a base such as $K_2CO_3$ or $Na_2CO_3$ at elevated temperatures (80-100° C.) in solvents such as dioxane and water or alternatively with an amine in a SnAr type reaction at elevated temperatures (>70° C.) in polar solvents (e.g. THF, EtOH, DMF, DMA, NMP) using an excess of a base (e.g. DIPEA, TEA, $K_2CO_3$).

Alternatively, pyridine IIa can be synthesized by cyclizing the intermediate VIIIa with 2-cyanoacetamide using base (e.g. NaOEt) in polar solvents such as DMF at elevated temperatures yielding corresponding hydroxy pyridine IXa. Hydroxy pyridine IXa can be converted to pyridine Ta with dehydrating reagent such as $POCl_3$ at elevated temperatures.

General Procedures

General Procedure A: Suzuki-Miyaura Type Cross Coupling

To a 2,6-dihalo-3-nitrile pyridine dissolved in dioxane/water (ration 4:1, 0.1-0.2 M) were added $K_2CO_3$ or $Na_2CO_3$ (3 eq.) followed by boronic acid or ester (1.5 eq.) and the resulting reaction mixture was degassed by bubbling argon through the mixture with sonication. $Pd(dppf)_2Cl_2 \cdot CH_2Cl_2$ complex or tetrakis(triphenylphosphine)palladium (0.05-0.2 eq.) was added and the reaction mixture heated to 100° C. until LCMS showed complete consumption of the pyridine starting material (0.5 h-16 h). The reaction was then diluted with EtOAc, washed with brine, dried over $Na_2SO_4$ and concentrated. The crude product could be purified using flash silica gel chromatography.

General Procedure B: SnAr Reaction

To a solution of a 2,6-dihalo-3-nitrile pyridine in THF or DMF (0.1-0.2 M) were added DIPEA or TEA (2 eq.) and a secondary amine (1.1 eq.). Reaction was stirred at ambient or elevated temperature until LCMS showed complete consumption of the pyridine starting material (up to 24 h). The reaction was then diluted with EtOAc, washed with brine, dried over $Na_2SO_4$ and concentrated. The crude product could be purified using flash silica gel chromatography.

General Procedure C: Hydrazine Cyclisation

To a solution/suspension of requisite chloropyridine in ethanol or ethylene glycol (0.1-0.2 M) was added hydrazine (2 eq.) and the reaction stirred at 70°-120° C. until LCMS showed complete consumption of the chloropyridine (up to 16 h). The reaction was concentrated and the crude product purified using flash silica gel chromatography or simply suspended in water and isolated by filtration.

General Procedure D: Pyridone Synthesis

To a crude solution of the appropriate ene-one VIII in DMF (0.2-0.4 M) (prepared by a modified procedure from J. Med. Chem. 2011, 54, 7974) were added 2-cyanoacetamide (3 eq.) and NaOEt (3 eq.) as a base. The resulting reaction mixture was heated to 100° C. until LCMS showed complete consumption of the starting material VIII (approx. 16 h). The reaction was then diluted with EtOAc, washed with brine, dried over $Na_2SO_4$ and concentrated. The crude product could be purified using flash silica gel chromatography.

General Procedure E: Pyridylchloride Synthesis

Hydroxypyridine was dissolved in $POCl_3$ (10-20 eq.) and the resulting reaction mixture was heated to 100° C. until LCMS showed complete reaction (approx. 16 h). The reaction mixture was then concentrated under reduced pressure, diluted with EtOAc and filtered. The organic layers were diluted with water and extracted several times with EtOAc.

The combined organic layers were washed with brine, dried ($Na_2SO_4$) and concentrated. The crude chloro pyridine product could be purified using flash silica gel chromatography.

General Procedure F1: Amide Coupling with CDI

As described in Journal of Enzyme Inhibition and Medicinal Chemistry, 2013, 1088. To a solution of the appropriate carboxylic acid (1.5 eq) dissolved in DMF (0.1-0.2 M) is added carbonyldiimidazole (1.5 eq) and the mixture stirred at ambient temperature for 0.5-1 h before the requisite pyrazolo[3,4-b]pyridin-3-amine (1 eq.) is added and the mixture heated to 100° C.-140° C. until LCMS shows complete reaction (24 h-48 h). The reaction was then concentrated to dryness and the product purified by reversed phase preparative HPLC.

General Procedure F2: Amide Coupling with 2-(1H-Benzotriazole-1-yl)-1,1,3,3-Tetramethylaminium Tetrafluoroborate (TBTU) and Benzimine Deprotection To a solution of the appropriate carboxylic acid (1.1 eq) dissolved in DMF (0.1-0.2 M) is added TBTU (1.1 eq) and triethylamine (2 eq.) followed by (E)-N-(6-cyclopropyl-1H-pyrazolo[3,4-b]pyridin-3-yl)-1-phenylmethanimine (1 eq.) and the mixture stirred at ambient temperature until LCMS shows complete reaction (16 h-48 h) or heated to 50° C. to accelerate completion. A drop of 1N HCl (aqueous) is then added and the reaction stirred for 1 h at ambient temperature. The reaction was then concentrated to dryness and the product purified by reversed phase preparative HPLC.

A particular embodiment of the invention relates to a process for the preparation of compounds of formula (I') wherein $X^1$, $R^1$ and $R^2$ are as defined herein and pharmaceutically acceptable salts thereof as defined in accordance with the present invention, comprising coupling compound of formula (III) with carboxylic acids IVa employing mild activating agents (e.g. 1,1'-carbonyldiimidazole) in polar solvents (e.g. DMF, DMA, NMP) at elevated temperatures (80-120° C.) to afford the compound of formula (I), as shown in scheme 2.

Scheme 2

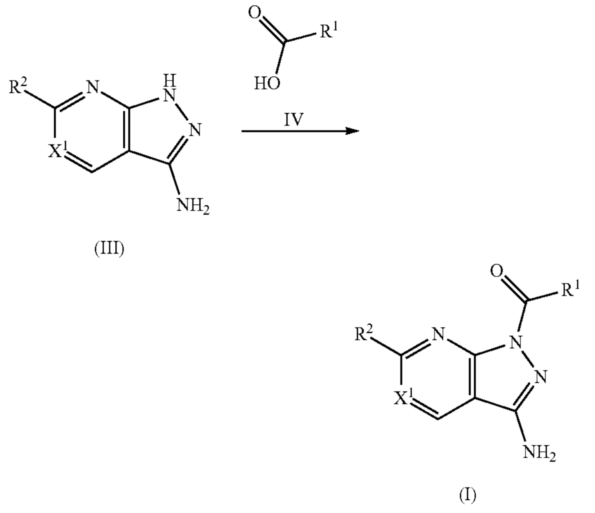

(III)

(I)

The compounds were investigated in accordance with the test given hereinafter.

Determination of Mat2A Activity

Measurement of Mat2A inhibition is performed in 384 well format absorbance-based assay.

Recombinant human Mat2a (12.5 nM) and serial diluted compounds in DMSO (range of concentrations from 10 μM to 508 μM) or controls (DMSO) are incubated for 15 minutes at room temperature (RT) in assay buffer containing 50 mM HEPES pH 7.5, 50 mM KCl, 50 mM MgCl2, 0.01% Tween 20 and 10 mM DTT. The reaction is initiated by the addition of the combined substrates ATP and Methionine, each at a final concentration of 100 μM. Final assay condition are 12.5 nM Mat2A, 100 μM ATP and Methionine Substrates and 2% DMSO. After 120 minutes of incubation at RT, the reaction is stopped by the addition of Biomol Green. The absorbance signal is measured at λ=635 nm with a multiplate reader (BMG Pherastar reader or equivalent) after 30 min of equilibration at RT.

| Example number | MAT2A IC50 (uM) |
|---|---|
| 1 | 0.092 |
| 2 | 0.11 |
| 3 | 0.053 |
| 4 | 0.14 |
| 5 | 0.094 |
| 6 | 0.11 |
| 7 | 0.12 |
| 8 | 0.056 |
| 9 | 0.39 |
| 10 | 0.28 |
| 11 | 0.066 |
| 12 | 0.14 |
| 13 | 0.11 |
| 14 | 0.095 |
| 15 | 0.099 |
| 16 | 0.065 |
| 17 | 0.28 |
| 18 | 0.35 |
| 19 | 0.41 |
| 20 | 0.16 |
| 21 | 0.14 |
| 22 | 0.44 |
| 23 | 0.02 |
| 24 | 0.3 |
| 25 | 0.29 |
| 26 | 0.12 |
| 27 | 0.069 |
| 28 | 0.34 |
| 29 | 0.48 |
| 30 | 0.053 |
| 31 | 0.2 |
| 32 | 0.059 |
| 33 | 0.028 |
| 34 | 0.029 |
| 35 | 0.017 |
| 36 | 0.067 |
| 37 | 0.29 |
| 38 | 0.12 |
| 39 | 0.064 |
| 40 | 0.032 |
| 41 | 0.15 |
| 42 | 0.2 |
| 43 | 0.035 |
| 44 | 0.013 |
| 45 | 0.091 |
| 46 | 0.055 |
| 47 | 0.025 |
| 48 | 0.13 |
| 49 | 0.022 |
| 50 | 0.16 |
| 51 | 0.17 |
| 52 | 0.035 |
| 53 | 0.24 |
| 54 | 0.21 |
| 55 | 0.32 |
| 56 | 0.43 |
| 57 | 0.11 |
| 58 | 0.3 |
| 59 | 0.033 |
| 60 | 0.037 |

-continued

| Example number | MAT2A IC50 (uM) |
|---|---|
| 61 | 0.13 |
| 62 | 0.35 |
| 63 | 0.13 |
| 64 | 0.041 |
| 65 | 0.036 |
| 66 | 0.054 |
| 67 | 0.049 |
| 68 | 0.019 |
| 69 | 0.079 |
| 70 | 0.18 |
| 71 | 0.48 |
| 72 | 0.037 |
| 73 | 0.18 |
| 74 | 0.22 |
| 75 | 0.026 |
| 76 | 0.017 |
| 77 | 0.031 |
| 78 | 0.2 |
| 79 | 0.15 |

Abbreviations

The following abbreviations were used in the experimental part:

Ar=argon;
nBuLi=n-butyl lithium;
DCM=dichloromethane;
DIPEA=diisopropylethylamine;
DMSO=dimethylsufoxide;
DMF=dimethylformamide;
EtOH=ethanol;
EtOAc=ethyl acetate;
HCl=hydrochloric acid;
HPLC=high peformance liquid chromatography;
LDA=lithium diisopropylamide;
LiHMDS=lithium bis (trimethylsilyl)amide;
mCPBA=metachloroperbenzoic acid;
MOM=methoxymethyl;
NMP=N-methyl-2-pyrolidone;
SEM=[2-(trimethylsilyl)ethoxy)methyl] acetal;
TBTU=2-(1H-Benzotriazole-1-yl)-1,1,3,3-tetramethylaminium tetrafluoroborate;
THF=tetrahydrofuran;
TEMPO=2,2,6,6-tetramethylpiperidinyloxyl;
TBAF=tetra-n-butyl ammonium fluorideTLC=thin layer chromatography;

Starting Materials

Basic chemicals and solvents were purchased and used as is without further purification. Some intermediates are commercially available, or they can be synthesized using methods known in the art.

INTERMEDIATES

Intermediate 1: 6-phenyl-1H-pyrazolo[3,4-b]pyridin-3-amine

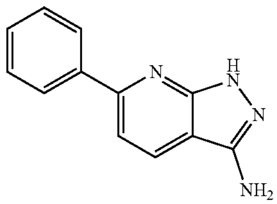 [SMILES: Nc1n[nH]c2nc(-c3ccccc3)ccc12]

The titled compound ([M+H]$^+$ 211.1) was prepared from 2-chloro-6-phenylnicotinonitrile (CN106146493A) and hydrazine at 70° C. in accordance with General procedure C.

Intermediate 2: 6-isobutyl-1H-pyrazolo[3,4-b]pyridin-3-amine

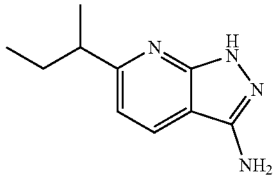

Step 1: 2-chloro-6-isobutylnicotinonitrile 2,6-dichloronicotinonitrile (250 mg, 1.45 mmol) was dissolved in dioxane (5 ml) and 2-methylpropylzinc bromide (3.47 ml, 0.5M in THF, 1.73 mmol) was added and the reaction mixture was sparged with argon. Pd(dppf)$_2Cl_2 \cdot CH_2Cl_2$ complex (12 mg, 15 μmol) was added and the reaction was heated to 90° C. in a sealed tube for 18 h after which time a second portion of 2-methylpropylzinc bromide (3.47 ml, 0.5M in THF, 1.73 mmol) and Pd(dppf)$_2Cl_2$—$CH_2Cl_2$ complex (12 mg, 15 μmol) was added and the reaction heated for a further 2 h at 70° C. The reaction was concentrated to dryness and the residue purified by flash silica gel chromatography (Ethylacetate: n-Heptane 0:1-1:0) to afford the title compound (185 mg, 76%) as a colourless oil. ([M+H,Cl]$^+$195.1)

Step 2: 6-isobutyl-1H-pyrazolo[3,4-b]pyridin-3-amine

The title compound ([M+H]$^+$ 191.3) was prepared from 2-chloro-6-isobutylnicotinonitrile (step 1) and hydrazine at 70° C. in accordance with General procedure C.

Intermediate 3: 6-(pyrrolidin-1-yl)-1H-pyrazolo[3,4-b]pyridin-3-amine

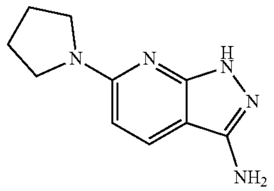 [SMILES: Nc1n[nH]c2nc(N3CCCC3)ccc12]

Step 1: 2-chloro-6-(pyrrolidin-1-yl)nicotinonitrile

The title compound ([M+H]$^+$ 208.1) was prepared from 2,6-dichloronicotinonitrile and pyrrolidine in THF and DIPEA as base in accordance with General procedure B.

Step 2: 6-(pyrrolidin-1-yl)-1H-pyrazolo[3,4-b]pyridin-3-amine

The title compound ([M+H]$^+$ 204.2) was prepared from 2-chloro-6-(pyrrolidin-1-yl)nicotinonitrile (step 1) and hydrazine at 100° C. in accordance with General procedure C and isolated by filtration from water.

Intermediate 4: 6-(cyclohexen-1-yl)-1H-pyrazolo[3,4-b]pyridin-3-amine

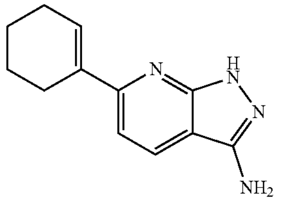 [SMILES: Nc1n[nH]c2nc(C3=CCCCC3)ccc12]

Step 1: 2-chloro-6-(cyclohex-1-en-1-yl)nicotinonitrile

The title compound ([M+H, Cl]$^+$219.1) was prepared from 2,6-dichloronicotinonitrile and cyclohex-1-en-1-ylboronic acid under tetrakis(triphenylphosphine)palladium catalysis at 110° C. in accordance with General procedure A.

Step 2: 6-(cyclohexen-1-yl)-1H-pyrazolo[3,4-b]pyridin-3-amine

The title compound ([M+H]$^+$ 215.2) was prepared from 2-chloro-6-(cyclohex-1-en-1-yl)nicotinonitrile (step 1) and hydrazine at 100° C. in accordance with General procedure C.

Intermediate 5: cyclopropyl-1H-pyrazolo[3,4-b]pyridin-3-amine

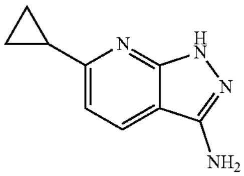 [SMILES: Nc1n[nH]c2nc(C3CC3)ccc12]

The title compound ([M+H]$^+$ 175.4) was prepared from 2-chloro-6-cyclopropylnicotinonitrile (38041-19-9) and hydrazine at 100° C. in accordance with General procedure C.

Intermediate 6: 5-fluoro-6-phenyl-1H-pyrazolo[3,4-b]pyridin-3-amine

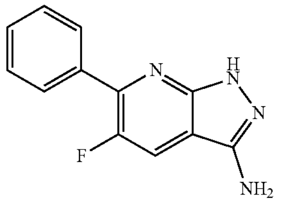 [SMILES: Nc1n[nH]c2nc(-c3ccccc3)c(F)cc12]

Step 1: 2-chloro-5-fluoro-6-phenylnicotinonitrile

The title compound ([M+H+MeCN, Cl]$^+$275.1) was prepared from 2,6-dichloro-5-fluoronicotinonitrile and phenylboronic acid under $Pd(dppf)_2Cl_2$—$CH_2Cl_2$ complex catalysis at 90° C. in accordance with General procedure A.

Step 2: 6-(cyclohexen-1-yl)-1H-pyrazolo[3,4-b]pyridin-3-amine

The title compound ([M+H]$^+$ 229.3) was prepared from 2-chloro-5-fluoro-6-phenylnicotinonitrile (step 1) and hydrazine at 75° C. in accordance with General procedure C.

Intermediate 7: 5-Fluoro-6-pyrrolidin-1-yl-1H-pyrazolo[3,4-b]pyridin-3-ylamine

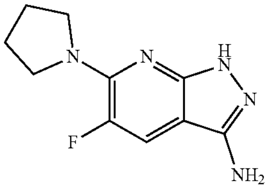 [SMILES: Nc1n[nH]c2nc(N3CCCC3)c(F)cc12]

To a solution of 2,6-dichloro-5-fluoro-3-pyridine-carbonitrile (200 mg, 1 mmol) in ethanol (2 ml) was added pyrrolidine (124 ul, 0.2 mmol) and the reaction heated to 95° C. for 6 h. The reaction was concentrated and the residue redissolved in ethylene glycol (2 ml) and hydrazine monohydrate (0.75 ml, 15.0 mmol)) was added and the reaction mixture heated to 130° C. for 3 h. The reaction was absorbed onto silica gel and purified by flash silica gel column chromatography (Ethylacetate: n-Heptane 0:1-1:0) to afford the title compound (149 mg, 68%) as a white solid. ([M+H]$^+$ 222.1)

Intermediate 8: 6-(3,3-difluoroazetidin-1-yl)-5-fluoro-1H-pyrazolo[3,4-b]pyridin-3-amine

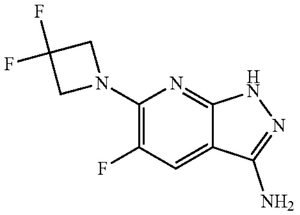 [SMILES: Nc1n[nH]c2nc(N3CC(F)(F)C3)c(F)cc12]

Step 1: 2-chloro-6-(3,3-difluoroazetidin-1-yl)-5-fluoronicotinonitrile

The title compound was prepared from 2,6-dichloro-5-fluoronicotinonitrile and 3,3-difluoroazetidine hydrochloride in DMF using triethylamine as abased in accordance with General procedure B. $^1H$ NMR (DMSO-d6, 300 MHz) δ 8.18 (d, 1H, J=11.3 Hz), 4.70 (dt, 4H, J=1.8, 12.4 Hz)

Step 2: 6-(3,3-difluoroazetidin-1-yl)-5-fluoro-1H-pyrazolo[3,4-b]pyridin-3-amine The title compound ([M+H]$^+$ 244.1) was prepared from 2-chloro-5-fluoro-6-phenylnicotinonitrile (step 1) and hydrazine in ethylene glycol at 120° C. in accordance with General procedure C.

Intermediate 9: 6-(pyrrolidin-1-yl)-1H-pyrazolo[3,4-d]pyrimidin-3-amine

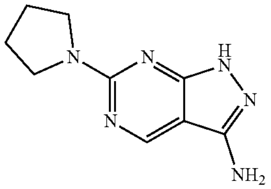 [SMILES: Nc1n[nH]c2nc(N3CCCC3)ncc12]

Step 1: 4-chloro-2-(pyrrolidin-1-yl)pyrimidine-5-carbonitrile

The title compound ([M+H, Cl]$^+$209.1) was prepared from 2,4-dichloropyrimidine-5-carbonitrile and pyrrolidine in THF and DIPEA as base in accordance with General procedure B.

Step 2: 6-(pyrrolidin-1-yl)-1H-pyrazolo[3,4-d]pyrimidin-3-amine

The title compound ([M+H]$^+$ 205.2) was prepared from 4-chloro-2-(pyrrolidin-1-yl)pyrimidine-5-carbonitrile (step 1) and hydrazine in ethanol at 100° C. in accordance with General procedure C.

Intermediate 10: 6-(pyrrolidin-1-yl)-1H-pyrazolo[3,4-d]pyrimidin-3-amine

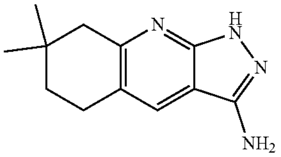 [SMILES: CC1(C)CCc2cc3c(N)n[nH]c3nc2C1]

The title compound ([M+H]$^+$ 217.2) was prepared from 2-chloro-7,7-dimethyl-5,6,7,8-tetrahydroquinoline-3-carbonitrile and hydrazine in ethanol at 100° C. in accordance with General procedure C.

Intermediate 11: 6-(3,4-dihydro-2H-pyran-6-yl)-1H-pyrazolo[3,4-b]pyridin-3-amine

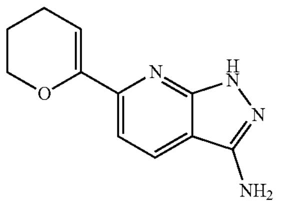 [SMILES: Nc1n[nH]c2nc(C3=CCCCO3)ccc12]

Step 1: 2-chloro-6-(3,4-dihydro-2H-pyran-6-yl)nicotinonitrile

The title compound ([M+H, Cl]$^+$221.1) was prepared from 2,6-dichloro-5-fluoronicotinonitrile and 2-(3,4-dihydro-2H-pyran-6-yl)-4,4,5,5-tetramethyl-1,3,2-dioxaborolane under tetrakis(triphenylphosphine)palladium catalysis at 90° C. in accordance with General procedure A.

Step 2: 6-(3,4-dihydro-2H-pyran-6-yl)-1H-pyrazolo[3,4-b]pyridin-3-amine

The title compound ([M+H]$^+$ 217.1) was prepared from 2-chloro-6-(3,4-dihydro-2H-pyran-6-yl)nicotinonitrile (step 1) and hydrazine in ethanol at 100° C. in accordance with General procedure C.

Intermediate 12: 6-(cyclopenten-1-yl)-1H-pyrazolo[3,4-b]pyridin-3-amine

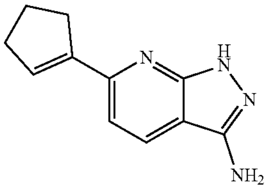 [SMILES: Nc1n[nH]c2nc(C3=CCCC3)ccc12]

Step 1: 2-chloro-6-(cyclopent-1-en-1-yl)nicotinonitrile

The title compound ([M+H, Cl]$^+$205.1) was prepared from 2,6-dichloro-5-fluoronicotinonitrile and cyclopent-1-en-1-ylboronic acid under tetrakis(triphenylphosphine)palladium catalysis at 90° C. in accordance with General procedure A.

Step 2: 6-(cyclopenten-1-yl)-1H-pyrazolo[3,4-b]pyridin-3-amine

The title compound ([M+H]$^+$ 201.1) was prepared from 2-chloro-6-(cyclopent-1-en-1-yl)nicotinonitrile (step 1) and hydrazine in ethanol at 100° C. in accordance with General procedure C.

Intermediate 13: 6-(azetidin-1-yl)-1H-pyrazolo[3,4-b]pyridin-3-amine

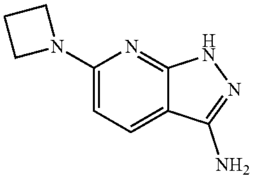 [SMILES: Nc1n[nH]c2nc(N3CCC3)ccc12]

6-bromo-1H-pyrazolo[3,4-b]pyridin-3-amine (100 mg, 0.5 mmol) was dissolved in azetidine (0.5 mL, 12.5 mmol) and stirred at 70° C. for 72 h in a sealed tube. The reaction mixture was poured onto water, the resulting precipitate was filtered, and the filtrate was standing for several days, resulting in crystallisation. Filtration afforded the title compound (12 mg, 13%) as a white solid. ([M+H]$^+$ 190.1)

Intermediate 14: 6-(3,3-difluoroazetidin-1-yl)-1H-pyrazolo[3,4-b]pyridin-3-amine

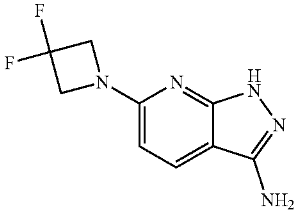

Step 1: 4-chloro-2-(pyrrolidin-1-yl)pyrimidine-5-carbonitrile

The title compound ([M+H, Cl]$^+$230.0) was prepared from 2,6-dichloronicotinonitrile and 3,3-difluoroazetidine hydrochloride in ethanol and DIPEA as base in accordance with General procedure B.

Step 2: 6-(3,3-difluoroazetidin-1-yl)-1H-pyrazolo[3,4-b]pyridin-3-amine

The title compound ([M+H]$^+$ 205.2) was prepared from 4-chloro-2-(pyrrolidin-1-yl)pyrimidine-5-carbonitrile (step 1) and hydrazine in ethanol at 80° C. in accordance with General procedure C.

Intermediate 15: 6-cyclopentyl-1H-pyrazolo[3,4-b]pyridin-3-amine

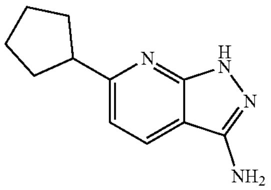

6-(cyclopent-1-en-1-yl)-1H-pyrazolo[3,4-b]pyridin-3-amine (Intermediate 12, step 2) (61 mg, 0.3 mmol) was dissolved in Ethanol (3 ml) and ethyl acetate (1 ml) and 10% palladium on carbon (6 mg, 6 μmol) was added. Then reaction mixture was stirred under a hydrogen-balloon atmosphere at 50° C. for 18 h. The reaction mixture was allowed to cool down to ambient temperature and then filtered over Dicalite® and concentrated to afford the title compound (55 mg, 87%) as a yellow solid. ([M+H]$^+$ 203.1)

Intermediate 16: 6-cyclobutyl-1H-pyrazolo[3,4-b]pyridin-3-amine

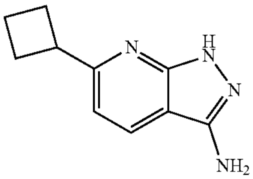

Step 1: 1-cyclobutyl-3-(dimethylamino)prop-2-en-1-one

To a solution of 1-cyclobutylethan-1-one (2.22 ml, 20.4 mmol) in DMF (5 ml) was added 1,1-dimethoxy-N,N-dimethylmethanamine (5.43 ml, 40.8 mmol) and sodium methoxide (50 mg, 0.9 mmol) and the mixture was stirred at 100° C. for 16 h when TH-NMR aliquat of the solution indicated complete conversion. The crude solution was used directly in the next step.

Step 2: 6-cyclobutyl-2-hydroxynicotinonitrile

The title compound ([M+H]$^+$ 175.1) was prepared from 1-cyclobutyl-3-(dimethylamino)prop-2-en-1-one (step 2) and cyanoacetamide in accordance with General procedure D.

Step 3: 2-chloro-6-cyclobutylnicotinonitrile

The title compound ([M+H, Cl]$^+$193.0) was prepared from 6-cyclobutyl-2-hydroxynicotinonitrile (step 2) and $POCl_3$ in accordance with General procedure E.

Step 4: 6-(3,3-difluoroazetidin-1-yl)-1H-pyrazolo[3,4-b]pyridin-3-amine

The title compound ([M+H]$^+$ 189.1) was prepared from 2-chloro-6-cyclobutylnicotinonitrile (step 3) and hydrazine in ethanol at 75° C. in accordance with General procedure C.

Intermediate 17: 6-((1RS,2RS)-2-methylcyclopropyl)-1H-pyrazolo[3,4-b]pyridin-3-amine

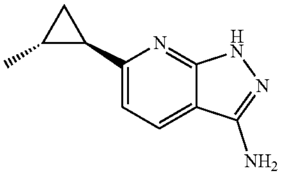

Step 1: 2-hydroxy-6-((1RS,2RS)-2-methylcyclopropyl)nicotinonitrile

The title compound ([M+H]$^+$ 175.0) was prepared by reaction of (E)-3-(dimethylamino)-1-(2-methylcyclopropyl)prop-2-en-1-one (prepared by a modified procedure from J. Med. Chem. 2011, 54, 7974 from 1-(2-methylcyclopropyl)ethanone-CAS: 930-56-3) and 2-cyanoacetamide using NaOMe as a base (General procedure G).

Step 2: 2-chloro-6-((1RS,2RS)-2-methylcyclopropyl)nicotinonitrile

The title compound ([M+H, Cl]$^+$193.1) was prepared by reaction of 2-hydroxy-6-(2-methylcyclopropyl)nicotinonitrile with $POCl_3$ (General procedure H).

Step 3: 6-((1RS,2RS)-2-methylcyclopropyl)-1H-pyrazolo[3,4-b]pyridin-3-amine

The title compound ([M+H]$^+$ 189.1) was prepared from 2-chloro-6-((1RS,2RS)-2-methylcyclopropyl)nicotinonitrile (step 2) and hydrazine in ethanol at 75° C. in accordance with General procedure C.

Intermediate 18: 6-(2,5-dihydrofuran-3-yl)-1H-pyrazolo[3,4-b]pyridin-3-amine

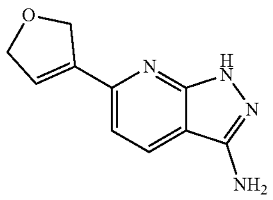 [SMILES: Nc1n[nH]c2nc(C3=CCOC3)ccc12]

The title compound ([M+H]$^+$ 203.1) was prepared from 6-bromo-1H-pyrazolo[3,4-b]pyridin-3-amine and 2-(2,5-dihydrofuran-3-yl)-4,4,5,5-tetramethyl-1,3,2-dioxaborolane under tetrakis(triphenylphosphine)palladium catalysis at 110° C. in accordance with General procedure A.

Intermediate 19: 7-methyl-5,6,7,8-tetrahydro-1H-pyrazolo[3,4-b]quinolin-3-amine

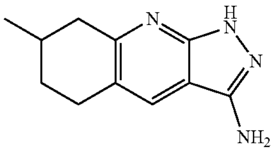

The title compound ([M+H]$^+$ 203.2) was prepared from 2-chloro-7-methyl-5,6,7,8-tetrahydroquinoline-3-carbonitrile and hydrazine in ethanol at 75° C. in accordance with General procedure C.

Intermediate 20: 6-((1RS,2SR)-2-fluorocyclopropyl)-1H-pyrazolo[3,4-b]pyridin-3-amine

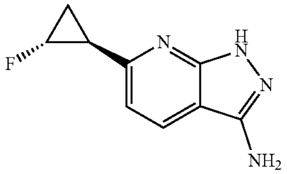

Step 1: 6-((1RS,2SR)-2-fluorocyclopropyl)-2-hydroxynicotinonitrile

The title compound ([M+H]$^+$ 179.0) was prepared by reaction of 3-(dimethylamino)-1-((trans)-2-fluorocyclopropyl)prop-2-en-1-one (prepared by a modified procedure from J. Med. Chem. 2011, 54, 7974 from 1-(2-fluorocyclopropyl)ethanone (WO2016/161960 A1, 2016)) and 2-cyanoacetamide using NaOMe as a base (General procedure G).

Step 2: 2-chloro-6-((1RS,2SR)-2-fluorocyclopropyl)nicotinonitrile

The title compound ($^1$H NMR (CHLOROFORM-d, 300 MHz) δ 7.84 (d, 1H, J=7.9 Hz), 7.30 (d, 1H, J=7.9 Hz), 4.70-5.20 (m, 1H), 2.40-2.60 (m, 1H), 1.60-1.80 (m, 1H), 1.50-1.60 (in, 1H) was prepared by reaction of 6-((1RS,2SR)-2-fluorocyclopropyl)-2-hydroxynicotinonitrile (step 1) with $POCl_3$ (General procedure H).

Step 3: 6-((1RS,2RS)-2-methylcyclopropyl)-1H-pyrazolo[3,4-b]pyridin-3-amine

The title compound ([M+H]$^+$ 193.0) was prepared from 2-chloro-6-((1RS,2RS)-2-methylcyclopropyl)nicotinonitrile (step 2) and hydrazine in ethanol at 75° C. in accordance with General procedure C.

Intermediate 21: 6-(2,2-difluorocyclopropyl)-1H-pyrazolo[3,4-b]pyridin-3-amine

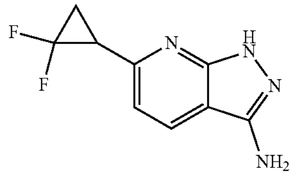 [SMILES: Nc1n[nH]c2nc(C3CC3(F)F)ccc12]

Step 1: 2-chloro-6-vinylnicotinonitrile

The title compound ([M+H, Cl]$^+$165.0) was prepared from 2,6-dichloronicotinonitrile and 4,4,5,5-tetramethyl-2-vinyl-1,3,2-dioxaborolane under $Pd(dppf)_2Cl_2 \cdot CH_2Cl_2$ complex catalysis at 100° C. in accordance with General procedure A.

Step 2: 2-chloro-6-(2,2-difluorocyclopropyl)nicotinonitrile

To a solution of 2-chloro-6-vinylnicotinonitrile (step 1) (50 mg, 0.30 mmol) in THF (2 mL) was added trimethyl (trifluoromethyl)silane (112 μL, 0.76 mmol) and NaI (9.2 mg, 0.06 mmol). The reaction was stirred in a sealed tube at 65° C. for 2 h. A further portion of trimethyl(trifluoromethyl)silane (112 μL, 0.76 mmol) and NaI (9.2 mg, 0.06 mmol) was added and the reaction stirred for another hour at 65° C. before a final further portion of trimethyl(trifluoromethyl) silane (112 μL, 0.76 mmol) and NaI (9.2 mg, 0.06 mmol) was added and the reaction stirred for 3 h more. The reaction was diluted with ethylacetate, washed with saturated aqueous sodium hydrogen carbonate, brine, dried ($Na_2SO_4$) and concentrated. Flash silica gel chromatography (Ethylacetate: n-Heptane 0:1-1:1) afforded the title compound (27 mg, 41%) as a yellow oil. ([M+H, Cl]$^+$215.1)

Step 3: 6-(2,2-difluorocyclopropyl)-1H-pyrazolo[3,4-b]pyridin-3-amine

The title compound ([M+H]$^+$ 211.1) was prepared from 2-chloro-6-(2,2-difluorocyclopropyl)nicotinonitrile (step 2) and hydrazine in ethanol at 100° C. in accordance with General procedure C.

Intermediate 22: 6-[(1RS,2RS)-2-(trifluoromethyl) cyclopropyl]-1H-pyrazolo[3,4-b]pyridin-3-amine

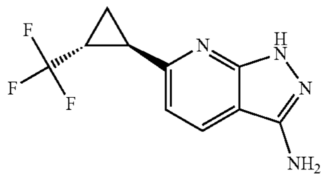

Step 1: 2-chloro-6-[(1RS,2RS)-2-(trifluoromethyl) cyclopropyl]pyridine-3-carbonitrile The title compound ([M+H, Cl]$^+$247.0) was prepared from 2,6-dichloronicotinonitrile and potassium trifluoro ((1RS,2RS)-2-(trifluoromethyl)cyclopropyl)borate) under butyldi-1-adamantylphosphine/palladium (II) acetate catalysis in toluene/water at 120° C. in accordance with General procedure A. The desired product was inseparable from 6-chloro-2-[(1RS,2RS)-2-(trifluoromethyl)cyclopropyl] pyridine-3-carbonitrile isomer.

Step 3: 6-[(1RS,2RS)-2-(trifluoromethyl)cyclopropyl]-1H-pyrazolo[3,4-b]pyridin-3-amine The title compound ([M+H]$^+$ 243.1) was prepared from 2-chloro-6-[(1RS,2RS)-2-(trifluoromethyl)cyclopropyl] pyridine-3-carbonitrile (step 2) and hydrazine in ethanol at 100° C. in accordance with General procedure C.

Intermediate 23: 6-((1rs,2RS,3SR)-2,3-dimethylcyclopropyl)-1H-pyrazolo[3,4-b]pyridin-3-amine

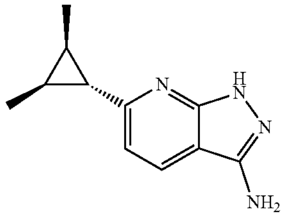

Step 1: 6-((1,rs,2RS,3SR)-2,3-dimethylcyclopropyl)-2-hydroxynicotinonitrile

The title compound ([M+H]$^+$ 189.1) was prepared by reaction of (E)-3-(dimethylamino)-1-((2RS,3SR)-2,3-dimethylcyclopropyl)prop-2-en-1-one (prepared by a modified procedure from J. Med. Chem. 2011, 54, 7974 from 1-[rac-(2R,3S)-2,3-dimethylcyclopropyl]ethanone (J. Org. Chem. 1978, 3422)) and 2-cyanoacetamide using NaOMe as a base (General procedure G).

Step 2: 2-chloro-6-((1rs,2RS,3SR)-2,3-dimethylcyclopropyl)nicotinonitrile

The title compound ([M+H]$^+$ 207.1) was prepared by reaction of 6-((1rs,2R,3S)-2,3-dimethylcyclopropyl)-2-hydroxynicotinonitrile (step 1) with $POCl_3$ (General procedure H).

Step 3: 6-((1rs,2RS,3SR)-2,3-dimethylcyclopropyl)-1H-pyrazolo[3,4-b]pyridin-3-amine The title compound ([M+H]$^+$ 203.1) was prepared from 2-chloro-6-((1rs,2RS,3SR)-2,3-dimethylcyclopropyl)nicotinonitrile (step 2) and hydrazine in ethanol at 75° C. in accordance with General procedure C.

Intermediate 24: 6-(1-methylcyclopropyl)-1H-pyrazolo[3,4-b]pyridin-3-amine

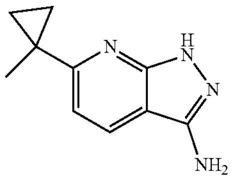

Step 1: 2-hydroxy-6-(1-methylcyclopropyl)nicotinonitrile

The title compound ([M+H]$^+$ 189.1) was prepared by reaction of (E)-3-(dimethylamino)-1-(1-methylcyclopropyl) prop-2-en-1-one (prepared by a modified procedure from J. Med. Chem. 2011, 54, 7974 from 1-(1-methylcyclopropyl) ethan-1-one (Chem. Berichte, 1981, 3831) and 2-cyanoacetamide using NaOMe as a base (General procedure G).

Step 2: 2-chloro-6-(1-methylcyclopropyl)nicotinonitrile

The title compound ($^1H$ NMR (CHLOROFORM-d, 300 MHz) δ 7.80-7.90 (m, 1H), 7.30 (d, 1H, J=8.3 Hz), 1.51 (s, 3H), 1.40-1.43 (m, 2H), 0.90-1.0 (m, 2H)) was prepared by reaction of 2-hydroxy-6-(1-methylcyclopropyl)nicotinonitrile (step 1) with $POCl_3$ (General procedure H).

Step 3: 6-(1-methylcyclopropyl)-1H-pyrazolo[3,4-b] pyridin-3-amine

The title compound ([M+H]$^+$ 189.1) was prepared from 2-chloro-6-(1-methylcyclopropyl)nicotinonitrile (step 2) and hydrazine in ethanol at 75° C. in accordance with General procedure C.

Intermediate 25: 6-(3-azabicyclo[2.2.1]heptan-3-yl)-1H-pyrazolo[3,4-b]pyridin-3-amine

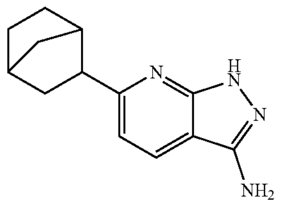 [SMILES: Nc1n[nH]c2nc(C3CC4CCC3C4)ccc12]

Step 1: 6-(3-azabicyclo[2.2.1]heptan-3-yl)-2-chloropyridine-3-carbonitrile

The title compound ($^1H$ NMR (400 MHz, DMSO-d6) δ=7.93-7.71 (m, 2H), 6.72 (br d, J=8.8 Hz, 1H), 6.37 (br d, J=8.8 Hz, 1H), 4.79-4.62 (m, 1H), 4.57-4.40 (m, 1H), 3.42-3.35 (m, 2H), 3.21-3.12 (m, 1H), 3.02 (br d, J=9.6 Hz, 1H), 2.70-2.61 (m, 2H), 1.76-1.62 (m, 6H), 1.57-1.35 (m, 6H)) was prepared from 2,6-dichloronicotinonitrile and 3-azabicyclo[2.2.1]heptane in THF and TEA as base in accordance with General procedure B.

Step 2: 6-(3-azabicyclo[2.2.1]heptan-3-yl)-1H-pyrazolo[3,4-b]pyridin-3-amine

The title compound ($[M+H]^+$ 205.2) was prepared from 6-(3-azabicyclo[2.2.1]heptan-3-yl)-2-chloro-pyridine-3-carbonitrile (step 1) and hydrazine in ethanol at 80° C. in accordance with General procedure C.

Intermediate 26: [3-amino-6-(7-azabicyclo[2.2.1]heptan-7-yl)pyrazolo[3,4-b]pyridin-1-yl]-(2-methoxyphenyl)methanone

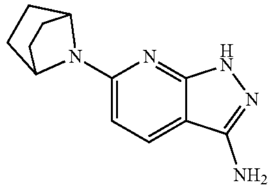 [SMILES: Nc1n[nH]c2nc(N3C4CCC3CC4)ccc12]

Step 1: 6-(7-azabicyclo[2.2.1]heptan-7-yl)-2-chloro-pyridine-3-carbonitrile

The title compound ($^1$H NMR (400 MHz, DMSO-d6) δ=8.01 (d, J=1.3 Hz, 1H), 6.99-6.84 (m, 1H), 4.74-4.48 (m, 2H), 1.73-1.64 (m, 4H), 1.57-1.46 (m, 4H)) was prepared from 2,6-dichloronicotinonitrile and 7-azabicyclo[2.2.1]heptane hydrochloride in THF/acetonitrile (1:1) and DIPEA as base in accordance with General procedure B.

Step 2: [3-amino-6-(7-azabicyclo[2.2.1]heptan-7-yl)pyrazolo[3,4-b]pyridin-1-yl]-(2-methoxyphenyl)methanone The title compound ($^1$H NMR (400 MHz, DMSO-d6) δ=11.47-11.24 (m, 1H), 7.84-7.68 (m, 1H), 6.52 (d, J=8.8 Hz, 1H), 5.26-5.08 (s, 2H), 4.61-4.35 (s, 2H), 1.71-1.60 (m, 4H), 1.50-1.37 (m, 4H)) was prepared from 6-(7-azabicyclo[2.2.1]heptan-7-yl)-2-chloro-pyridine-3-carbonitrile (step 1) and hydrazine in ethanol at 80° C. in accordance with General procedure C.

Intermediate 27: (3RS,4RS)-3-methyl-2-oxopiperidine-4-carboxylic acid

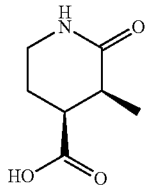

3-Methyl-2-oxo-1,2-dihydropyridine-4-carboxylic acid (Tetrahedron, 1989, 7469) (1.82 g, 11.9 mmol) was suspended in methanol (5 ml) and 10% Pd—C (632 mg, 0.5 mmol) added and the reaction stirred under an atmosphere of hydrogen (balloon) for 72 h. The reaction was filtered through Hyflo®, washing generously with MeOH and concentrated to afford the title compound (1.85 g, 84%) as a white solid. ($[M-H]^-$ 156.0)

Intermediate 28: (E)-N-(6-cyclopropyl-1H-pyrazolo[3,4-b]pyridin-3-yl)-1-phenylmethanimine

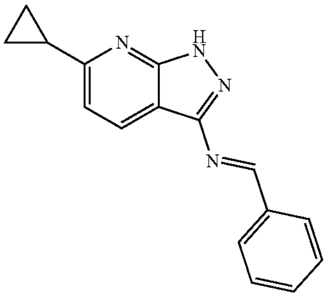 [SMILES: C(=N\c1n[nH]c2nc(C3CC3)ccc12)/c1ccccc1]

To a suspension of 6-cyclopropyl-1H-pyrazolo[3,4-b]pyridin-3-amine (Intermediate 5) (200 mg, 1.15 mmol) in EtOH (4 ml) was added benzaldehyde (0.13 mL, 1.26 mmol) and the mixture heated to 80° C. for 1 hr. The reaction was cooled to ambient temperature and the title product isolated by filtration (309 mg, quant.) as an offwhite solid. ($^1$H NMR (CHLOROFORM-d, 300 MHz) δ 13.28 (s, 1H), 9.20 (s, 1H), 8.28 (d, 1H, J=8.3 Hz), 8.00-8.10 (m, 2H), 7.5-7.6 (m, 3H), 7.21 (d, 1H, J=8.3 Hz), 2.20-2.30 (m, 1H), 1.00-1.10 (m, 4H))

EXAMPLES

| Ex. No. | Structure | Product Name | Mol. Weight found | From Intermediates | Prep. |
|---|---|---|---|---|---|
| 1 | 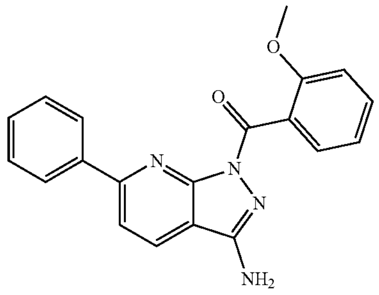 [SMILES: COc1ccccc1C(=O)n1nc(N)c2ccc(-c3ccccc3)nc21] | (3-amino-6-phenyl-1H-pyrazolo[3,4-b]pyridin-1-yl)(2-methoxyphenyl)methanone | $[M + H]^+$ 345.1 | 6-phenyl-1H-pyrazolo[3,4-b]pyridin-3-amine (Intermediate 1) and 2-methoxybenzoic acid | F1 |

-continued

| Ex. No. | Structure | Product Name | Mol. Weight found | From Intermediates | Prep. |
|---|---|---|---|---|---|
| 2 | 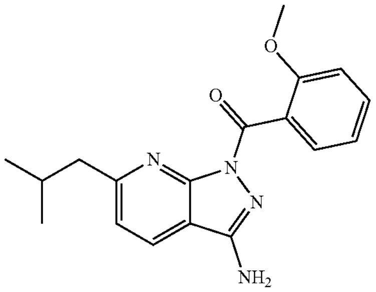 [SMILES: COc1ccccc1C(=O)n1nc(N)c2ccc(CC(C)C)nc21] | (3-amino-6-isobutyl-1H-pyrazolo[3,4-b]pyridin-1-yl)(2-methoxyphenyl)methanone | $[M + H]^+$ 325.1 | 6-isobutyl-1H-pyrazolo[3,4-b]pyridin-3-amine (Intermediate 2) and 2-methoxybenzoic | F1 |
| 3 | 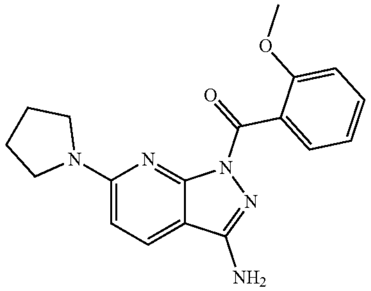 [SMILES: COc1ccccc1C(=O)n1nc(N)c2ccc(N3CCCC3)nc21] | (3-amino-6-(pyrrolidin-1-yl)-1H-pyrazolo[3,4-b]pyridin-1-yl)(2-methoxyphenyl)methanone | $[M + H]^+$ 338.2 | 6-(pyrrolidin-1-yl)-1H-pyrazolo[3,4-b]pyridin-3-amine (Intermediate 3) and 2-methoxybenzoic acid | F1 |
| 4 | 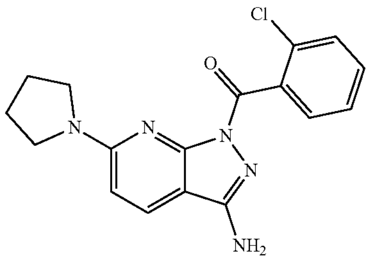 [SMILES: Nc1nn(C(=O)c2ccccc2Cl)c2nc(N3CCCC3)ccc12] | (3-amino-6-(pyrrolidin-1-yl)-1H-pyrazolo[3,4-b]pyridin-1-yl)(2-chlorophenyl)methanone | $[M + H, Cl]^+$ 342.2 | 6-(pyrrolidin-1-yl)-1H-pyrazolo[3,4-b]pyridin-3-amine (Intermediate 3) and 2-chlorobenzoic acid | F1 |
| 5 | 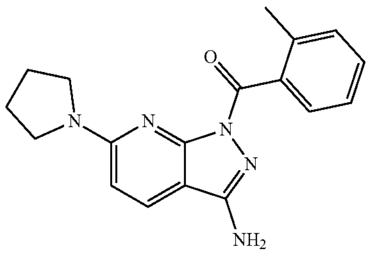 [SMILES: Cc1ccccc1C(=O)n1nc(N)c2ccc(N3CCCC3)nc21] | (3-amino-6-(pyrrolidin-1-yl)-1H-pyrazolo[3,4-b]pyridin-1-yl)(o-tolyl)methanone | $[M + H]^+$ 322.2 | 6-(pyrrolidin-1-yl)-1H-pyrazolo[3,4-b]pyridin-3-amine (Intermediate 3) and 2-methylbenzoic acid | F1 |
| 6 | 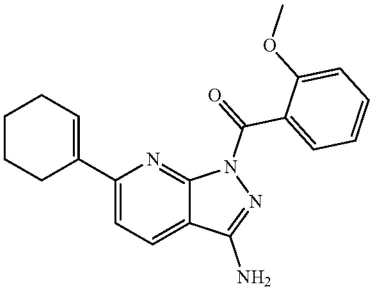 [SMILES: COc1ccccc1C(=O)n1nc(N)c2ccc(C3=CCCCC3)nc21] | [3-amino-6-(cyclohexen-1-yl)pyrazolo[3,4-b]pyridin-1-yl]-(2-methoxyphenyl)methanone | $[M + H]^+$ 349.2 | 6-(cyclohexen-1-yl)-1H-pyrazolo[3,4-b]pyridin-3-amine (Intermediate 4) and 2-methoxybenzoic acid | F1 |

-continued

| Ex. No. | Structure | Product Name | Mol. Weight found | From Intermediates | Prep. |
|---|---|---|---|---|---|
| 7 | 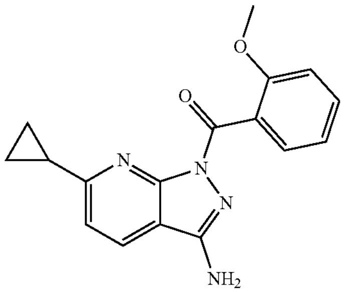 | (3-amino-6-cyclopropylpyrazolo[3,4-b]pyridin-1-yl)-(2-methoxyphenyl)methanone | $[M + H]^+$ 309.2 | cyclopropyl-1H-pyrazolo[3,4-b]pyridin-3-amine (Intermediate 5) and 2-methoxybenzoic acid | F1 |
| 8 | 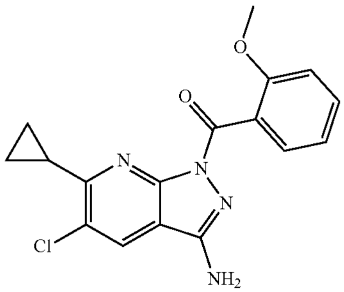 [SMILES: COc1ccccc1C(=O)n1nc(N)c2cc(Cl)c(C3CC3)nc21] | (3-amino-5-chloro-6-cyclopropyl-1H-pyrazolo[3,4-b]pyridin-1-yl)(2-methoxyphenyl)methanone | $[M + H, Cl]^+$ 343.1 | 5-chloro-6-cyclopropyl-1H-pyrazolo[3,4-b]pyridin-3-ylamine (CAS: 1135283-22-5) and 2-methoxybenzoic acid | F1 |
| 9 | 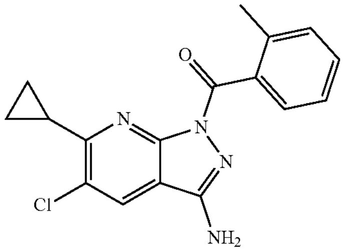 [SMILES: Cc1ccccc1C(=O)n1nc(N)c2cc(Cl)c(C3CC3)nc21] | (3-amino-5-chloro-6-cyclopropyl-1H-pyrazolo[3,4-b]pyridin-1-yl)(2-methoxyphenyl)methanone | $[M + H, Cl]^+$ 327.1 | 5-chloro-6-cyclopropyl-1H-pyrazolo[3,4-b]pyridin-3-ylamine (CAS: 1135283-22-5) and 2-methylbenzoic acid | F1 |
| 10 | 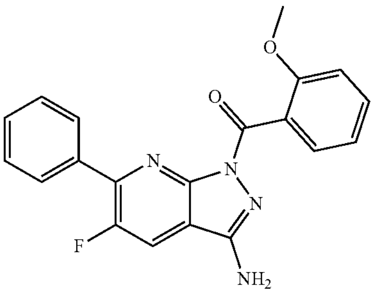 [SMILES: COc1ccccc1C(=O)n1nc(N)c2cc(F)c(-c3ccccc3)nc21] | (3-amino-5-fluoro-6-phenyl-1H-pyrazolo[3,4-b]pyridin-1-yl)(2-methoxyphenyl)methanone | $[M + H]^+$ 363.1 | 5-fluoro-6-phenyl-1H-pyrazolo[3,4-b]pyridin-3-amine (Intermediate 6) and 2-methoxybenzoic acid | F1 |
| 11 | 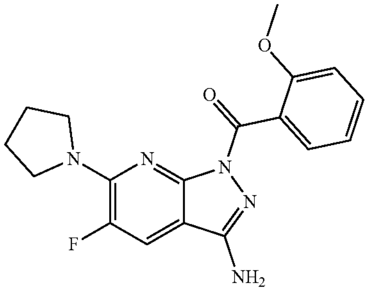 | (3-amino-5-fluoro-6-(pyrrolidin-1-yl)-1H-pyrazolo[3,4-b]pyridin-1-yl)(2-methoxyphenyl)methanone | $[M + H]^+$ 365.2 | 5-fluoro-6-pyrrolidin-1-yl-1H-pyrazolo[3,4-b]pyridin-3-ylamine (Intermediate 7) and 2-methoxybenzoic acid | F1 |

-continued

| Ex. No. | Structure | Product Name | Mol. Weight found | From Intermediates | Prep. |
|---|---|---|---|---|---|
| 12 | 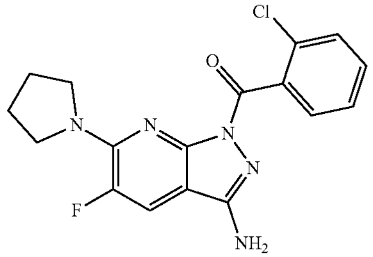 [SMILES: Nc1nn(C(=O)c2ccccc2Cl)c2nc(N3CCCC3)c(F)cc12] | (3-amino-5-fluoro-6-(pyrrolidin-1-yl)-1H-pyrazolo[3,4-b]pyridin-1-yl)(2-chlorophenyl)methanone | $[M + H, Cl]^+$ 360.1 | 5-fluoro-6-pyrrolidin-1-yl-1H-pyrazolo[3,4-b]pyridin-3-ylamine (Intermediate 7) and 2-chlorobenzoic acid | F1 |
| 13 | 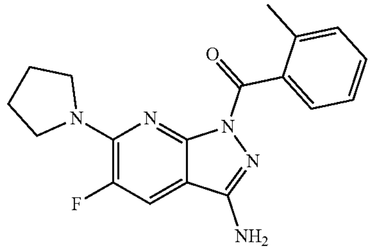 [SMILES: Cc1ccccc1C(=O)n1nc(N)c2cc(F)c(N3CCCC3)nc21] | (3-amino-5-fluoro-6-(pyrrolidin-1-yl)-1H-pyrazolo[3,4-b]pyridin-1-yl)(o-tolyl)methanone | $[M + H]^+$ 340.1 | 5-fluoro-6-pyrrolidin-1-yl-1H-pyrazolo[3,4-b]pyridin-3-ylamine (Intermediate 7) and 2-methylbenzoic acid | F1 |
| 14 | 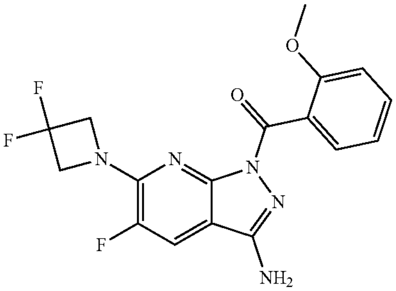 | (3-amino-6-(3,3-difluoroazetidin-1-yl)-5-fluoro-1H-pyrazolo[3,4-b]pyridin-1-yl)(2-methoxyphenyl)methanone | $[M + H]^+$ 378.1 | 6-(3,3-difluoroazetidin-1-yl)-5-fluoro-1H-pyrazolo[3,4-b]pyridin-3-amine (Intermediate 8) and methoxybenzoic acid | F1 |
| 15 | 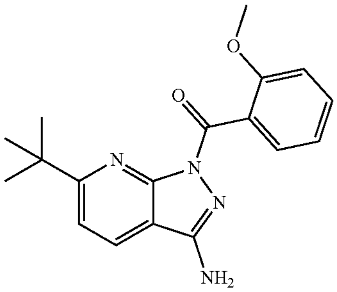 [SMILES: COc1ccccc1C(=O)n1nc(N)c2ccc(C(C)(C)C)nc21] | (3-amino-6-(tert-butyl)-1H-pyrazolo[3,4-b]pyridin-1-yl)(2-methoxyphenyl)methanone | $[M + H]^+$ 325.2 | (3-amino-6-(tert-butyl)-1H-pyrazolo[3,4-b]pyridin-1-yl)(2-methoxyphenyl)methanone (CAS: 951626-63-4) and 2-methoxybenzoic acid | F1 |
| 16 | 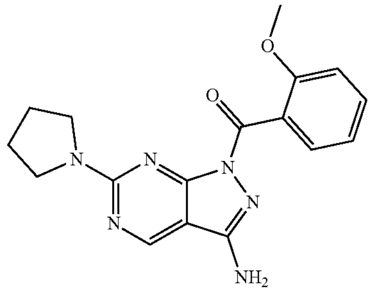 [SMILES: COc1ccccc1C(=O)n1nc(N)c2cnc(N3CCCC3)nc21] | (3-amino-6-(pyrrolidin-1-yl)-1H-pyrazolo[3,4-d]pyrimidin-1-yl)(2-methoxyphenyl)methanone | $[M + H]^+$ 339.3 | 6-(pyrrolidin-1-yl)-1H-pyrazolo[3,4-d]pyrimidin-3-amine (Intermediate 9) and 2-methoxybenzoic acid | F1 |

-continued

| Ex. No. | Structure | Product Name | Mol. Weight found | From Intermediates | Prep. |
|---|---|---|---|---|---|
| 17 | 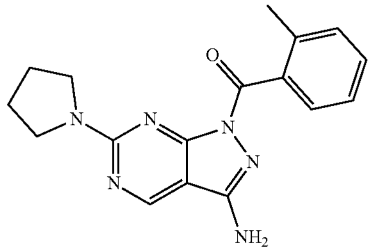 [SMILES: Cc1ccccc1C(=O)n1nc(N)c2cnc(N3CCCC3)nc21] | (3-amino-6-(pyrrolidin-1-yl)-1H-pyrazolo[3,4-d]pyrimidin-1-yl)(o-tolyl)methanone | $[M + H]^+$ 323.3 | 6-(pyrrolidin-1-yl)-1H-pyrazolo[3,4-d]pyrimidin-3-amine (Intermediate 9) and 2-methylbenzoic acid | F1 |
| 18 | 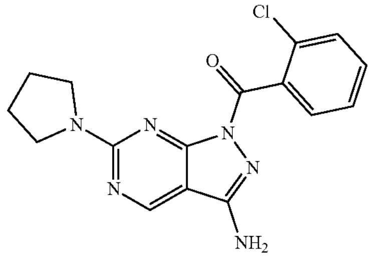 [SMILES: Nc1nn(C(=O)c2ccccc2Cl)c2nc(N3CCCC3)ncc12] | (3-amino-6-(pyrrolidin-1-yl)-1H-pyrazolo[3,4-d]pyrimidin-1-yl)(2-chlorophenyl)methanone | $[M + H, Cl]^+$ 343.2 | 6-(pyrrolidin-1-yl)-1H-pyrazolo[3,4-d]pyrimidin-3-amine (Intermediate 9) and 2-chlorobenzoic acid | F1 |
| 19 | 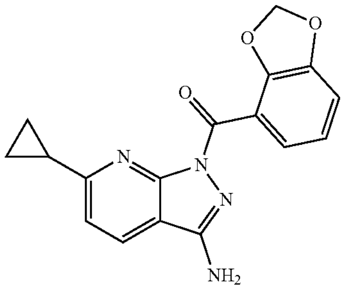 [SMILES: Nc1nn(C(=O)c2cccc3c2OCO3)c2nc(C3CC3)ccc12] | (3-amino-6-cyclopropylpyrazolo[3,4-b]pyridin-1-yl)-(1,3-benzodioxol-4-yl)methanone | $[M + H]^+$ 323.1 | cyclopropyl-1H-pyrazolo[3,4-b]pyridin-3-amine (Intermediate 5) and 1,3-benzodioxole-4-carboxylic acid | F1 |
| 20 | 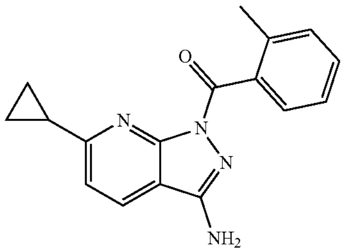 | (3-amino-6-cyclopropylpyrazolo[3,4-b]pyridin-1-yl)-(2-methylphenyl)methanone | $[M + H]^+$ 293.2 | cyclopropyl-1H-pyrazolo[3,4-b]pyridin-3-amine (Intermediate 5) and 2-methylbenzoic acid | F1 |
| 21 | 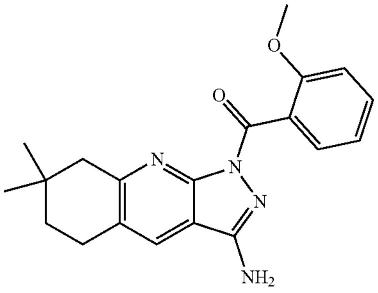 [SMILES: COc1ccccc1C(=O)n1nc(N)c2cc3c(nc21)CC(C)(C)CC3] | (3-amino-7,7-dimethyl-5,6,7,8-tetrahydro-1H-pyrazolo[3,4-b]quinolin-1-yl)(2-methoxyphenyl)methanone | $[M + H]^+$ 351.3 | 6-(pyrrolidin-1-yl)-1H-pyrazolo[3,4-d]pyrimidin-3-amine (Intermediate 10) and 2-methoxybenzoic acid | F1 |

-continued

| Ex. No. | Structure | Product Name | Mol. Weight found | From Intermediates | Prep. |
|---|---|---|---|---|---|
| 22 | 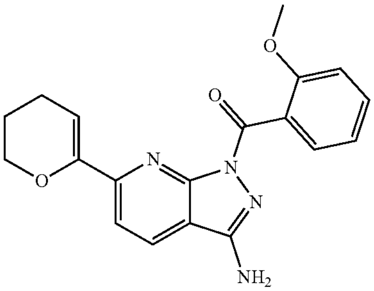 [SMILES: COc1ccccc1C(=O)n1nc(N)c2ccc(C3=CCCCO3)nc21] | [3-amino-6-(3,4-dihydro-2H-pyran-6-yl)pyrazolo[3,4-b]pyridin-1-yl]-(2-methoxyphenyl)methanone | $[M + H]^+$ 351.2 | 6-(3,4-dihydro-2H-pyran-6-yl)-1H-pyrazolo[3,4-b]pyridin-3-amine (Intermediate 11) and 2-methoxybenzoic acid | F1 |
| 23 | 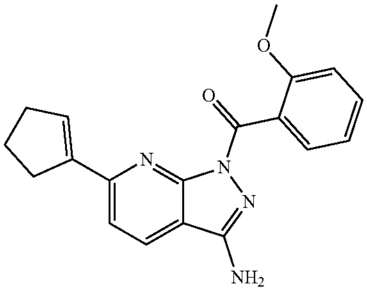 [SMILES: COc1ccccc1C(=O)n1nc(N)c2ccc(C3=CCCC3)nc21] | [3-amino-6-(cyclopenten-1-yl)pyrazolo[3,4-b]pyridin-1-yl]-(2-methoxyphenyl)methanone | $[M + H]^+$ 335.2 | 6-(cyclopenten-1-yl)-1H-pyrazolo[3,4-b]pyridin-3-amine (Intermediate 12) and 2-methoxybenzoic acid | F1 |
| 24 | 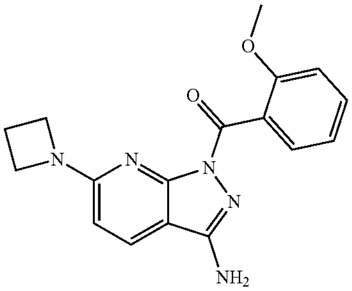 [SMILES: COc1ccccc1C(=O)n1nc(N)c2ccc(N3CCC3)nc21] | (3-amino-6-(azetidin-1-yl)-1H-pyrazolo[3,4-b]pyridin-1-yl)(2-methoxyphenyl)methanone | $[M + H]^+$ 324.2 | 6-(azetidin-1-yl)-1H-pyrazolo[3,4-b]pyridin-3-amine (Intermediate 13) and 2-methoxybenzoic acid | F1 |
| 25 | 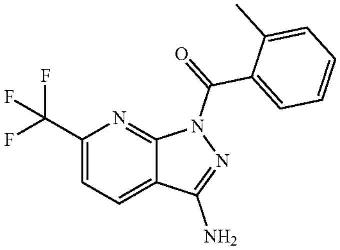 [SMILES: Cc1ccccc1C(=O)n1nc(N)c2ccc(C(F)(F)F)nc21] | (3-amino-6-(trifluoromethyl)-1H-pyrazolo[3,4-b]pyridin-1-yl)(o-tolyl)methanone | $[M + H]^+$ 321.2 | 6-(trifluoromethyl)-1H-pyrazolo[3,4-b]pyridin-3-amine (CAS: 1211578-87-8) and 2-methylbenzoic acid | F1 |
| 26 | 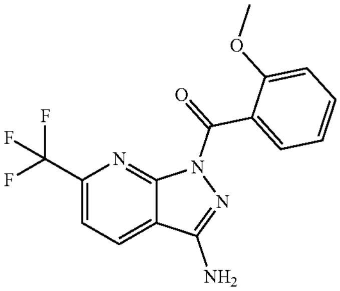 [SMILES: COc1ccccc1C(=O)n1nc(N)c2ccc(C(F)(F)F)nc21] | (3-amino-6-(trifluoromethyl-1H-pyrazolo[3,4-b]pyridin-1-yl)(2-methoxyphenyl)methanone | $[M + H]^+$ 337.1 | 6-(trifluoromethyl)-1H-pyrazolo[3,4-b]pyridin-3-amine (CAS: 1211578-87-8) and 2-methoxybenzoic acid | F1 |

-continued

| Ex. No. | Structure | Product Name | Mol. Weight found | From Intermediates | Prep. |
|---|---|---|---|---|---|
| 27 | 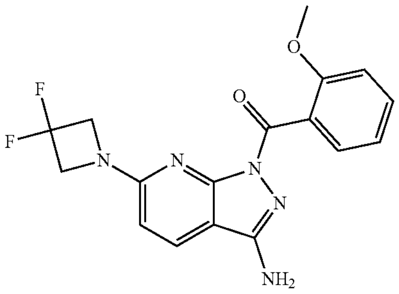 [SMILES: COc1ccccc1C(=O)n1nc(N)c2ccc(N3CC(F)(F)C3)nc21] | (3-amino-6-(3,3-difluoroazetidin-1-yl)-1H-pyrazolo[3,4-b]pyridin-1-yl)(2-methoxyphenyl)methanone | [M + H]+ 360.2 | 6-(3,3-difluoroazetidin-1-yl)-1H-pyrazolo[3,4-b]pyridin-3-amine (Intermediate 14) and 2-methoxybenzoic acid | F1 |
| 28 | 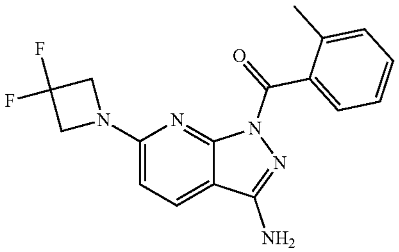 [SMILES: Cc1ccccc1C(=O)n1nc(N)c2ccc(N3CC(F)(F)C3)nc21] | (3-amino-6-(3,3-difluoroazetidin-1-yl)-1H-pyrazolo[3,4-b]pyridin-1-yl)(o-tolyl)methanone | [M + H]+ 344.2 | 6-(3,3-difluoroazetidin-1-yl)-1H-pyrazolo[3,4-b]pyridin-3-amine (Intermediate 14) and 2-methylbenzoic acid | F1 |
| 29 | 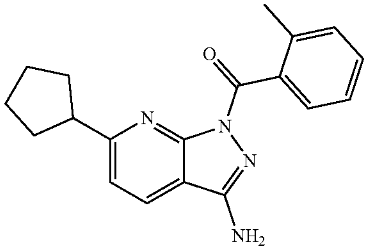 [SMILES: Cc1ccccc1C(=O)n1nc(N)c2ccc(C3CCCC3)nc21] | (3-amino-6-cyclopentylpyrazolo[3,4-b]pyridin-1-yl)-(2-methylphenyl)methanone | [M + H]+ 321.2 | 6-cyclopentyl-1H-pyrazolo[3,4-b]pyridin-3-amine (Intermediate 15) and 2-methylbenzoic acid | F1 |
| 30 | 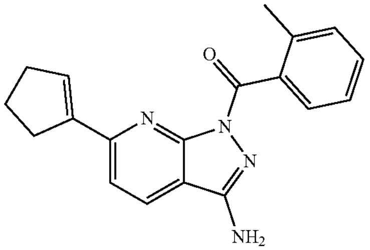 [SMILES: Cc1ccccc1C(=O)n1nc(N)c2ccc(C3=CCCC3)nc21] | [3-amino-6-(cyclopenten-1-yl)pyrazolo[3,4-b]pyridin-1-yl]-(2-methylphenyl)methanone | [M + H]+ 319.2 | 6-(cyclopenten-1-yl)-1H-pyrazolo[3,4-b]pyridin-3-amine (Intermediate 12) and 2-methylbenzoic acid | F1 |
| 31 | 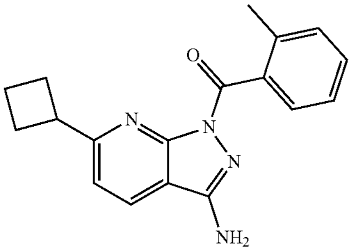 [SMILES: Cc1ccccc1C(=O)n1nc(N)c2ccc(C3CCC3)nc21] | (3-amino-6-cyclobutyl-1H-pyrazolo[3,4-b]pyridin-1-yl)(o-tolyl)methanone | [M + H]+ 307.1 | 6-cyclobutyl-1H-pyrazolo[3,4-b]pyridin-3-amine (Intermediate 16) and 2-methylbenzoic acid | F1 |

-continued

| Ex. No. | Structure | Product Name | Mol. Weight found | From Intermediates | Prep. |
|---|---|---|---|---|---|
| 32 | 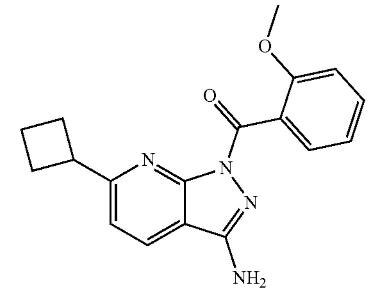 | (3-amino-6-cyclobutyl-1H-pyrazolo[3,4-b]pyridin-1-yl)(o-tolyl)methanone | $[M + H]^+$ 323.1 | 6-cyclobutyl-1H-pyrazolo[3,4-b]pyridin-3-amine (Intermediate 16) and 2-methoxybenzoic acid | F1 |
| 33 | 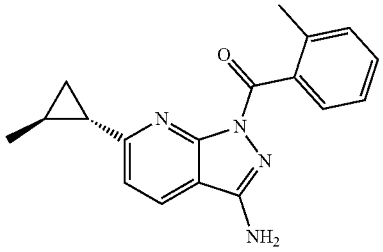 [SMILES: Cc1ccccc1C(=O)n1nc(N)c2ccc([C@H]3C[C@@H]3C)nc21] | (3-amino-6-((1RS,2RS)-2-methylcyclopropyl)-1H-pyrazolo[3,4-b]pyridin-1-yl)(o-tolyl)methanone | $[M + H]^+$ 307.1 | 6-((1RS,2RS)-2-methylcyclopropyl)-1H-pyrazolo[3,4-b]pyridin-3-amine (Intermediate 17) and 2-methylbenzoic acid | F1 |
| 34 | 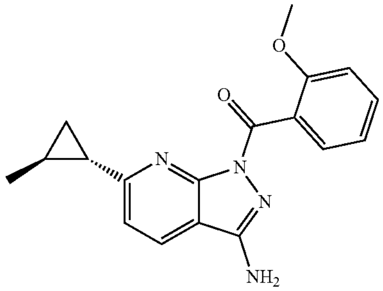 [SMILES: COc1ccccc1C(=O)n1nc(N)c2ccc([C@H]3C[C@@H]3C)nc21] | (3-amino-6-((1RS,2RS)-2-methylcyclopropyl)-1H-pyridin-3-pyrazolo[3,4-b]pyridin-1-yl)(2-methoxyphenyl)methanone | $[M + H]^+$ 323.1 | from 6-((1RS,2RS)-2-methylcyclopropyl)-1H-pyrazolo[3,4-b]pyridin-3-amine (Intermediate 17) and 2-methoxybenzoic acid | F1 |
| 35 | 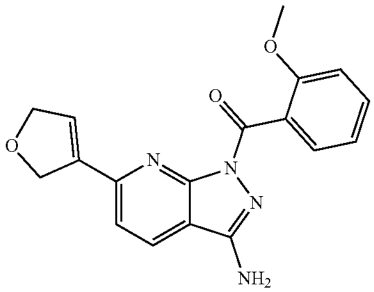 [SMILES: COc1ccccc1C(=O)n1nc(N)c2ccc(C3=CCOC3)nc21] | [3-amino-6-(2,5-dihydrofuran-3-yl)pyrazolo[3,4-b]pyridin-1-yl]-(2-methoxyphenyl)methanone | $[M + H]^+$ 337.1 | 6-(2,5-dihydrofuran-3-yl)-1H-pyrazolo[3,4-b]pyridin-3-amine (Intermediate 18) and 2-methoxybenzoic acid | F1 |
| 36 | 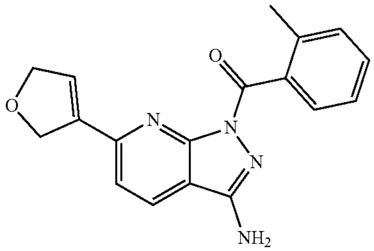 [SMILES: Cc1ccccc1C(=O)n1nc(N)c2ccc(C3=CCOC3)nc21] | [3-amino-6-(2,5-dihydrofuran-3-yl)pyrazolo[3,4-b]pyridin-1-yl]-(2-methylyphenyl)methanone | $[M + H]^+$ 321.1 | 6-(2,5-dihydrofuran-3-yl)-1H-pyrazolo[3,4-b]pyridin-3-amine (Intermediate 18) and 2-methylbenzoic acid | F1 |

-continued

| Ex. No. | Structure | Product Name | Mol. Weight found | From Intermediates | Prep. |
|---|---|---|---|---|---|
| 37 | 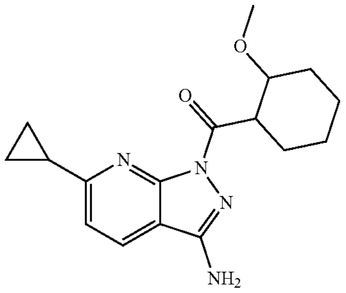 [SMILES: COC1CCCCC1C(=O)n1nc(N)c2ccc(C3CC3)nc21] | (3-amino-6-cyclopropyl-1H-pyrazolo[3,4-b]pyridin-1-yl)(2-methoxycyclohexyl)methanone | $[M + H]^+$ 315.3 | cyclopropyl-1H-pyrazolo[3,4-b]pyridin-3-amine (Intermediate 5) and 2-methoxycyclohexane-1-carboxylic acid (CAS: 13702-44-8) | F1 |
| 38 | 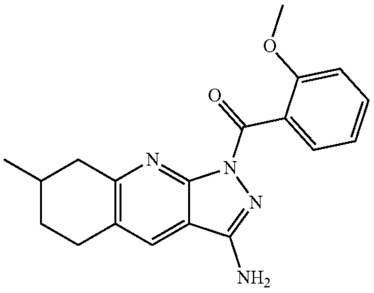 [SMILES: COc1ccccc1C(=O)n1nc(N)c2cc3c(nc21)CC(C)CC3] | (3-amino-7-methyl-5,6,7,8-tetrahydro-1H-pyrazolo[3,4-b]quinolin-1-yl)(2-methoxyphenyl)methanone | $[M + H]^+$ 337.2 | 7-methyl-5,6,7,8-tetrahydro-1H-pyrazolo[3,4-b]quinolin-3-amine (Intermediate 19) and 2-methoxybenzoic acid | F1 |
| 39 | 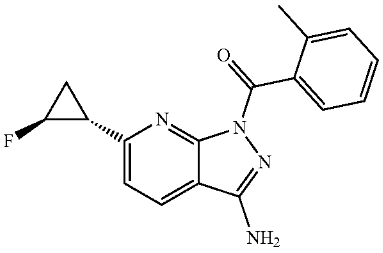 | (3-amino-6-((1RS,2SR)-2-fluorocyclopropyl)-1H-pyrazolo[3,4-b]pyridin-1-yl)(2-methoxyphenyl)methanone | $[M + H]^+$ 327.1 | 6-((1RS,2SR)-2-fluorocyclopropyl)-1H-pyrazolo[3,4-b]pyridin-3-amine (Intermediate 20) and 2-methylbenzoic acid | F1 |
| 40 | 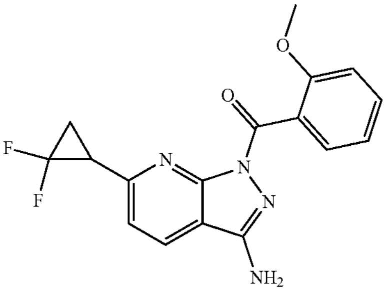 [SMILES: COc1ccccc1C(=O)n1nc(N)c2ccc(C3CC3(F)F)nc21] | (3-amino-6-(2,2-difluorocyclopropyl)-1H-pyrazolo[3,4-b]pyridin-1-yl)(2-methoxyphenyl)methanone | $[M + H]^+$ 345.2 | 6-(2,2-difluorocyclopropyl)-1H-pyrazolo[3,4-b]pyridin-3-amine (Intermediate 21) and 2-methoxybenzoic acid | F1 |
| 41 | 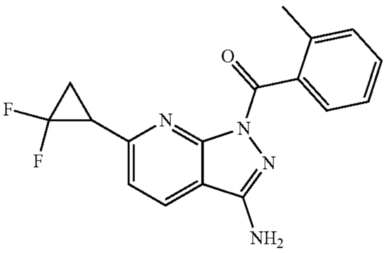 [SMILES: Cc1ccccc1C(=O)n1nc(N)c2ccc(C3CC3(F)F)nc21] | (3-amino-6-(2,2-difluorocyclopropyl)-1H-pyrazolo[3,4-b]pyridin-1-yl)(o-tolyl)methanone | $[M + H]^+$ 329.2 | 6-(2,2-difluorocyclopropyl)-1H-pyrazolo[3,4-b]pyridin-3-amine (Intermediate 21) and 2-methylbenzoic acid | F1 |

-continued

| Ex. No. | Structure | Product Name | Mol. Weight found | From Intermediates | Prep. |
|---|---|---|---|---|---|
| 42 | 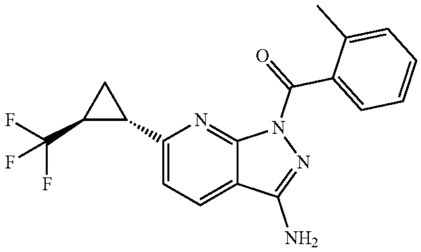 | [3-amino-6-[(1RS,2RS)-2-(trifluoromethyl)cyclopropyl] pyrazolo[3,4-b]pyridin-1-yl]-(2-methoxyphenyl)methanone | $[M + H]^+$ 377.1 | 6-[(1RS,2RS)-2-(trifluoromethyl)cyclopropyl]-1H-pyrazolo[3,4-b]pyridin-3-amine (Intermediate 22) and 2-methylbenzoic acid | F1 |
| 43 | 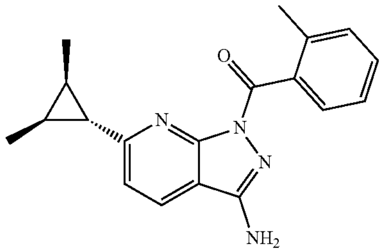 | (3-amino-6-((1rs,2RS,3SR)-2,3-dimethylcyclopropyl)-1H-pyrazolo[3,4-b]pyridin-1-yl)(o-tolyl)methanone | $[M + H]^+$ 337.2 | 6-((1rs,2RS,3SR)-2,3-dimethylcyclopropyl)-1H-pyrazolo[3,4-b]pyridin-3-amine (Intermediate 23) and 2-methylbenzoic acid | F1 |
| 44 | 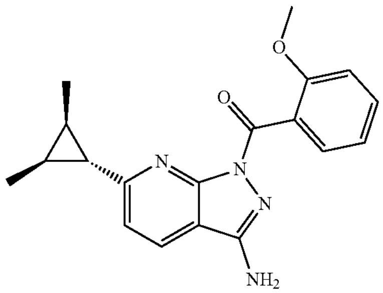 | (3-amino-6-((1rs,2RS,3SR)-2,3-dimethylcyclopropyl)-1H-pyrazolo[3,4-b]pyridin-1-yl)(2-methoxyphenyl)methanone | $[M + H]^+$ 363.1 | 6-((1rs,2RS,3SR)-2,3-dimethylcyclopropyl)-1H-pyrazolo[3,4-b]pyridin-3-amine (Intermediate 23) and 2-methoxybenzoic acid | F1 |
| 45 | 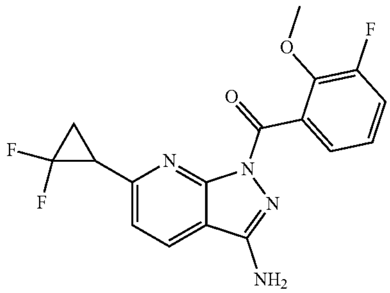 [SMILES: COc1c(F)cccc1C(=O)n1nc(N)c2ccc(C3CC3(F)F)nc21] | (3-amino-6-(2,2-difluorocyclopropyl)-1H-pyrazolo[3,4-b]pyridin-1-yl)(3-fluoro-2-methoxyphenyl)methanone | $[M + H]^+$ 363.1 | 6-(2,2-difluorocyclopropyl)-1H-pyrazolo[3,4-b]pyridin-3-amine (Intermediate 21) and 3-fluoro-2-methoxybenzoic acid | F1 |
| 46 | 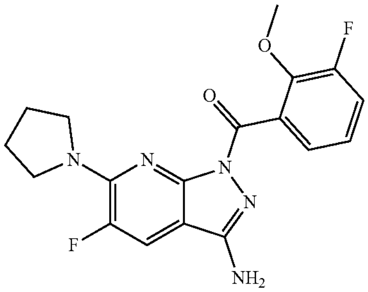 [SMILES: COc1c(F)cccc1C(=O)n1nc(N)c2cc(F)c(N3CCCC3)nc21] | (3-amino-5-fluoro-6-(pyrrolidin-1-yl)-1H-pyrazolo[3,4-b]pyridin-1-yl)(3-fluoro-2-methoxyphenyl)methanone | $[M + H]^+$ 374.2 | 5-fluoro-6-pyrrolidin-1-yl-1H-pyrazolo[3,4-b]pyridin-3-ylamine (Intermediate 7) and 3-fluoro-2-methoxybenzoic acid | F1 |

-continued

| Ex. No. | Structure | Product Name | Mol. Weight found | From Intermediates | Prep. |
|---|---|---|---|---|---|
| 47 | 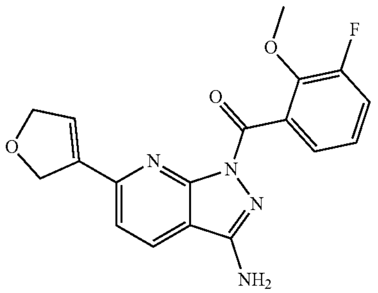 [SMILES: COc1c(F)cccc1C(=O)n1nc(N)c2ccc(C3=CCOC3)nc21] | [3-amino-6-(2,5-dihydrofuran-3-yl)pyrazolo[3,4-b]pyridin-1-yl]-(3-fluoro-2-methoxyphenyl)methanone | [M + H]+ 355.2 | 6-(2,5-dihydrofuran-3-yl)-1H-pyrazolo[3,4-b]pyridin-3-amine (Intermediate 18) and 3-fluoro-2-methoxybenzoic acid | F1 |
| 48 | 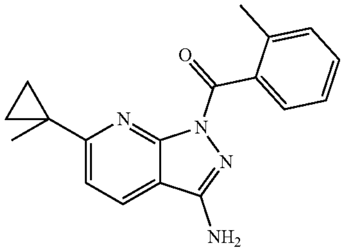 [SMILES: Cc1ccccc1C(=O)n1nc(N)c2ccc(C3(C)CC3)nc21] | (3-amino-6-(1-methylcyclopropyl)-1H-pyrazolo[3,4-b]pyridin-1-yl)(o-tolyl)methanone | [M + H]+ 307.3 | 6-(1-methylcyclopropyl)-1H-pyrazolo[3,4-b]pyridin-3-amine (Intermediate 24) and 2-methylbenzoic acid | F1 |
| 49 | 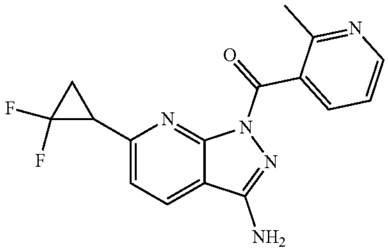 [SMILES: Cc1ncccc1C(=O)n1nc(N)c2ccc(C3CC3(F)F)nc21] | (3-amino-6-(2,2-difluorocyclopropyl)-1H-pyrazolo[3,4-b]pyridin-1-yl)(2-methylpyridin-3-yl)methanone | [M + H]+ 330.2 | 6-(2,2-difluorocyclopropyl)-1H-pyrazolo[3,4-b]pyridin-3-amine (Intermediate 21) and 2-methylpyridine-3-carboxylic acid | F1 |
| 50 | 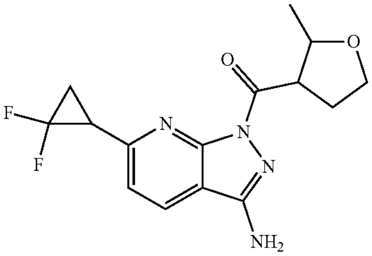 [SMILES: CC1OCCC1C(=O)n1nc(N)c2ccc(C3CC3(F)F)nc21] | (3-amino-6-(2,2-difluorocyclopropyl)-1H-pyrazolo[3,4-b]pyridin-1-yl)(2-methyltetrahydrofuran-3-yl)methanone | [M + H]+ 323.2 | 6-(2,2-difluorocyclopropyl)-1H-pyrazolo[3,4-b]pyridin-3-amine (Intermediate 21) and 2-methyltetrahydrofuran-3-carboxylic acid | F1 |
| 51 | 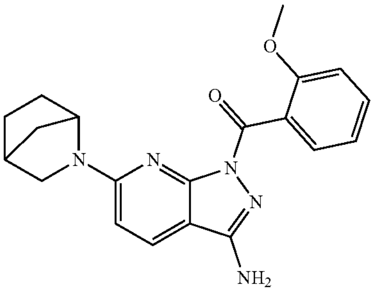 [SMILES: COc1ccccc1C(=O)n1nc(N)c2ccc(N3CC4CCC3C4)nc21] | [3-amino-6-[(1RS,4SR)-3-azabicyclo[2.2.1]heptan-3-yl]pyrazolo[3,4-b]pyridin-1-yl]-(2-methoxyphenyl)methanone | [M + H]+ 364.2 | 6-(3-azabicyclo[2.2.1]heptan-3-yl)-1H-pyrazolo[3,4-b]pyridin-3-amine (Intermediate 25) and 2-methylbenzoic acid | F1 |

-continued

| Ex. No. | Structure | Product Name | Mol. Weight found | From Intermediates | Prep. |
|---|---|---|---|---|---|
| 52 | 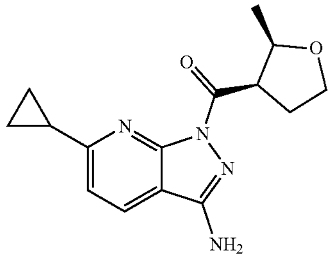 [SMILES: C[C@H]1OCC[C@H]1C(=O)n1nc(N)c2ccc(C3CC3)nc21] | (3-amino-6-cyclopropyl-1H-pyrazolo[3,4-b]pyridin-1-yl)((2RS,3SR)-3-methyltetrahydrofuran-2-yl)methanone | [M + H]$^+$ 287.3 | cyclopropyl-1H-pyrazolo[3,4-b]pyridin-3-amine (Intermediate 5) and (2RS,3SR)-3-methyloxolane-2-carboxylic acid (CAS: 617690-22-9) | F1 |
| 53 | 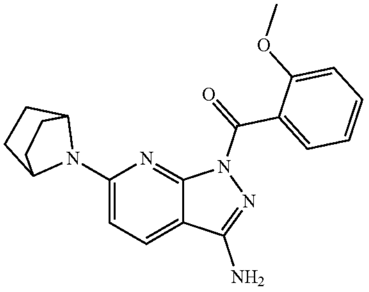 [SMILES: COc1ccccc1C(=O)n1nc(N)c2ccc(N3C4CCC3CC4)nc21] | [3-amino-6-(7-azabicyclo[2.2.1]heptan-7-yl)pyrazolo[3,4-b]pyridin-1-yl]-(2-methoxyphenyl)methanone | [M + H]$^+$ 364.3 | [3-amino-6-(7-azabicyclo[2.2.1]heptan-7-yl)pyrazolo[3,4-b]pyridin-1-yl]-(2-methoxyphenyl)methanone (Intermediate 26) and 2-methylbenzoic acid | F1 |
| 54 | 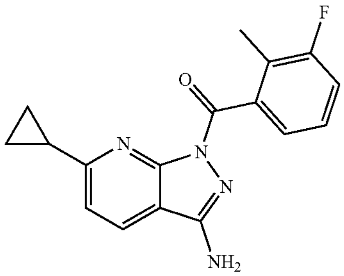 [SMILES: Cc1c(F)cccc1C(=O)n1nc(N)c2ccc(C3CC3)nc21] | (3-amino-6-cyclopropyl-1H-pyrazolo[3,4-b]pyridin-1-yl)(3-fluoro-2-methylphenyl)methanone | [M + H]$^+$ 311.0 | (E)-N-(6-cyclopropyl-1H-pyrazolo[3,4-b]pyridin-3-yl)-1-phenylmethanimine (Intermediate 28) and 3-fluoro-2-methyl-benzoic acid | F2 |
| 55 | 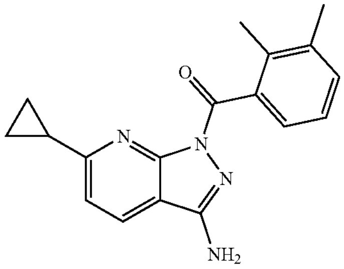 [SMILES: Cc1cccc(C(=O)n2nc(N)c3ccc(C4CC4)nc32)c1C] | (3-amino-6-cyclopropyl-1H-pyrazolo[3,4-b]pyridin-1-yl)(2,3-dimethylphenyl)methanone | [M + H]$^+$ 307.2 | (E)-N-(6-cyclopropyl-1H-pyrazolo[3,4-b]pyridin-3-yl)-1-phenylmethanimine (Intermediate 28) and 2,3-dimethylbenzoic acid | F2 |
| 56 | 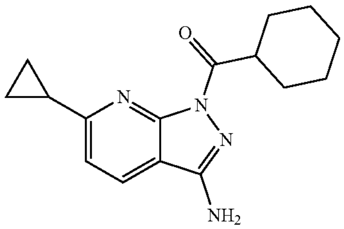 [SMILES: Nc1nn(C(=O)C2CCCCC2)c2nc(C3CC3)ccc12] | (3-amino-6-cyclopropyl-1H-pyrazolo[3,4-b]pyridin-1-yl)(cyclohexyl)methanone | [M + H]$^+$ 285.3 | (E)-N-(6-cyclopropyl-1H-pyrazolo[3,4-b]pyridin-3-yl)-1-phenylmethanimine (Intermediate 28) and cyclohexanecarboxylic acid | F2 |

-continued

| Ex. No. | Structure | Product Name | Mol. Weight found | From Intermediates | Prep. |
|---|---|---|---|---|---|
| 57 | 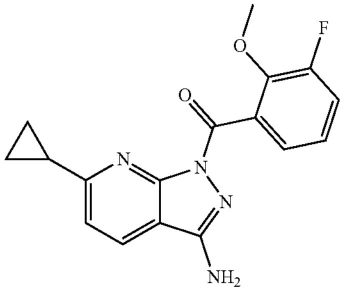 [SMILES: COc1c(F)cccc1C(=O)n1nc(N)c2ccc(C3CC3)nc21] | (3-amino-6-cyclopropyl-1H-pyrazolo[3,4-b]pyridin-1-yl)(3-fluoro-2-methoxyphenyl)methanone | $[M + H]^+$ 327.1 | (E)-N-(6-cyclopropyl-1H-pyrazolo[3,4-b]pyridin-3-yl)-1-phenylmethanimine (Intermediate 28) and 3-fluoro-2-methoxy-benzoic acid | F2 |
| 58 | 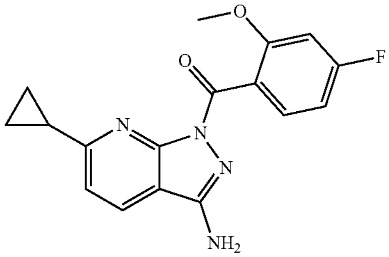 [SMILES: COc1cc(F)ccc1C(=O)n1nc(N)c2ccc(C3CC3)nc21] | (3-amino-6-cyclopropyl-1H-pyrazolo[3,4-b]pyridin-1-yl)(4-fluoro-2-methoxyphenyl)methanone | $[M + H]^+$ 327.2 | (E)-N-(6-cyclopropyl-1H-pyrazolo[3,4-b]pyridin-3-yl)-1-phenylmethanimine (Intermediate 28) and 4-fluoro-2-methoxy-benzoic acid | F2 |
| 59 | 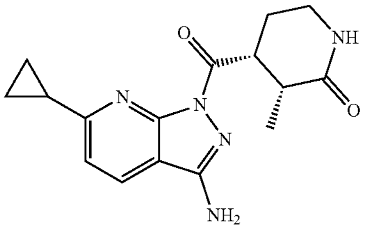 [SMILES: C[C@H]1C(=O)NCC[C@H]1C(=O)n1nc(N)c2ccc(C3CC3)nc21] | (3RS,4RS)-4-(3-amino-6-cyclopropylpyrazolo[3,4-b]pyridine-1-carbonyl)-3-methylpiperidin-2-one | $[M + H]^+$ 314.2 | (E)-N-(6-cyclopropyl-1H-pyrazolo[3,4-b]pyridin-3-yl)-1-phenylmethanimine (Intermediate 28) and (3RS,4RS)-3-methyl-2-oxopiperidine-4-carboxylic acid (Intermediate 27) | F2 |
| 60 | 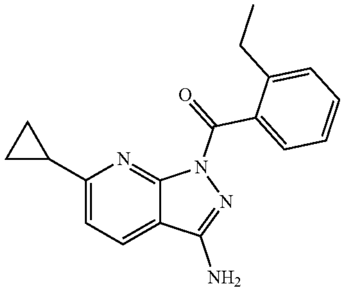 [SMILES: CCc1ccccc1C(=O)n1nc(N)c2ccc(C3CC3)nc21] | (3-amino-6-cyclopropyl-1H-pyrazolo[3,4-b]pyridin-1-yl)(2-ethylphenyl)methanone | $[M + H]^+$ 307.2 | (E)-N-(6-cyclopropyl-1H-pyrazolo[3,4-b]pyridin-3-yl)-1-phenylmethanimine (Intermediate 28) and 2-ethyl-benzoic acid | F2 |
| 61 | 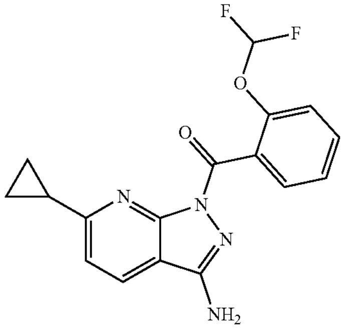 [SMILES: Nc1nn(C(=O)c2ccccc2OC(F)F)c2nc(C3CC3)ccc12] | (3-amino-6-cyclopropyl-1H-pyrazolo[3,4-b]pyridin-1-yl)(2-(difluoromethoxy)phenyl) methanone | $[M + H]^+$ 345.2 | (E)-N-(6-cyclopropyl-1H-pyrazolo[3,4-b]pyridin-3-yl)-1-phenylmethanimine (Intermediate 28) and 2-(difluoromethoxy)benzoic acid | F2 |

-continued

| Ex. No. | Structure | Product Name | Mol. Weight found | From Intermediates | Prep. |
|---|---|---|---|---|---|
| 62 | 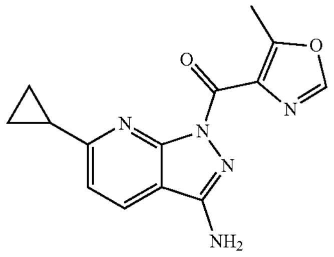 [SMILES: Cc1ocnc1C(=O)n1nc(N)c2ccc(C3CC3)nc21] | (3-amino-6-cyclopropyl-1H-pyrazolo[3,4-b]pyridin-1-yl)(5-methyloxazol-4-yl)methanone | $[M + H]^+$ 284.1 | (E)-N-(6-cyclopropyl-1H-pyrazolo[3,4-b]pyridin-3-yl)-1-phenylmethanimine (Intermediate 28) and 5-methyloxazole-4-carboxylic acid | F2 |
| 63 | 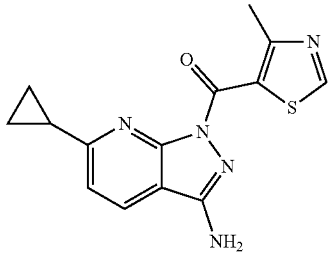 [SMILES: Cc1ncsc1C(=O)n1nc(N)c2ccc(C3CC3)nc21] | (3-amino-6-cyclopropyl-1H-pyrazolo[3,4-b]pyridin-1-yl)(4-methylthiazol-5-yl)methanone | $[M + H]^+$ 300.1 | (E)-N-(6-cyclopropyl-1H-pyrazolo[3,4-b]pyridin-3-yl)-1-phenylmethanimine (Intermediate 28) and 4-methylthiazole-5-carboxylic acid | F2 |
| 64 | 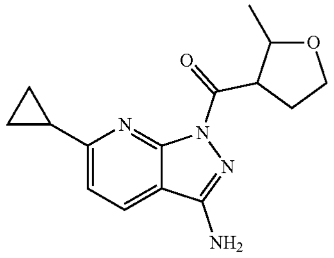 [SMILES: CC1OCCC1C(=O)n1nc(N)c2ccc(C3CC3)nc21] | (3-amino-6-cyclopropyl-1H-pyrazolo[3,4-b]pyridin-1-yl)(2-methyltetrahydrofuran-3-yl)methanone | $[M + H]^+$ 287.1 | (E)-N-(6-cyclopropyl-1H-pyrazolo[3,4-b]pyridin-3-yl)-1-phenylmethanimine (Intermediate 28) and 2-methyltetrahydrofuran-3-carboxylic acid | F2 |
| 65 | 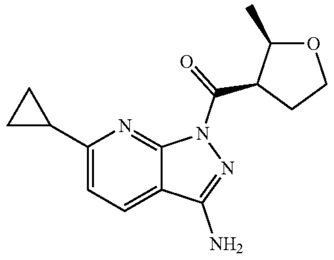 [SMILES: C[C@H]1OCC[C@H]1C(=O)n1nc(N)c2ccc(C3CC3)nc21] | (3-amino-6-cyclopropyl-1H-pyrazolo[3,4-b]pyridin-1-yl)((2SR,3RS)-2-methyltetrahydrofuran-3-methyloxolane-2-yl)methanone | $[M + H]^+$ 287.1 | (E)-N-(6-cyclopropyl-1H-pyrazolo[3,4-b]pyridin-3-yl)-1-phenylmethanimine (Intermediate 28) and (2RS,3SR)-3-carboxylic acid (CAS: 617690-22-9) | F2 |
| 66 | 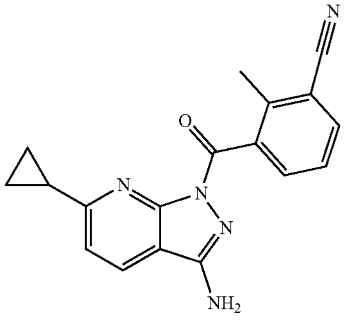 [SMILES: Cc1c(C#N)cccc1C(=O)n1nc(N)c2ccc(C3CC3)nc21] | 3-(3-amino-6-cyclopropyl-1H-pyrazolo[3,4-b]pyridine-1-carbonyl)-2-methylbenzonitrile | $[M + H]^+$ 318.2 | (E)-N-(6-cyclopropyl-1H-pyrazolo[3,4-b]pyridin-3-yl)-1-phenylmethanimine (Intermediate 28) and 3-cyano-2-methyl-benzoic acid | F2 |

-continued

| Ex. No. | Structure | Product Name | Mol. Weight found | From Intermediates | Prep. |
|---|---|---|---|---|---|
| 67 | 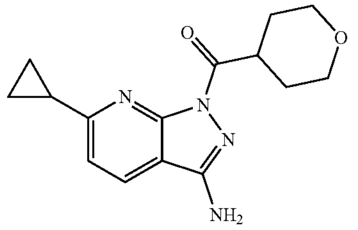 [SMILES: Nc1nn(C(=O)C2CCOCC2)c2nc(C3CC3)ccc12] | (3-amino-6-cyclopropyl-1H-pyrazolo[3,4-b]pyridin-1-yl)(tetrahydro-2H-pyran-4-yl)methanone | $[M + H]^+$ 287.2 | (E)-N-(6-cyclopropyl-1H-pyrazolo[3,4-b]pyridin-3-yl)-1-phenylmethanimine (Intermediate 28) and | F2 |
| 68 | 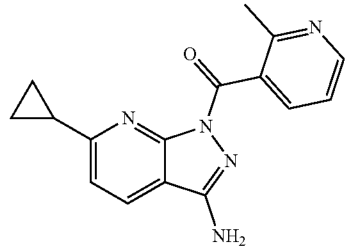 [SMILES: Cc1ncccc1C(=O)n1nc(N)c2ccc(C3CC3)nc21] | (3-amino-6-cyclopropyl-1H-pyrazolo[3,4-b]pyridin-1-yl)(2-methylpyridin-methylpyridine-3-yl)methanone | $[M + H]^+$ 294.2 | (E)-N-(6-cyclopropyl-1H-pyrazolo[3,4-b]pyridin-3-yl)-1-phenylmethanimine (Intermediate 28) and -methylpyridine-3-carboxylic acid | F2 |
| 69 | 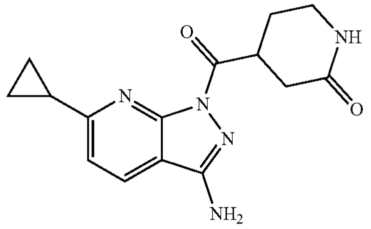 [SMILES: Nc1nn(C(=O)C2CCNC(=O)C2)c2nc(C3CC3)ccc12] | 4-(3-amino-6-cyclopropyl-1H-pyrazolo[3,4-b]pyridine-1-carbonyl)piperidin-2-one | $[M + H]^+$ 300.2 | (E)-N-(6-cyclopropyl-1H-pyrazolo[3,4-b]pyridin-3-yl)-1-phenylmethanimine (Intermediate 28) and 2-oxopiperidine-4-carboxylic acid | F2 |
| 70 | 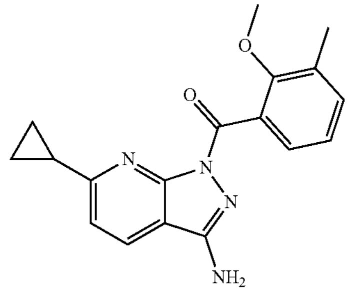 [SMILES: COc1c(C)cccc1C(=O)n1nc(N)c2ccc(C3CC3)nc21] | (3-amino-6-cyclopropyl-1H-pyrazolo[3,4-b]pyridin-1-yl)(2-methoxy-3-methylphenyl)methanone | $[M + H]^+$ 323.2 | (E)-N-(6-cyclopropyl-1H-pyrazolo[3,4-b]pyridin-3-yl)-1-phenylmethanimine (Intermediate 28) and 2-methoxy-3-methyl-benzoic acid | F2 |
| 71 | 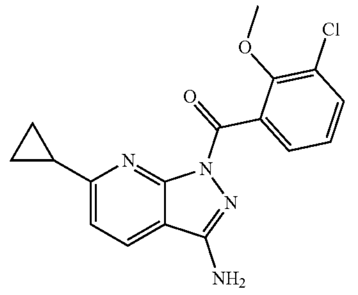 | (3-amino-6-cyclopropyl-1H-pyrazolo[3,4-b]pyridin-1-yl)(3-chloro-2-methoxyphenyl)methanone | $[M + H, Cl]^+$ 343.2 | (E)-N-(6-cyclopropyl-1H-pyrazolo[3,4-b]pyridin-3-yl)-1-phenylmethanimine (Intermediate 28) and 3-chloro-2-methoxy-benzoic acid | F2 |

-continued

| Ex. No. | Structure | Product Name | Mol. Weight found | From Intermediates | Prep. |
|---|---|---|---|---|---|
| 72 | 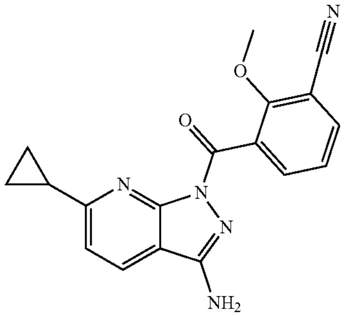 [SMILES: COc1c(C#N)cccc1C(=O)n1nc(N)c2ccc(C3CC3)nc21] | 3-(3-amino-6-cyclopropyl-1H-cyclopropyl-1H-pyrazolo[3,4-b]pyridine-1-carbonyl)-2-methoxybenzonitrile | [M + H]+ 334.3 | (E)-N-(6-pyrazolo[3,4-b]pyridin-3-yl)-1-phenylmethanimine (Intermediate 28) and 3-cyano-2-methoxy-benzoic acid | F2 |
| 73 | 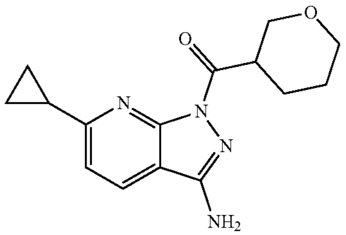 [SMILES: Nc1nn(C(=O)C2CCCOC2)c2nc(C3CC3)ccc12] | (3-amino-6-cyclopropyl-1H-cyclopropyl-1H-pyrazolo[3,4-b]pyridin-1-yl)(tetrahydro-2H-pyran-3-yl)methanone | [M + H]+ 287.3 | (E)-N-(6-pyrazolo[3,4-b]pyridin-3-yl)-1-phenylmethanimine (Intermediate 28) and tetrahydropyran-3-carboxylic acid | F2 |
| 74 | 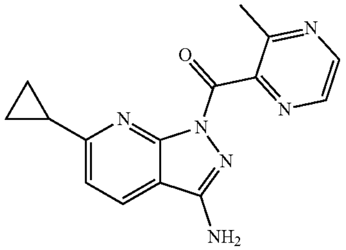 [SMILES: Cc1nccnc1C(=O)n1nc(N)c2ccc(C3CC3)nc21] | (3-amino-6-cyclopropyl-1H-pyrazolo[3,4-b]pyridin-1-yl)(3-methylpyrazin-2-yl)methanone | [M + H]+ 295.3 | (E)-N-(6-cyclopropyl-1H-pyrazolo[3,4-b]pyridin-3-yl)-1-phenylmethanimine (Intermediate 28) and 3-methylpyrazine-2-carboxylic acid | F2 |
| 75 | 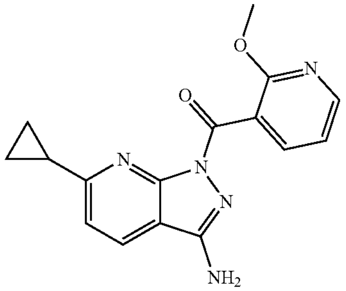 [SMILES: COc1ncccc1C(=O)n1nc(N)c2ccc(C3CC3)nc21] | (3-amino-6-cyclopropyl-1H-pyrazolo[3,4-b]pyridin-1-yl)(2-methoxypyridin-3-yl)methanone | [M + H]+ 310.3 | (E)-N-(6-cyclopropyl-1H-pyrazolo[3,4-b]pyridin-3-yl)-1-phenylmethanimine (Intermediate 28) and 2-methoxypyridine-3-carboxylic acid | F2 |
| 76 | 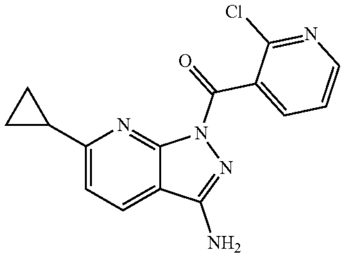 [SMILES: Nc1nn(C(=O)c2cccnc2Cl)c2nc(C3CC3)ccc12] | (3-amino-6-cyclopropyl-1H-pyrazolo[3,4-b]pyridin-1-yl)(2-chloropyridin-3-yl)methanone | [M + H, Cl]+ 314.2 | (E)-N-(6-cyclopropyl-1H-pyrazolo[3,4-b]pyridin-3-yl)-1-phenylmethanimine (Intermediate 28) and 2-chloropyridine-3-carboxylic acid | F2 |

-continued

| Ex. No. | Structure | Product Name | Mol. Weight found | From Intermediates | Prep. |
|---|---|---|---|---|---|
| 77 | 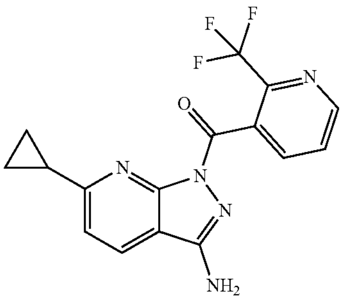 [SMILES: Nc1nn(C(=O)c2cccnc2C(F)(F)F)c2nc(C3CC3)ccc12] | (3-amino-6-cyclopropyl-1H-pyrazolo[3,4-b]pyridin-1-yl)(2-(trifluoromethyl)pyridin-3-yl)methanone | $[M + H]^+$ 348.2 | (E)-N-(6-cyclopropyl-1H-pyrazolo[3,4-b]pyridin-3-yl)-1-phenylmethanimine (Intermediate 28) and 2-(trifluoromethyl)pyridine-3-carboxylic acid | F2 |
| 78 | 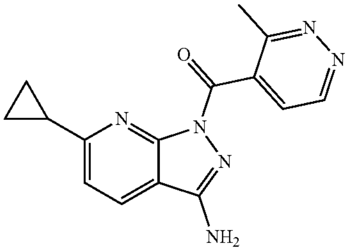 [SMILES: Cc1nnccc1C(=O)n1nc(N)c2ccc(C3CC3)nc21] | (3-amino-6-cyclopropyl-1H-pyrazolo[3,4-b]pyridin-1-yl)(3-methylpyridazin-4-yl)methanone | $[M + H]^+$ 295.5 | (E)-N-(6-cyclopropyl-1H-pyrazolo[3,4-b]pyridin-3-yl)-1-phenylmethanimine (Intermediate 28) and 3-methylpyridazine-4-carboxylic acid | F2 |
| 79 | 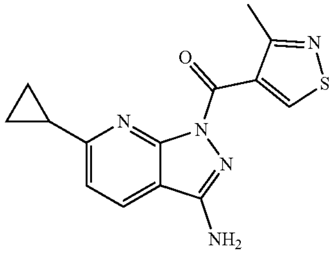 [SMILES: Cc1nscc1C(=O)n1nc(N)c2ccc(C3CC3)nc21] | (3-amino-6-cyclopropyl-1H-pyrazolo[3,4-b]pyridin-1-yl)(3-methylisothiazol-4-yl)methanone | $[M + H]^+$ 300.2 | (E)-N-(6-cyclopropyl-1H-pyrazolo[3,4-b]pyridin-3-yl)-1-phenylmethanimine (Intermediate 28) and 3-methylisothiazole-4-carboxylic acid | F2 |

Aspects of the Present Invention:

1. A compound formula I:

(I)

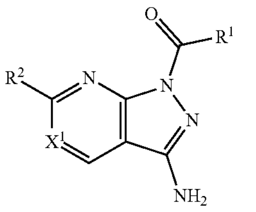

wherein $X^1$ is either N or $CR^3$;

$R^1$ is:

($C_3$-$C_8$)cycloalkyl optionally substituted with one or more, particularly one to three, more particularly one or two substituents $R^{1a}$, heteroaryl optionally substituted with one or more, particularly one to three, more particularly one or two substituents $R^{1b}$, heterocycloalkyl optionally substituted with one or more, particularly one to three, more particularly one or two substituents $R^{1c}$; or phenyl optionally substituted with one or more, particularly one to three, more particularly one or two substituents $R^{1d}$;

$R^{1a}$, $R^{1b}$, $R^{1c}$ and $R^{1d}$ are each independently selected from halogen, oxo, cyano, hydroxyl, ($C_1$-$C_6$)alkyl, ($C_1$-$C_6$)alkoxy, ($C_3$-$C_6$)cycloalkyl, ($C_3$-$C_6$)cycloalkyl-($C_1$-$C_6$)alkyl, halo($C_1$-$C_6$)alkyl, halo($C_1$-$C_6$)alkoxy, hydroxy($C_1$-$C_6$)alkyl, ($C_1$-$C_6$)alkoxy-($C_1$-$C_6$)alkyl, heteroaryl, heterocycloalkyl and phenyl;

$R^2$ is ($C_1$-$C_6$)alkyl, ($C_1$-$C_6$)alkoxy, halo($C_1$-$C_6$)alkyl, halo($C_1$-$C_6$)alkoxy, ($C_3$-$C_6$)cycloalkyl optionally substituted with one or more, particularly one to three, more particularly one or two substituents $R^{2a}$, heterocycloalkyl optionally substituted with one or more, particularly one to three, more particularly one or two substituents $R^{2b}$ or phenyl optionally substituted with one or more, particularly one to three, more particularly one or two substituents $R^{2c}$;

$R^{2a}$, $R^{2b}$ and $R^{2c}$ are each independently selected from halogen, ($C_1$-$C_6$)alkyl, ($C_1$-$C_6$)alkoxy, halo($C_1$-$C_6$)alkyl and halo($C_1$-$C_6$)alkoxy;

$R^3$ is hydrogen, halogen or ($C_1$-$C_6$)alkyl;

or $R^2$ and $R^3$ together form $C_{2-7}$-alkylene optionally substituted with one or more, particularly one to three, more particularly one or two substituents $R^{3f}$ and $R^{3f}$ are each independently selected from halogen, ($C_1$-$C_6$)alkyl, halo($C_1$-$C_6$)alkyl;

and pharmaceutically acceptable salts thereof.

2. A compound according to aspect 1, wherein the compound is of formula I':

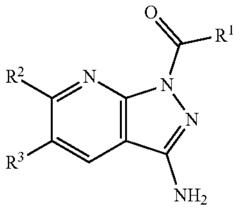

(I')

$R^1$ is:

($C_3$-$C_8$)cycloalkyl optionally substituted with one or more, particularly one to three, more particularly one or two substituents $R^{1a}$, heteroaryl optionally substituted with one or more, particularly one to three, more particularly one or two substituents $R^{1b}$, heterocycloalkyl optionally substituted with one or more, particularly one to three, more particularly one or two substituents $R^{1c}$; or phenyl optionally substituted with one or more, particularly one to three, more particularly one or two substituents $R^{1d}$;

$R^{1a}$, $R^{1b}$, $R^{1c}$ and $R^{1d}$ are each independently selected from halogen, oxo, cyano, hydroxyl, ($C_1$-$C_6$)alkyl, ($C_1$-$C_6$)alkoxy, ($C_3$-$C_6$)cycloalkyl, ($C_3$-$C_6$)cycloalkyl-($C_1$-$C_6$)alkyl, halo($C_1$-$C_6$)alkyl, halo($C_1$-$C_6$)alkoxy, hydroxy($C_1$-$C_6$)alkyl, ($C_1$-$C_6$)alkoxy-($C_1$-$C_6$)alkyl, heteroaryl, heterocycloalkyl and phenyl;

$R^2$ is ($C_1$-$C_6$)alkyl, halo($C_1$-$C_6$)alkyl, ($C_3$-$C_6$)cycloalkyl optionally substituted with one or more, particularly one to three, more particularly one or two substituents $R^{2a}$, heterocycloalkyl optionally substituted with one or more, particularly one to three, more particularly one or two substituents $R^{2b}$ or phenyl optionally substituted with one or more, particularly one to three, more particularly one or two substituents $R^{2c}$;

$R^{2a}$, $R^{2b}$ and $R^{2c}$ are each independently selected from halogen, ($C_1$-$C_6$)alkyl, ($C_1$-$C_6$)alkoxy, halo($C_1$-$C_6$)alkyl and halo($C_1$-$C_6$)alkoxy;

$R^3$ is hydrogen, halogen or ($C_1$-$C_6$)alkyl;

or $R^2$ and $R^3$ together form $C_{2-7}$-alkylene optionally substituted with one or more, particularly one to three, more particularly one or two substituents $R^{3f}$ and $R^{3f}$ are each independently selected from halogen, ($C_1$-$C_6$)alkyl, and halo($C_1$-$C_6$)alkyl;

and pharmaceutically acceptable salts thereof.

3. The compound according to aspects 1, wherein $X^1$ is $CR^3$.

4. The compound according to any one of aspects 1 to 3, wherein $R^1$ is ($C_3$-$C_8$)cycloalkyl optionally substituted with one substituents $R^{1a}$, heteroaryl optionally substituted with one $R^{1b}$, heterocycloalkyl optionally substituted with one or two $R^{1c}$ or phenyl optionally substituted with one or two $R^{1d}$;

5. The compound according to any one of aspects 1 to 4, wherein $R^1$ is ($C_3$-$C_6$)cycloalkyl optionally substituted with one $R^{1a}$, pyridinyl optionally substituted with one $R^{1b}$ pyrazinyl optionally substituted with one $R^{1b}$, pyridizanyl optionally substituted with one $R^{1b}$, thiazolyl optionally substituted with one $R^{1b}$, 1,3-benzodioxolyl optionally substituted with one $R^{1c}$, oxazolyl optionally substituted with one $R^{1c}$, piperidinyl optionally substituted with one $R^{1c}$, tetrahydrofuranyl optionally substituted with one Rio, tetrahydropyranyl optionally substituted with one $R^{1c}$ or phenyl optionally substituted with one or two $R^{1d}$, 6. The compound according to any one of aspects 1 to 5, wherein $R^1$ is cyclohexyl optionally substituted with one $R^{1a}$, pyridinyl optionally substituted with one $R^{1b}$, pyrazinyl optionally substituted with one $R^{1b}$, pyridizanyl optionally substituted with one $R^{1b}$, thiazolyl optionally substituted with one $R^{1b}$, 1,3-benzodioxolyl, oxazolyl optionally substituted with one $R^{1c}$, piperidinyl optionally substituted with one Rio, tetrahydrofuranyl optionally substituted with one $R^{1c}$, tetrahydropyranyl or phenyl optionally substituted with one or two $R^{1d}$.

7. The compound according to any one of aspects 1 to 6, wherein $R^1$ most particularly $R^1$ is pyridinyl optionally substituted with one $R^{1b}$ or phenyl optionally substituted with one or two $R^{1d}$.

8. The compound according to any one of aspects 1 to 4, wherein $R^1$ is heteroaryl optionally substituted with one $R^{1b}$ or phenyl optionally substituted with one or two $R^{1d}$ 9. The compound according to any one of aspects 1 to 8, wherein $R^{1a}$, $R^{1b}$, $R^{1c}$ and $R^{1d}$ are each independently selected from halogen, oxo, cyano, ($C_1$-$C_6$) alkyl, ($C_1$-$C_6$)alkoxy, halo($C_1$-$C_6$)alkyl and halo($C_1$-$C_6$)alkoxy.

10. The compound according to any one of aspects 1 to 9, wherein $R^{1a}$, $R^{1b}$, $R^{1c}$ and $R^{1d}$ are each independently selected from halogen, oxo, cyano, ($C_1$-$C_3$) alkyl, ($C_1$-$C_3$)alkoxy, halo($C_1$-$C_3$)alkyl and halo($C_1$-$C_3$)alkoxy.

11. The compound according to any one of aspects 1 to 10, wherein $R^{1a}$, $R^{1b}$, $R^{1c}$ and $R^{1d}$ are each independently selected from chloro, fluoro, oxo, cyano, methyl, ethyl, methoxy, trifluoromethyl and difluoromethyl.

12. The compound according to any one of aspects 1 to 11, wherein $R^{1a}$, $R^{1b}$, $R^{1c}$ and $R^{1d}$ are each independently selected from chloro, fluoro, cyano, methyl and methoxy.

13. The compound according to any one of aspects 1 to 10, wherein $R^{1b}$ and $R^{1d}$ are each independently selected from halogen, cyano, ($C_1$-$C_3$)alkyl, ($C_1$-$C_3$) alkoxy, halo($C_1$-$C_3$)alkyl and halo($C_1$-$C_3$)alkoxy.

14. The compound according to any one of aspects 1 to 10, wherein $R^{1b}$ are each independently selected from halogen, ($C_1$-$C_3$)alkyl, ($C_1$-$C_3$)alkoxy and halo ($C_1$-$C_3$)alkyl and wherein $R^{1d}$ are each independently selected from halogen, cyano, ($C_1$-$C_3$)alkyl, ($C_1$-$C_3$)alkoxy, halo($C_1$-$C_3$)alkyl and halo($C_1$-$C_3$) alkoxy.

15. The compound according to any one of aspects 1 to 10, wherein $R^{1b}$ are each independently selected from chloro, methyl and methoxy and wherein $R^{1d}$ are each independently selected from fluoro, cyano, methyl and methoxy.

16. The compound according to any one of aspects 1 to 15, $R^1$ is 2-methoxyphenyl, 2-chlorophenyl, 2-methylphenyl, 1,3-benzodioxol-4-yl, 3-fluoro-2-methylphenyl, 2,3-dimethylphenyl, cyclohexyl, 2-methoxycyclohexyl, 3-fluoro-2-methoxyphenyl, 4-fluoro-2-methoxyphenyl, 3-methyl-2-oxopiperidin-4-yl, 2-ethylphenyl, 2-(difluoromethoxy)phenyl, 5-methyl-1,3-oxazol-4-yl, 4-methyl-1,3-thiazol-5-yl, 2-methyloxolan-3-yl, 3-methyl-tetrahydrofuran-2-yl, 3-cyano-2-methylphenyl, oxan-4-yl, 2-methylpyridin-3-yl, 2-oxopiperidin-4-yl, 2-methoxy-3-methylphenyl, 3-chloro-2-methoxyphenyl, 3-cyano-2-methoxyphenyl, oxan-3-yl, 3-methylpyrazin-2-yl, 2-methoxypyridin-3-yl, 2-chloropyridin-3-yl, 2-(trifluoromethyl)pyridin-3-yl, 3-methylpyridazin-4-yl, 3-methyl-1,2-thiazol-4-yl or 3-methyltetrahydrofuran-2-yl.

17. The compound according to any one of aspects 1 to 16, wherein $R^1$ is 2-methoxyphenyl, 3-fluoro-2-methoxyphenyl, 2-methylpyridin-3-yl, 3-cyano-2-methoxyphenyl, 2-methoxypyridin-3-yl, 2-chloropyridin-3-yl or 2-methylphenyl.

18. The compound according to any one of aspects 1 to 17, wherein $R^2$ is $(C_1\text{-}C_6)$alkyl, halo$(C_1\text{-}C_6)$alkyl, $(C_3\text{-}C_6)$cycloalkyl optionally substituted with one or two substituents $R^{2a}$, heterocycloalkyl optionally substituted with one or two substituents $R^{2b}$ or phenyl.

19. The compound according to any one of aspects 1 to 18, wherein $R^2$ is $(C_1\text{-}C_3)$alkyl, halo$(C_1\text{-}C_3)$alkyl, cyclopropyl optionally substituted with one or two substituents $R^{2a}$, cyclobutyl, cyclopentyl, cyclopentenyl, cylcohexenyl, azetidinyl optionally substituted with one or two substituents $R^{2b}$, dihydrofuranyl, dihydropyranyl, azabicyclo[2.2.1]heptanyl, -azabicyclo[2.2.1]heptanyl, pyrrolidinyl, azetidinyl optionally substituted with one or two substituents $R^{2b}$ or phenyl.

20. The compound according to any one of aspects 1 to 19, wherein $R^2$ is i-butyl, t-butyl, trifluoromethyl, cyclopropyl optionally substituted with one or two substituents $R^{2a}$, cyclobutyl, cyclopentyl, cyclopentenyl, cylcohexenyl, azetidinyl optionally substituted with one or two substituents $R^{2b}$, 2,5-dihydrofuran-3-yl, 3,4-dihydro-pyran-6-yl, 2-azabicyclo[2.2.1]heptan-2-yl, 7-azabicyclo[2.2.1]heptan-7-yl, pyrrolidinyl or phenyl.

21. The compound according to any one of aspects 1 to 17, wherein $R^2$ is halo$(C_1\text{-}C_6)$alkyl, $(C_3\text{-}C_6)$cycloalkyl optionally substituted with one or two substituents $R^{2a}$ or heterocycloalkyl optionally substituted with one or two substituents $R^{2b}$.

22. The compound according to any one of aspects 1 to 21, wherein $R^{2a}$, $R^{2b}$ and $R^{2c}$ are each independently selected from halogen, $(C_1\text{-}C_3)$alkyl and halo$(C_1\text{-}C_3)$alkyl.

23. The compound according to any one of aspects 1 to 22, wherein $R^{2a}$, $R^{2b}$ and $R^{2c}$ are each independently selected from fluoro, methyl and trifluoromethyl.

24. The compound according to any one of aspects 1 to 23, wherein $R^{2a}$ are each independently selected from fluoro, methyl and trifluoromethyl, $R^{2b}$ are each fluoro.

25. The compound according to any one of aspects 1 to 24, wherein $R^2$ is i-butyl, t-butyl, trifluoromethyl, cyclopropyl optionally substituted with one or two substituents selected from fluoro, methyl or trifluoromethyl, cyclobutyl, cyclopentyl, cyclopenten-1-yl, cylcohexen-1-yl, azetidinyl optionally substituted with two fluoro, 2,5-dihydrofuran-3-yl, 3,4-dihydro-pyran-6-yl, 2-azabicyclo[2.2.1]heptan-2-yl, 7-azabicyclo[2.2.1]heptan-7-yl, pyrrolidinyl or phenyl.

26. The compound according to any one of aspects 1 to 25, wherein $R^2$ is trifluoromethyl, cylcopropyl, cyclobutyl, cyclopenten-1-yl, 2-fluorocyclopropyl, 2,2-difluorocyclopropyl, 2-(trifluoromethyl)cyclopropyl, 2,3-dimethylcyclopropyl, 1-methylcyclopropyl or 3,4-dihydro-pyran-6-yl.

27. The compound according to any one of aspects 1 to 26, wherein $R^2$ is phenyl, 2-methylpropyl, pyrrolidin-1-yl, cyclopropyl, cyclohexen-1-yl, 3,4-dihydro-2-pyran-6-yl, cyclopenten-1-yl, azetidin-1-yl, trifluoromethyl, 3,3-difluoroazetidin-1-yl, cyclopentyl, cyclobutyl, 2-methylcyclopropyl, 2,5-dihydrofuran-3-yl, 2-fluorocyclopropyl, 2,2-difluorocyclopropyl, 2-(trifluoromethyl)cyclopropyl, 2,3-dimethylcyclopropyl, 1-methylcyclopropyl, 2-azabicyclo[2.2.1]heptan-2-yl, 7-azabicyclo[2.2.1]heptan-7-yl or t-butyl.

28. The compound according to any one of aspects 1 to 26, wherein $R^2$ is cyclopropyl, cyclopenten-1-yl, trifluoromethyl or cyclobutyl, 2,5-dihydrofuran-3-yl.

29. The compound according to any one of aspects 1 to 28, wherein $R^3$ is hydrogen or halogen.

30. The compound according to any one of aspects 1 to 29, wherein $R^3$ is hydrogen, chloro or fluoro.

31. The compound according to any one of aspects 1 to 30, wherein $R^3$ is hydrogen.

32. The compound according to any one of aspects 1 to 30, selected from the group consisting of:

(3-amino-6-phenyl-1H-pyrazolo[3,4-b]pyridin-1-yl)(2-methoxyphenyl)methanone (3-amino-6-isobutyl-1H-pyrazolo[3,4-b]pyridin-1-yl)(2-methoxyphenyl)methanone (3-amino-6-(pyrrolidin-1-yl)-1H-pyrazolo[3,4-b]pyridin-1-yl)(2-methoxyphenyl)methanone (3-amino-6-(pyrrolidin-1-yl)-1H-pyrazolo[3,4-b]pyridin-1-yl)(2-chlorophenyl)methanone (3-amino-6-(pyrrolidin-1-yl)-1H-pyrazolo[3,4-b]pyridin-1-yl)(o-tolyl)methanone

[3-amino-6-(cyclohexen-1-yl)pyrazolo[3,4-b]pyridin-1-yl]-(2-methoxyphenyl)methanone (3-amino-6-cyclopropylpyrazolo[3,4-b]pyridin-1-yl)-(2-methoxyphenyl)methanone 2,2,2-trifluoroacetic acid (3-amino-5-chloro-6-cyclopropyl-1H-pyrazolo[3,4-b]pyridin-1-yl)(2-methoxyphenyl)methanone (3-amino-5-chloro-6-cyclopropyl-1H-pyrazolo[3,4-b]pyridin-1-yl)(o-tolyl)methanone (3-amino-5-fluoro-6-phenyl-1H-pyrazolo[3,4-b]pyridin-1-yl)(2-methoxyphenyl)methanone (3-amino-5-fluoro-6-(pyrrolidin-1-yl)-1H-pyrazolo[3,4-b]pyridin-1-yl)(2-methoxyphenyl)methanone (3-amino-5-fluoro-6-(pyrrolidin-1-yl)-1H-pyrazolo[3,4-b]pyridin-1-yl)(2-chlorophenyl)methanone (3-amino-5-fluoro-6-(pyrrolidin-1-yl)-1H-pyrazolo[3,4-b]pyridin-1-yl)(o-tolyl)methanone (3-amino-6-(3,3-difluoroazetidin-1-yl)-5-fluoro-1H-pyrazolo[3,4-b]pyridin-1-yl)(2-methoxyphenyl)methanone (3-amino-6-(tert-butyl)-1H-pyrazolo[3,4-b]pyridin-1-yl)(2-methoxyphenyl)methanone (3-amino-6-(pyrrolidin-1-yl)-1H-pyrazolo[3,4-d]pyrimidin-1-yl)(2-methoxyphenyl)methanone (3-amino-6-(pyrrolidin-1-yl)-1H-pyrazolo[3,4-d]pyrimidin-1-yl)(o-tolyl)methanone (3-amino-6-(pyrrolidin-1-yl)-1H-pyrazolo[3,4-d]pyrimidin-1-yl)(2-chlorophenyl)methanone (3-amino-6-cyclopropylpyrazolo[3,4-b]pyridin-1-yl)-(1,3-benzodioxol-4-yl)methanone (3-amino-6-cyclopropylpyrazolo[3,4-b]pyridin-1-yl)-(2-methylphenyl)methanone (3-amino-7,7-dimethyl-5,6,7,8-tetrahydro-1H-pyrazolo[3,4-b]quinolin-1-yl)(2-methoxyphenyl)methanone

[3-amino-6-(3,4-dihydro-2H-pyran-6-yl)pyrazolo[3,4-b]pyridin-1-yl]-(2-methoxyphenyl)methanone

[3-amino-6-(cyclopenten-1-yl)pyrazolo[3,4-b]pyridin-1-yl]-(2-methoxyphenyl)methanone (3-amino-6-(azetidin-1-yl)-1H-pyrazolo[3,4-b]pyridin-1-yl)(2-methoxyphenyl)methanone (3-amino-6-(trifluoromethyl)-1H-pyrazolo[3,4-b]pyridin-1-yl)(o-tolyl)methanone (3-amino-6-(trifluoromethyl)-1H-pyrazolo[3,4-b]pyridin-1-yl)(2-methoxyphenyl)methanone (3-amino-6-(3,3-difluoroazetidin-1-yl)-1H-pyrazolo[3,4-b]pyridin-1-yl)(2-methoxyphenyl)methanone (3-amino-6-(3,3-difluoroazetidin-1-yl)-1H-pyrazolo[3,4-b]pyridin-1-yl)(o-tolyl)methanone (3-amino-6-cyclopentylpyrazolo[3,4-b]pyridin-1-yl)-(2-methylphenyl)methanone

[3-amino-6-(cyclopenten-1-yl)pyrazolo[3,4-b]pyridin-1-yl]-(2-methylphenyl)methanone (3-amino-6-cyclobutyl-1H-pyrazolo[3,4-b]pyridin-1-yl)(o-tolyl)methanone (3-amino-6-cyclobutyl-1H-pyrazolo[3,4-b]pyridin-1-yl)(2-methoxyphenyl)methanone (3-amino-6-cyclopropyl-1H-pyrazolo[3,4-b]pyridin-1-yl)(3-fluoro-2-methylphenyl)methanone (3-amino-6-((1RS,2RS)-2-methylcyclopropyl)-1H-pyrazolo[3,4-b]pyridin-1-yl)(o-tolyl)methanone (3-amino-6-((1RS,2RS)-2-methylcyclopropyl)-1H-pyrazolo[3,4-b]pyridin-1-yl)(2-methoxyphenyl)methanone (3-amino-6-cyclopropyl-1H-pyrazolo[3,4-b]pyridin-1-yl)(2,3-dimethylphenyl)methanone (3-amino-6-cyclopropyl-1H-pyrazolo[3,4-b]pyridin-1-yl)(cyclohexyl)methanone

[3-amino-6-(2,5-dihydrofuran-3-yl)pyrazolo[3,4-b]pyridin-1-yl]-(2-methoxyphenyl)methanone

[3-amino-6-(2,5-dihydrofuran-3-yl)pyrazolo[3,4-b]pyridin-1-yl]-(2-methoxyphenyl)methanone (3-amino-6-cyclopropyl-1H-pyrazolo[3,4-b]pyridin-1-yl)(2-methoxycyclohexyl)methanone (3-amino-7-methyl-5,6,7,8-tetrahydro-1H-pyrazolo[3,4-b]quinolin-1-yl)(2-methoxyphenyl)methanone (3-amino-6-((trans)-2-fluorocyclopropyl)-1H-pyrazolo[3,4-b]pyridin-1-yl)(2-methoxyphenyl)methanone (3-amino-6-cyclopropyl-1H-pyrazolo[3,4-b]pyridin-1-yl)(3-fluoro-2-methoxyphenyl)methanone (3-amino-6-cyclopropyl-1H-pyrazolo[3,4-b]pyridin-1-yl)(4-fluoro-2-methoxyphenyl)methanone (3-amino-6-(2,2-difluorocyclopropyl)-1H-pyrazolo[3,4-b]pyridin-1-yl)(2-methoxyphenyl)methanone (3-amino-6-(2,2-difluorocyclopropyl)-1H-pyrazolo[3,4-b]pyridin-1-yl)(o-tolyl)methanone

[3-amino-6-[rac-(1R,2R)-2-(trifluoromethyl)cyclopropyl]pyrazolo[3,4-b]pyridin-1-yl]-(2-methoxyphenyl)methanone (3-amino-6-((1r,2R,3S)-2,3-dimethylcyclopropyl)-1H-pyrazolo[3,4-b]pyridin-1-yl)(o-tolyl)methanone (3-amino-6-((1r,2R,3S)-2,3-dimethylcyclopropyl)-1H-pyrazolo[3,4-b]pyridin-1-yl)(2-methoxyphenyl)methanone (3-amino-6-(2,2-difluorocyclopropyl)-1H-pyrazolo[3,4-b]pyridin-1-yl)(3-fluoro-2-methoxyphenyl)methanone (3-amino-5-fluoro-6-(pyrrolidin-1-yl)-1H-pyrazolo[3,4-b]pyridin-1-yl)(3-fluoro-2-methoxyphenyl)methanone

[3-amino-6-(2,5-dihydrofuran-3-yl)pyrazolo[3,4-b]pyridin-1-yl]-(3-fluoro-2-methoxyphenyl)methanone rac-(cis)-4-(3-amino-6-cyclopropylpyrazolo[3,4-b]pyridine-1-carbonyl)-3-methylpiperidin-2-one (3-amino-6-cyclopropyl-1H-pyrazolo[3,4-b]pyridin-1-yl)(2-ethylphenyl)methanone (3-amino-6-cyclopropyl-1H-pyrazolo[3,4-b]pyridin-1-yl)(2-(difluoromethoxy)phenyl)methanone (3-amino-6-cyclopropyl-1H-pyrazolo[3,4-b]pyridin-1-yl)(5-methyloxazol-4-yl)methanone (3-amino-6-cyclopropyl-1H-pyrazolo[3,4-b]pyridin-1-yl)(4-methylthiazol-5-yl)methanone (3-amino-6-cyclopropyl-1H-pyrazolo[3,4-b]pyridin-1-yl)(2-methyltetrahydrofuran-3-yl)methanone (3-amino-6-cyclopropyl-1H-pyrazolo[3,4-b]pyridin-1-yl)((2S,3R)-2-methyltetrahydrofuran-3-yl)methanone 3-(3-amino-6-cyclopropyl-1H-pyrazolo[3,4-b]pyridine-1-carbonyl)-2-methylbenzonitrile (3-amino-6-cyclopropyl-1H-pyrazolo[3,4-b]pyridin-1-yl)(tetrahydro-2H-pyran-4-yl)methanone (3-amino-6-cyclopropyl-1H-pyrazolo[3,4-b]pyridin-1-yl)(2-methylpyridin-3-yl)methanone 4-(3-amino-6-cyclopropyl-1H-pyrazolo[3,4-b]pyridine-1-carbonyl)piperidin-2-one (3-amino-6-cyclopropyl-1H-pyrazolo[3,4-b]pyridin-1-yl)(2-methoxy-3-methylphenyl)methanone (3-amino-6-(1-methylcyclopropyl)-1H-pyrazolo[3,4-b]pyridin-1-yl)(o-tolyl)methanone (3-amino-6-(2,2-difluorocyclopropyl)-1H-pyrazolo[3,4-b]pyridin-1-yl)(2-methylpyridin-3-yl)methanone (3-amino-6-(2,2-difluorocyclopropyl)-1H-pyrazolo[3,4-b]pyridin-1-yl)(2-methyltetrahydrofuran-3-yl)methanone (3-amino-6-cyclopropyl-1H-pyrazolo[3,4-b]pyridin-1-yl)(3-chloro-2-methoxyphenyl)methanone 3-(3-amino-6-cyclopropyl-1H-pyrazolo[3,4-b]pyridine-1-carbonyl)-2-methoxybenzonitrile (3-amino-6-cyclopropyl-1H-pyrazolo[3,4-b]pyridin-1-yl)(tetrahydro-2H-pyran-3-yl)methanone (3-amino-6-cyclopropyl-1H-pyrazolo[3,4-b]pyridin-1-yl)(3-methylpyrazin-2-yl)methanone (3-amino-6-cyclopropyl-1H-pyrazolo[3,4-b]pyridin-1-yl)(2-methoxypyridin-3-yl)methanone (3-amino-6-cyclopropyl-1H-pyrazolo[3,4-b]pyridin-1-yl)(2-chloropyridin-3-yl)methanone (3-amino-6-cyclopropyl-1H-pyrazolo[3,4-b]pyridin-1-yl)(2-(trifluoromethyl)pyridin-3-yl)methanone (3-amino-6-cyclopropyl-1H-pyrazolo[3,4-b]pyridin-1-yl)(3-methylpyridazin-4-yl)methanone (3-amino-6-cyclopropyl-1H-pyrazolo[3,4-b]pyridin-1-yl)(3-methylisothiazol-4-yl)methanone

[3-amino-6-[(1R,4S)-3-azabicyclo[2.2.1]heptan-3-yl]pyrazolo[3,4-b]pyridin-1-yl]-(2-methoxyphenyl)methanone (3-amino-6-cyclopropyl-1H-pyrazolo[3,4-b]pyridin-1-yl)((2R,3S)-3-methyltetrahydrofuran-2-yl)methanone

[3-amino-6-(7-azabicyclo[2.2.1]heptan-7-yl)pyrazolo[3,4-b]pyridin-1-yl]-(2-methoxyphenyl)methanone 33. The compound according to any one of aspects 1 to 30, selected from the group consisting of.

(3-amino-6-cyclopropylpyrazolo[3,4-b]pyridin-1-yl)-(2-methoxyphenyl)methanone 2,2,2-trifluoroacetic acid (3-amino-6-cyclopropylpyrazolo[3,4-b]pyridin-1-yl)-(2-methylphenyl)methanone

[3-amino-6-(cyclopenten-1-yl)pyrazolo[3,4-b]pyridin-1-yl]-(2-methoxyphenyl)methanone (3-amino-6-(trifluoromethyl)-1H-pyrazolo[3,4-b]pyridin-1-yl)(2-methoxyphenyl)methanone

[3-amino-6-(cyclopenten-1-yl)pyrazolo[3,4-b]pyridin-1-yl]-(2-methylphenyl)methanone (3-amino-6-cyclobutyl-1H-pyrazolo[3,4-b]pyridin-1-yl)(2-methoxyphenyl)methanone (3-amino-6-((1RS,2RS)-2-methylcyclopropyl)-1H-pyrazolo[3,4-b]pyridin-1-yl)(o-tolyl)methanone (3-amino-6-((1RS,2RS)-2-methylcyclopropyl)-1H-pyrazolo[3,4-b]pyridin-1-yl)(2-methoxyphenyl)methanone (3-amino-6-(2,2-difluorocyclopropyl)-1H-pyrazolo[3,4-b]pyridin-1-yl)(2-methoxyphenyl)methanone (3-amino-6-((1r,2R,3S)-2,3-dimethylcyclopropyl)-1H-pyrazolo[3,4-b]pyridin-1-yl)(2-methoxyphenyl)methanone

[3-amino-6-(2,5-dihydrofuran-3-yl)pyrazolo[3,4-b]pyridin-1-yl]-(3-fluoro-2-methoxyphenyl)methanone (3-amino-6-cyclopropyl-1H-pyrazolo[3,4-b]pyridin-1-yl)(2-methylpyridin-3-yl)methanone (3-amino-6-(2,2-difluorocyclopropyl)-1H-pyrazolo[3,4-b]pyridin-1-yl)(2-methylpyridin-3-yl)methanone 3-(3-amino-6-cyclopropyl-1H-pyrazolo[3,4-b]pyridine-1-carbonyl)-2-methoxybenzonitrile (3-amino-6-cyclopropyl-1H-pyrazolo[3,4-b]pyridin-1-yl)(2-methoxypyridin-3-yl)methanone (3-amino-6-cyclopropyl-1H-pyrazolo[3,4-b]pyridin-1-yl)(2-chloropyridin-3-yl)methanone 34. A compound according to any one of aspects 1 to 33 for use as a therapeutically active substance.

35. Pharmaceutical compositions comprising compounds of formula I or I' according to any one of aspects 1 to 33 or their pharmaceutically acceptable salts and one or more pharmaceutically acceptable excipients.

36. Compounds of formula I or I' according to any one of aspects 1 to 33 or their pharmaceutically acceptable salts above for use as therapeutically active substances.

37. Compounds of formula I or I' according to any one of aspects 1 to 33 or their pharmaceutically acceptable salts for the use in the treatment, prevention and/or delay of progression of Lung Aenocarcinoma, Melanoma, Pancreatic Adenocarcinoma, Head and Neck Squamous Cell Carcinoma, Lung Squamous Cell Carcinoma, Esophageal Carcinoma, Glioblastoma Multiforme, and Mesothelioma.

38. Compounds according to aspect 37, for the use in the treatment, prevention and/or delay of progression of Lung Adenocarcinoma, Lung Squamous Carcinoma, Pancreatic Adenocarcinoma, Glioblastoma Multiforme, and Head and Neck Squamous Carcinoma.

39. A method for the treatment or prevention of Lung Aenocarcinoma, Melanoma, Pancreatic Adenocarcinoma, Head and Neck Squamous Cell Carcinoma, Lung Squamous Cell Carcinoma, Esophageal Carcinoma, Glioblastoma Multiforme, and Mesothelioma, which method comprises administering compounds of formula I according to any one of aspects 1 to 33 or their pharmaceutically acceptable salts as defined above to a subject.

40. A method according to aspect 40 for the treatment or prevention of Lung Adenocarcinoma, Lung Squamous Carcinoma, Pancreatic Adenocarcinoma, Glioblastoma Multiforme, and Head and Neck Squamous Carcinoma.

41. The use of compounds of formula I according to any one of aspects 1 to 33 or their pharmaceutically acceptable salts for the treatment, prevention and/or delay of progression of Lung Aenocarcinoma, Melanoma, Pancreatic Adenocarcinoma, Head and Neck Squamous Cell Carcinoma, Lung Squamous Cell Carcinoma, Esophageal Carcinoma, Glioblastoma Multiforme, and Mesothelioma.

42. The use of compounds according to aspect 41, for the treatment, prevention and/or delay of progression of Lung Adenocarcinoma, Lung Squamous Carcinoma, Pancreatic Adenocarcinoma, Glioblastoma Multiforme, and Head and Neck Squamous Carcinoma.

43. The use of compounds of formula I according to any one of aspects 1 to 33 or their pharmaceutically acceptable salts for the preparation of medicaments for the treatment or prevention of Lung Aenocarcinoma, Melanoma, Pancreatic Adenocarcinoma, Head and Neck Squamous Cell Carcinoma, Lung Squamous Cell Carcinoma, Esophageal Carcinoma, Glioblastoma Multiforme, and Mesothelioma.

44. The use of compounds according to aspect 43, for the treatment, prevention and/or delay of progression of Lung Adenocarcinoma, Lung Squamous Carcinoma, Pancreatic Adenocarcinoma, Glioblastoma Multiforme, and Head and Neck Squamous Carcinoma.

The invention claimed is:

1. A compound selected from the group consisting of:

(3-amino-6-phenyl-1H-pyrazolo[3,4-b]pyridin-1-yl)(2-methoxyphenyl)methanone;

(3-amino-6-isobutyl-1H-pyrazolo[3,4-b]pyridin-1-yl)(2-methoxyphenyl)methanone;

(3-amino-6-(pyrrolidin-1-yl)-1H-pyrazolo[3,4-b]pyridin-1-yl)(2-methoxyphenyl)methanone; (3-amino-6-(pyrrolidin-1-yl)-1H-pyrazolo[3,4-b]pyridin-1-yl)(2-chlorophenyl)methanone;

(3-amino-6-(pyrrolidin-1-yl)-1H-pyrazolo[3,4-b]pyridin-1-yl)(o-tolyl)methanone;

[3-amino-6-(cyclohexen-1-yl)pyrazolo[3,4-b]pyridin-1-yl]-(2-methoxyphenyl)methanone;

(3-amino-6-cyclopropylpyrazolo[3,4-b]pyridin-1-yl)-(2-methoxyphenyl)methanone 2,2,2-trifluoroacetic acid;

(3-amino-5-chloro-6-cyclopropyl-1H-pyrazolo[3,4-b]pyridin-1-yl)(2-methoxyphenyl)methanone;

(3-amino-5-chloro-6-cyclopropyl-1H-pyrazolo[3,4-b]pyridin-1-yl)(o-tolyl)methanone;

(3-amino-5-fluoro-6-phenyl-1H-pyrazolo[3,4-b]pyridin-1-yl)(2-methoxyphenyl)methanone;

(3-amino-5-fluoro-6-(pyrrolidin-1-yl)-1H-pyrazolo[3,4-b]pyridin-1-yl)(2-methoxyphenyl)methanone;

(3-amino-5-fluoro-6-(pyrrolidin-1-yl)-1H-pyrazolo[3,4-b]pyridin-1-yl)(2-chlorophenyl)methanone;

(3-amino-5-fluoro-6-(pyrrolidin-1-yl)-1H-pyrazolo[3,4-b]pyridin-1-yl)(o-tolyl)methanone;

(3-amino-6-(3,3-difluoroazetidin-1-yl)-5-fluoro-1H-pyrazolo[3,4-b]pyridin-1-yl)(2-methoxyphenyl)methanone;

(3-amino-6-(tert-butyl)-1H-pyrazolo[3,4-b]pyridin-1-yl)(2-methoxyphenyl)methanone;

(3-amino-6-(pyrrolidin-1-yl)-1H-pyrazolo[3,4-d]pyrimidin-1-yl)(2-methoxyphenyl)methanone;

(3-amino-6-(pyrrolidin-1-yl)-1H-pyrazolo[3,4-d]pyrimidin-1-yl)(o-tolyl)methanone;

(3-amino-6-(pyrrolidin-1-yl)-1H-pyrazolo[3,4-d]pyrimidin-1-yl)(2-chlorophenyl)methanone;

(3-amino-6-cyclopropylpyrazolo[3,4-b]pyridin-1-yl)-(1,3-benzodioxol-4-yl) methanone;

(3-amino-6-cyclopropylpyrazolo[3,4-b]pyridin-1-yl)-(2-methylphenyl)methanone;

(3-amino-7,7-dimethyl-5,6,7,8-tetrahydro-1H-pyrazolo[3,4-b]quinolin-1-yl)(2-methoxyphenyl)methanone;

[3-amino-6-(3,4-dihydro-2H-pyran-6-yl)pyrazolo[3,4-b]pyridin-1-yl]-(2-methoxyphenyl)methanone;

[3-amino-6-(cyclopenten-1-yl)pyrazolo[3,4-b]pyridin-1-yl]-(2-methoxyphenyl)methanone; (3-amino-6-(azetidin-1-yl)-1H-pyrazolo[3,4-b]pyridin-1-yl)(2-methoxyphenyl)methanone;

(3-amino-6-(trifluoromethyl)-1H-pyrazolo[3,4-b]pyridin-1-yl)(o-tolyl)methanone;
(3-amino-6-(trifluoromethyl)-1H-pyrazolo[3,4-b]pyridin-1-yl)(2-methoxyphenyl)methanone;
(3-amino-6-(3,3-difluoroazetidin-1-yl)-1H-pyrazolo[3,4-b]pyridin-1-yl)(2-methoxyphenyl)methanone;
(3-amino-6-(3,3-difluoroazetidin-1-yl)-1H-pyrazolo[3,4-b]pyridin-1-yl)(o-tolyl)methanone;
(3-amino-6-cyclopentylpyrazolo[3,4-b]pyridin-1-yl)-(2-methylphenyl)methanone;
[3-amino-6-(cyclopenten-1-yl)pyrazolo[3,4-b]pyridin-1-yl]-(2-methylphenyl)methanone;
(3-amino-6-cyclobutyl-1H-pyrazolo[3,4-b]pyridin-1-yl)(o-tolyl)methanone;
(3-amino-6-cyclobutyl-1H-pyrazolo[3,4-b]pyridin-1-yl)(2-methoxyphenyl)methanone;
(3-amino-6-cyclopropyl-1H-pyrazolo[3,4-b]pyridin-1-yl)(3-fluoro-2-methylphenyl)methanone;
(3-amino-6-((1RS,2RS)-2-methylcyclopropyl)-1H-pyrazolo[3,4-b]pyridin-1-yl)(o-tolyl)methanone;
(3-amino-6-((1RS,2RS)-2-methylcyclopropyl)-1H-pyrazolo[3,4-b]pyridin-1-yl)(2-methoxyphenyl)methanone;
(3-amino-6-cyclopropyl-1H-pyrazolo[3,4-b]pyridin-1-yl)(2,3-dimethylphenyl)methanone;
(3-amino-6-cyclopropyl-1H-pyrazolo[3,4-b]pyridin-1-yl)(cyclohexyl) methanone;
[3-amino-6-(2,5-dihydrofuran-3-yl)pyrazolo[3,4-b]pyridin-1-yl]-(2-methoxyphenyl)methanone;
[3-amino-6-(2,5-dihydrofuran-3-yl)pyrazolo[3,4-b]pyridin-1-yl]-(2-methylphenyl)methanone;
(3-amino-6-cyclopropyl-1H-pyrazolo[3,4-b]pyridin-1-yl)(2-methoxycyclohexyl) methanone;
(3-amino-7-methyl-5,6,7,8-tetrahydro-1H-pyrazolo[3,4-b]quinolin-1-yl)(2-methoxyphenyl)methanone;
(3-amino-6-((trans)-2-fluorocyclopropyl)-1H-pyrazolo[3,4-b]pyridin-1-yl)(2-methoxyphenyl)methanone;
(3-amino-6-cyclopropyl-1H-pyrazolo[3,4-b]pyridin-1-yl)(3-fluoro-2-methoxyphenyl)methanone;
(3-amino-6-cyclopropyl-1H-pyrazolo[3,4-b]pyridin-1-yl)(4-fluoro-2-methoxyphenyl)methanone;
(3-amino-6-(2,2-difluorocyclopropyl)-1H-pyrazolo[3,4-b]pyridin-1-yl)(2-methoxyphenyl)methanone;
(3-amino-6-(2,2-difluorocyclopropyl)-1H-pyrazolo[3,4-b]pyridin-1-yl)(o-tolyl)methanone;
[3-amino-6-[rac-(1R,2R)-2-(trifluoromethyl) cyclopropyl]pyrazolo[3,4-b]pyridin-1-yl]-(2-methoxyphenyl)methanone;
(3-amino-6-((1r,2R,3S)-2,3-dimethylcyclopropyl)-1H-pyrazolo[3,4-b]pyridin-1-yl)(o-tolyl)methanone;
(3-amino-6-((1r,2R,3S)-2,3-dimethylcyclopropyl)-1H-pyrazolo[3,4-b]pyridin-1-yl)(2-methoxyphenyl)methanone;
(3-amino-6-(2,2-difluorocyclopropyl)-1H-pyrazolo[3,4-b]pyridin-1-yl)(3-fluoro-2-methoxyphenyl)methanone;
(3-amino-5-fluoro-6-(pyrrolidin-1-yl)-1H-pyrazolo[3,4-b]pyridin-1-yl)(3-fluoro-2-methoxyphenyl)methanone;
[3-amino-6-(2,5-dihydrofuran-3-yl)pyrazolo[3,4-b]pyridin-1-yl]-(3-fluoro-2-methoxyphenyl)methanone;
rac-(cis)-4-(3-amino-6-cyclopropylpyrazolo[3,4-b]pyridine-1-carbonyl)-3-methylpiperidin-2-one;
(3-amino-6-cyclopropyl-1H-pyrazolo[3,4-b]pyridin-1-yl)(2-ethylphenyl) methanone;
(3-amino-6-cyclopropyl-1H-pyrazolo[3,4-b]pyridin-1-yl)(2-(difluoromethoxy) phenyl) methanone;
(3-amino-6-cyclopropyl-1H-pyrazolo[3,4-b]pyridin-1-yl)(5-methyloxazol-4-yl) methanone;
(3-amino-6-cyclopropyl-1H-pyrazolo[3,4-b]pyridin-1-yl)(4-methylthiazol-5-yl) methanone;
(3-amino-6-cyclopropyl-1H-pyrazolo[3,4-b]pyridin-1-yl)(2-methyltetrahydrofuran-3-yl) methanone;
(3-amino-6-cyclopropyl-1H-pyrazolo[3,4-b]pyridin-1-yl)((2S,3R)-2-methyltetrahydrofuran-3-yl) methanone;
3-(3-amino-6-cyclopropyl-1H-pyrazolo[3,4-b]pyridine-1-carbonyl)-2-methylbenzonitrile;
(3-amino-6-cyclopropyl-1H-pyrazolo[3,4-b]pyridin-1-yl)(tetrahydro-2H-pyran-4-yl) methanone;
(3-amino-6-cyclopropyl-1H-pyrazolo[3,4-b]pyridin-1-yl)(2-methylpyridin-3-yl) methanone;
4-(3-amino-6-cyclopropyl-1H-pyrazolo[3,4-b]pyridine-1-carbonyl) piperidin-2-one;
(3-amino-6-cyclopropyl-1H-pyrazolo[3,4-b]pyridin-1-yl)(2-methoxy-3-methylphenyl)methanone;
(3-amino-6-(I-methylcyclopropyl)-1H-pyrazolo[3,4-b]pyridin-1-yl)(o-tolyl)methanone;
(3-amino-6-(2,2-difluorocyclopropyl)-1H-pyrazolo[3,4-b]pyridin-1-yl)(2-methyl pyridin-3-yl) methanone;
(3-amino-6-(2,2-difluorocyclopropyl)-1H-pyrazolo[3,4-b]pyridin-1-yl)(2-methyltetrahydrofuran-3-yl) methanone;
(3-amino-6-cyclopropyl-1H-pyrazolo[3,4-b]pyridin-1-yl)(3-chloro-2-methoxyphenyl)methanone;
3-(3-amino-6-cyclopropyl-1H-pyrazolo[3,4-b]pyridine-1-carbonyl)-2-methoxybenzonitrile;
(3-amino-6-cyclopropyl-1H-pyrazolo[3,4-b]pyridin-1-yl)(tetrahydro-2H-pyran-3-yl) methanone;
(3-amino-6-cyclopropyl-1H-pyrazolo[3,4-b]pyridin-1-yl)(3-methylpyrazin-2-yl) methanone;
(3-amino-6-cyclopropyl-1H-pyrazolo[3,4-b]pyridin-1-yl)(2-methoxypyridin-3-yl) methanone;
(3-amino-6-cyclopropyl-1H-pyrazolo[3,4-b]pyridin-1-yl)(2-chloropyridin-3-yl) methanone;
(3-amino-6-cyclopropyl-1H-pyrazolo[3,4-b]pyridin-1-yl)(2-(trifluoromethyl) pyridin-3-yl) methanone;
(3-amino-6-cyclopropyl-1H-pyrazolo[3,4-b]pyridin-1-yl)(3-methylpyridazin-4-yl) methanone;
(3-amino-6-cyclopropyl-1H-pyrazolo[3,4-b]pyridin-1-yl)(3-methylisothiazol-4-yl) methanone;
[3-amino-6-[(1R,4S)-3-azabicyclo[2.2.1]heptan-3-yl]pyrazolo[3,4-b]pyridin-1-yl]-(2-methoxyphenyl)methanone;
(3-amino-6-cyclopropyl-1H-pyrazolo[3,4-b]pyridin-1-yl)((2R,3S)-3-methyltetrahydrofuran-2-yl) methanone; and
[3-amino-6-(7-azabicyclo[2.2.1]heptan-7-yl)pyrazolo[3,4-b]pyridin-1-yl]-(2-methoxyphenyl)methanone;

or pharmaceutically acceptable salts thereof.

2. The compound according to claim 1, selected from the group consisting of:

(3-amino-6-cyclopropylpyrazolo[3,4-b]pyridin-1-yl)-(2-methoxyphenyl)methanone 2,2,2-trifluoroacetic acid;
(3-amino-6-cyclopropylpyrazolo[3,4-b]pyridin-1-yl)-(2-methylphenyl)methanone;
[3-amino-6-(cyclopenten-1-yl)pyrazolo[3,4-b]pyridin-1-yl]-(2-methoxyphenyl)methanone;
(3-amino-6-(trifluoromethyl)-1H-pyrazolo[3,4-b]pyridin-l-yl)(2-methoxyphenyl)methanone;
[3-amino-6-(cyclopenten-1-yl)pyrazolo[3,4-b]pyridin-1-yl]-(2-methylphenyl)methanone;
(3-amino-6-cyclobutyl-1H-pyrazolo[3,4-b]pyridin-l-yl)(2-methoxyphenyl)methanone;
(3-amino-6-((1RS,2RS)-2-methylcyclopropyl)-1H-pyrazolo[3,4-b]pyridin-1-yl)(o-tolyl)methanone;

(3-amino-6-((1RS,2RS)-2-methylcyclopropyl)-1H-pyrazolo[3,4-b]pyridin-1-yl)(2-methoxyphenyl)methanone;

(3-amino-6-(2,2-difluorocyclopropyl)-1H-pyrazolo[3,4-b]pyridin-1-yl)(2-methoxyphenyl)methanone;

(3-amino-6-((1r,2R,3S)-2,3-dimethylcyclopropyl)-1H-pyrazolo[3,4-b]pyridin-1-yl)(2-methoxyphenyl)methanone;

[3-amino-6-(2,5-dihydrofuran-3-yl)pyrazolo[3,4-b]pyridin-1-yl]-(3-fluoro-2-methoxyphenyl)methanone;

(3-amino-6-cyclopropyl-1H-pyrazolo[3,4-b]pyridin-1-yl)(2-methylpyridin-3-yl) methanone;

(3-amino-6-(2,2-difluorocyclopropyl)-1H-pyrazolo[3,4-b]pyridin-1-yl)(2-methylpyridin-3-yl) methanone;

3-(3-amino-6-cyclopropyl-1H-pyrazolo[3,4-b]pyridine-1-carbonyl)-2-methoxybenzonitrile;

(3-amino-6-cyclopropyl-1H-pyrazolo[3,4-b]pyridin-1-yl)(2-methoxypyridin-3-yl) methanone; and (3-amino-6-cyclopropyl-1H-pyrazolo[3,4-b]pyridin-1-yl)(2-chloropyridin-3-yl) methanone;

or pharmaceutically acceptable salts thereof.

3. Pharmaceutical compositions comprising compounds of claim 1 or their pharmaceutically acceptable salts and one or more pharmaceutically acceptable excipients.

4. A method for the treatment of Lung Adenocarcinoma, Melanoma, Pancreatic Adenocarcinoma, Head and Neck Squamous Cell Carcinoma, Lung Squamous Cell Carcinoma, Esophageal Carcinoma, Glioblastoma Multiforme, Mesothelioma, or a combination thereof, which method comprises administering compounds of claim 1 or their pharmaceutically acceptable salts to a subject.

5. The method of claim 4, wherein the method is for the treatment of Head and Neck Squamous Cell Carcinoma, Glioblastoma Multiforme, or a combination thereof.

* * * * *